(12) United States Patent
Maddocks et al.

(10) Patent No.: US 12,042,477 B2
(45) Date of Patent: Jul. 23, 2024

(54) DIETARY PRODUCT DEVOID OF AT LEAST TWO NON ESSENTIAL AMINO ACIDS

(71) Applicant: CANCER RESEARCH TECHNOLOGY LIMITED, London (GB)

(72) Inventors: Oliver D. K. Maddocks, Glasgow (GB); Karen Vousden, Glasgow (GB)

(73) Assignee: CANCER RESEARCH TECHNOLOGY LIMITED, London (GB)

( * ) Notice: Subject to any disclaimer, the term of this patent is extended or adjusted under 35 U.S.C. 154(b) by 0 days.

(21) Appl. No.: 15/999,666

(22) PCT Filed: Feb. 22, 2017

(86) PCT No.: PCT/GB2017/050458
§ 371 (c)(1),
(2) Date: Aug. 20, 2018

(87) PCT Pub. No.: WO2017/144877
PCT Pub. Date: Aug. 31, 2017

(65) Prior Publication Data
US 2020/0230092 A1 Jul. 23, 2020

(30) Foreign Application Priority Data

Feb. 23, 2016 (GB) .................................. 1603098
May 27, 2016 (GB) .................................. 1609441

(51) Int. Cl.
| *A01N 43/00* | (2006.01) |
| *A01N 43/46* | (2006.01) |
| *A61K 9/00* | (2006.01) |
| *A61K 31/198* | (2006.01) |
| *A61K 31/55* | (2006.01) |
| *A61K 45/06* | (2006.01) |
| *A61P 35/00* | (2006.01) |

(52) U.S. Cl.
CPC .......... *A61K 31/198* (2013.01); *A61K 9/0056* (2013.01); *A61K 9/0095* (2013.01); *A61K 45/06* (2013.01); *A61P 35/00* (2018.01)

(58) Field of Classification Search
None
See application file for complete search history.

(56) References Cited

U.S. PATENT DOCUMENTS

| 3,832,465 A | 8/1974 | Ghadimi |
| 4,734,401 A | 3/1988 | Blouin |
| 4,988,724 A | 1/1991 | Ajani et al. |
| 6,218,420 B1 | 4/2001 | Dioguardi |
| 6,713,501 B1 | 3/2004 | Walser |
| 10,973,251 B1 | 4/2021 | Li et al. |
| 11,241,407 B2 | 2/2022 | Li et al. |
| 2003/0129262 A1 | 7/2003 | Epner et al. |
| 2006/0280840 A1 | 12/2006 | Robertson |
| 2007/0270355 A1 | 11/2007 | Garcia et al. |
| 2007/0286909 A1 | 12/2007 | Smith et al. |
| 2008/0317886 A1 | 12/2008 | Sparkman |
| 2011/0118528 A1* | 5/2011 | Longo ................ A61K 31/20 600/1 |
| 2011/0153221 A1 | 6/2011 | Stefanon et al. |
| 2013/0123363 A1 | 5/2013 | Uesugi et al. |
| 2014/0087970 A1 | 3/2014 | Possemato et al. |
| 2014/0100357 A1 | 4/2014 | Miao et al. |
| 2014/0170259 A1 | 6/2014 | Poels et al. |
| 2014/0363417 A1 | 12/2014 | Cheng et al. |
| 2015/0315561 A1 | 11/2015 | Schabbauer et al. |
| 2017/0143025 A1 | 5/2017 | Rason et al. |
| 2022/0054444 A1 | 2/2022 | Maddocks |
| 2022/0117943 A1 | 4/2022 | Maddocks |
| 2022/0193447 A1 | 6/2022 | Maddocks et al. |
| 2022/0400730 A1 | 12/2022 | Li et al. |
| 2023/0277492 A1 | 9/2023 | Maddocks et al. |

FOREIGN PATENT DOCUMENTS

| JP | 2005289938 A | 10/2005 |
| JP | 2014512803 A | 5/2014 |
| WO | WO-9802441 A2 | 1/1998 |
| WO | WO-0114387 A1 | 3/2001 |
| WO | WO-2006043090 A1 | 4/2006 |
| WO | WO-2009077766 A1 | 6/2009 |
| WO | WO-2010075007 A3 | 11/2010 |
| WO | WO-2011092469 A1 | 8/2011 |
| WO | WO-2011143579 A2 | 11/2011 |
| WO | WO-2012116229 A2 | 8/2012 |

(Continued)

OTHER PUBLICATIONS

Paddon-Jones et al. (Differential stimulation of muscle protein synthesis in elderly humans following isocaloric ingestion of amino acids or whey protein. Experimental gerontology. Feb. 1, 2006;41(2):215-9).*
McCormack et al. ("Oral nutritional supplement fortified with beta-alanine improves physical working capacity in older adults: a randomized, placebo-controlled study." Experimental gerontology 48.9 (2013): 933-939) (Year: 2013).*
Wernerman (J. Clinical use of glutamine supplementation. J Nutr. Oct. 2008;138(10):2040S-2044S. doi: 10.1093/jn/138.10.2040S. PMID: 18806121) (Year: 2008).*
Lancha et al. (Effect of aspartate, asparagine, and carnitine supplementation in the diet on metabolism of skeletal muscle during a moderate exercise. Physiol Behav. Feb. 1995;57(2):367-71. doi: 10.1016/0031-9384(94)00243-x. PMID: 7716217). (Year: 1995).*

(Continued)

*Primary Examiner* — Layla Soroush
(74) *Attorney, Agent, or Firm* — Cooley LLP

(57) ABSTRACT

The present invention relates to a dietary product comprising a plurality of amino acids, wherein the dietary product comprises all the essential amino acids and wherein the dietary product is substantially devoid of at least two non-essential amino acids; methods and uses thereof in the treatment of cancer; stratification methods and biomarkers for such applications.

22 Claims, 35 Drawing Sheets
Specification includes a Sequence Listing.

(56) References Cited

FOREIGN PATENT DOCUMENTS

| | | |
|---|---|---|
| WO | WO-2014049566 A2 | 4/2014 |
| WO | WO-2015075483 A1 | 5/2015 |
| WO | WO-2016130918 A1 | 8/2016 |
| WO | WO2017/053328 | 3/2017 |
| WO | WO-2017144877 A1 | 8/2017 |
| WO | WO-2018071873 A2 | 4/2018 |
| WO | WO-2019092455 A1 | 5/2019 |
| WO | WO-2019118549 A1 | 6/2019 |
| WO | WO-2019211605 A1 | 11/2019 |
| WO | WO-2021016132 A1 | 1/2021 |
| WO | WO-2021247724 A1 | 12/2021 |
| WO | WO-2021247923 A1 | 12/2021 |
| WO | WO-2022015951 A2 | 1/2022 |
| WO | WO-2022132981 A1 | 6/2022 |
| WO | WO-2023130140 A2 | 7/2023 |

OTHER PUBLICATIONS

Institute of Medicine, Food and Nutrition Board. (Dietary reference intakes for water, potassium, sodium, chloride, and sulfate. Washington, DC: National Academy Press; 2005) (Year: 2005).*
International Search Report and Written Opinion, PCT/GB2017/050458, dated Jul. 18, 2017, 20 pages.
Maddocks Odk et al. Serine starvation induces stress and p53-dependent metabolic remodelling in cancer cells. Nature. Dec. 2013; 493(7433): 542-546.
Anonymous. ClinicalTrials.gov Archive. NCT02337894 on Jan. 13, 2015.Retrieved from the Internet: https://clinicaltrials.gov/archive/NCT. Retrieved on Apr. 2, 2017. 5 pages.
Rose WC et al. Growth on diets devoid of glycine, serine, and cystine, and low in choline. J Biol Chem. 1952; 194: 321-328.
Maddocks Odk et al. Serine metabolism supports the methionine cycle and DNR/RNA methylation through de novo ATP synthesis in cancer cells. Molecular Cell. 2016; 61: 210-221.
Bunz F et al. Requirement for p53 and p21 to sustain G2 arrest after DNA damage. Science. Nov. 1998; 282: 1497-1501.
Labuschagne CF et al. Serine, but not glycine, supports one-carbon metabolism and proliferation of cancer cells, Cell Reports 7. 1248-1258, May 22, 2014.
Lopez-Lazaro M. Selective amino acid restriction therapy (SAART); a non-pharmacological strategy against all types of cancer cells. Oncoscience. 2015; 2(10): 857-866.
Polet F et al. Reducing the serine availability complements the inhibition of the glutamine metabolism to block leukemia cell growth. Oncotarget. Jan. 2016; 7(2): 1765-1776.
Vigneron AM et al. Cytoplasmic ASPP1 Inhibits apoptosis through the control of YAP. Genes & Development. 2010; 24: 2430-2439.
Search Report, Intellectual Property Office, United Kingdom Application No. GB1609441.9, dated Mar. 1, 2017, 5 pages.
Kshattry S. et al. "Abstract 367: Assessing the therapeutic efficacy of Cyst(e)inase to induce oxidative stress mediated cytotoxicity in pancreatic cancer cells" Experimental and Molecular Therapeutics, 4 pages, 2016.
Zhang W. et al., "Stromal control of cystine metabolism promotes cancer cell survival in chronic lymphocytic leukaemia" Nature Cell Biology, 14(3):276-286 2012.
Bartlett, David L., et al., "Effect of growth hormone and protein intake on tumor growth and host cachexia", Surgery, 1995, vol. 117, No. 3, pp. 260-267.
Okada, Kenzo , et al., "Tumor glutamine level is negatively correlated with tumor weight in tumor-bearing rats administered a glutamine antagonist and a new imbalanced amino acid solution", Journal of Clinical Biochemistry and Nutrition, 1992, vol. 12, No. 3, pp. 183-191.
Adams et al., "The c-myc oncogene driven by immunoglobulin enhancers induces lymphoid malignancy in transgenic mice" Nature (1985) 318:533-538.
Barker et al., "Crypt stem cells as the cells-of-origin of intestinal cancer" Nature (2009) 457:608-611.
Bertino et al., "Targeting tumors that lack methylthioadenosine phosphorylase (MTAP) activity: current strategies" Cancer Biol Ther. Apr. 1, 2011; 11(7):627-632.
Commisso et al., "Macropinocytosis of protein is an amino acid supply route in Ras-transformed cells" Nature (2013) 497:633-637.
Donehower, et al. "Mice deficient for p53 are developmentally normal but susceptible to spontaneous tumours" Nature (1992) 356:215-221.
Dredge, K et al., "The polyamine analog PG11047 potentiates the antitumor activity of cisplatin and bevacizumab in preclinical models of lung and prostate cancer" Cancer Chemother Pharmacol. 65, 191-195 (2009).
Fiatarone et al., "Exercise training and nutritional supplementation for physical frailty in very elderly people" N. Engl. J. Med. Jun. 23, 1994; 330(25):1769-75.
Fiatarone Singh et al., "The effect of oral nutritional supplements on habitual dietary quality and quantity in frail elders" J. Nutr. Health Aging (2000) 4(1):5-12.
Final Office Action dated Aug. 10, 2023, for U.S. Appl. No. 17/338,283, filed Jun. 3, 2021, 14 pages.
Finkelstein et al., "Methionine metabolism in mammals. The methionine-sparing effect of cystine" J Biol Chem. 263(24):11750-11754 (1998).
Hingorani et al., "Trp53R172H and KrasG12D cooperate to promote chromosomal instability and widely metastatic pancreatic ductal adenocarcinoma in mice" Cancer Cell (2005) 7:469-483.
Hirakawa et al., "Comparative utilization of a crystalline amino acid diet and a methionine-fortified casein diet by young rats and mice" Nutr Res (1984) 4(5):891-895.
Institute of Medicine, "Dietary Reference Intakes for Energy, Carbohydrate, Fiber, Fat, Fatty Acids, Cholesterol, Protein and Amino Acids" Chapters 6, 7, and 8, Sep. 2002, 323 pages.
International Search Report and Written Opinion issued in PCT/2021/35780 dated Oct. 1, 2021. 11 pages.
International Search Report and Written Opinion dated Apr. 11, 2022, for PCT/US2021/063639, filed on Dec. 15, 2021, 8 pages.
International Search Report and Written Opinion dated Jun. 26, 2023, for PCT/US2023/60025, filed on Jan. 3, 2023, 9 pages.
Labadie et al., "Reimagining IDO Pathway Inhibition in Cancer Immunotherapy via Downstream Focus on the Tryptophan-Kynurenine-Aryl Hydrocarbon Axis" Clin Cancer Res. Mar. 1, 2019; 25(5):1462-1471.
Locasale, "Serine, glycine and one-carbon units: cancer metabolism in full circle" Nat Rev Cancer. Aug. 2013; 13(8):572-583.
Miyo, M. et al., "Metabolic Adaptation to Nutritional Stress in Human Colorectal Cancer" Scientific Reports (2016) vol. 6, No. 1, 38415, 13 pages.
Morton et al., "Mutant p53 drives metastasis and overcomes growth arrest/senescence in pancreatic cancer" PNAS USA (2010) 107:246-251.
Moser et al., "A dominant mutation that predisposes to multiple intestinal neoplasia in the mouse" Science (1990) 322-324.
NAS. IOM. Food and Nutrition Board, "Dietary Reference Intakes: RDA and AI for Vitamins and Elements" (2017) 3 pages.
Non-Final Office Action dated Jan. 5, 2023, for U.S. Appl. No. 17/338,283, filed Jun. 3, 2021, 14 pages.
Non-Final Office Action dated Jul. 7, 2023, for U.S. Appl. No. 18/174,706, filed Feb. 27, 2023, 13 pages.
Paddon-Jones et al., "Amino acid ingestion improves muscle protein synthesis in the young and elderly" Am J Physiol Endocrinol Metab. Mar. 2004; 286(3):E321-E328.
PCT/US2021/035780 International Preliminary Report on Patentability (Chapter I) dated Dec. 6, 2022. 9 Pages.
Possemato et al., "Functional genomics reveal that the serine synthesis pathway is essential in breast cancer" Nature Aug. 18, 2011; 476(7360):346-350.
Ran et al., "Genome engineering using the CRISPR-Cas9 system" Nat Protoc. Nov. 2013; 8(11):2281-2308.
Sahu et al., "Proline Starvation Induces Unresolved ER Stress and Hinders mTORC1-Dependent Tumorigenesis" Cell Metabolism (2016) 24:753-761.
Snezhkina, A.V. et al., "The Dysregulation of Polyamine Metabolism in Colorectal Cancer Is Associated with Overexpression of

(56) References Cited

OTHER PUBLICATIONS c-Myc and C/EBPβ rather than Enterotoxigenic Bacteroides fragilis Infection" Oxid Med Cell Longev. (2016) Article ID 2353560, 11 pages.

Solerte et al., "Metabolic effects of orally administered amino acid mixture in elderly subjects with poorly controlled type 2 diabetes mellitus" Am J Cardiol. Apr. 22, 2004; 93(8A):23A-29A.

Su et al., "Multiple intestinal neoplasia caused by a mutation in the murine homolog of the APC gene" Science (1992) 256:668-670.

Walpole et al., "The weight of nations: an estimation of adult human biomass" BMC Public Health. Jun. 18, 2012; 12:439.

Ying et al., "Oncogenic Kras maintains pancreatic tumors through regulation of anabolic glucose metabolism" Cell (2012) 149:656-670.

Zhang et al., "Application of Holistic Liquid Chromatography-High Resolution Mass Spectrometry Based Urinary Metabolomics for Prostate Cancer Detection and Biomarker Discovery" PLoS One (2013) 8(6):e65880, 10 pages.

Zhang et al., "Polyamine pathway activity promotes cysteine essentiality in cancer cells" Nature Metabolism (2020) 2:1062-1076, 27 pages.

Extended European Search Report mailed on Feb. 1, 2024, for EP Application No. 23151551.1, 27 pages.

Fu et al., "Specific amino acid dependency regulates invasiveness and viability of androgen-independent prostate cancer cells" Nutr Cancer. (2003) 45(1):60-73.

Ge et al., "Activation of caspases and cleavage of Bid are required for tyrosine and phenylalanine deficiency-induced apoptosis of human A375 melanoma cells" Arch Biochem Biophys. (2002) Jul. 1; 403(1):50-58.

Yan et al., "Effects of complex unbalanced amino acids on tumors in mice bearing liver cancer H22" Chinese Journal of Clinical Oncology (2011) 38(3):134-137.

Amelio et al., "Serine and glycine metabolism in cancer" Trends Biochem Sci. (2014) Apr. 39(4):191-198.

Badgley et al., "Absract A41: Leveraging metabolic dependencies in cancer: Cystein addiction in pancreatic cancer cells" Mol Cancer Research (2016) 14(1_Supp): A41, 4 pages.

Bassiri et al., "Translational development of difluoromethylornithine (DFMO) for the treatment of neuroblastoma" Transl Pediatr. (2015) Jul; 4(3):226-238.

Blau et al., eds., "Laboratory Guide to the Methods in Biochemical Genetics" (2008) Berlin Heidelberg, Germany: Springer Verlag. Page 74. 59 pages.

CAS Registry No. 1036730-42-3, STN entry date: Jul. 28, 2008, Pidilizumab, 1 page.

CAS Registry No. 1374853-91-4, STN entry date: May 31, 2012, Pembrolizumab, 1 page.

CAS Registry No. 1380723-44-3, STN entry date: Jul. 3, 2012, Atezolizumab, 1 page.

CAS Registry No. 1428935-60-7, STN entry date: Apr. 23, 2013, Durvalumab, 1 page.

CAS Registry No. 1537032-82-8, STN entry date: Feb. 4, 2014, Avelumab, 1 page.

CAS Registry No. 1801342-60-8, STN entry date: Aug. 4, 2015, Cemiplimab, 1 page.

CAS Registry No. 477202-00-9, dated Dec. 19, 2002, 1 page.

CAS Registry No. 70052-12-9, STN entry date: Nov. 16, 1984, Eflornithine, 2 pages.

CAS Registry No. 946414-94-4, STN entry date: Sep. 7, 2007, Nivolumab, 1 page.

CAS Registry No. 96020-91-6, STN entry date: Apr. 21, 1985, Ornithine, 1 page.

Corsetti et al., "Protect and Counter-attack: Nutritional Supplementation with Essential Amino acid Ratios Reduces Doxorubicin-induced Cardiotoxicity in vivo and promote Cancer Cell Death in vitro" J. Cytol. Histol. (2015) 6:5, 1000354, 2 pages.

Extended European Search Report mailed on Sep. 18, 2023, for EP Application No. 23166882.3, 11 pages.

Faubert et al., "Stable isotope tracing to assess tumor metabolism in vivo" Nat Protoc. (2021) Nov. 16(11):5123-5145.

Final Office Action mailed on Nov. 24, 2023, for U.S. Appl. No. 18/174,706, filed Feb. 27, 2023, 13 pages.

Geck et al., "Nonessential amino acid metabolism in breast cancer" Advances in Biological Regulation (2016) 62:11-17.

Gravel et al., "Serine deprivation enhances antineoplastic activity of biguanides" Cancer Res. (2014) Dec. 15; 74(24):7521-7533.

Harenza et al., "Transcriptomic profiling of 39 commonly-used neuroblastoma cell lines" Sci Data. (2017) Mar. 28: 4:170033. 8 pages.

Hogarty et al., "ODC1 is a critical determinant of MYCN oncogenesis and a therapeutic target in neuroblastoma" Cancer Res. (2008) Dec 1; 68(23): 9735-9745.

Holbert et al., "Polyamines in cancer: integrating organismal metabolism and antitumour immunity" Nat Rev Cancer.(2022) Aug. 22(8):467-480.

Hui et al., "Glucose feeds the TCA cycle via circulating lactate" Nature. (2017) Nov 2; 551(7678):115-118.

Hui et al., "Quantitative Fluxomics of Circulating Metabolites" Cell Metab. (2020) Oct 6; 32(4):676-688. e4.

International Search Report and Written Opinion issued in PCT/US2021/035476 on Oct. 12, 2021. 10 pages.

Kocak et al., "Hox-C9 activates the intrinsic pathway of apoptosis and is associated with spontaneous regression in neuroblastoma" Cell Death Dis. (2013) Apr. 11; 4(4): e586. 11 pages.

Lewis et al., "A subset analysis of a phase II trial evaluating the use of DFMO as maintenance therapy for high-risk neuroblastoma" Int J Cancer. (2020) Dec 1; 147(11):3152-3159.

Liberzon et al., "Molecular signatures database (MSigDB) 3.0" Bioinformatics. (2011) Jun. 15; 27(12):1739-1740.

Logiudice et al., "Alpha-Difluoromethylornithine, an Irreversible Inhibitor of Polyamine Biosynthesis, as a Therapeutic Strategy against Hyperproliferative and Infectious Diseases" Med Sci (Basel). (2018) Feb 8; 6(1):12. 17 pages.

Partial European Search Report mailed on Sep. 20, 2023, for EP Application No. EP 23151551.1, 23 pages.

Rounbehler et al., "Targeting ornithine decarboxylase impairs development of MYCN-amplified neuroblastoma" Cancer Res. (2009) Jan. 15; 69(2):547-553.

Sholler et al., "A Phase I Trial of DFMO Targeting Polyamine Addiction in Patients with Relapsed/Refractory Neuroblastoma" PLoS One. (2015) May 27;10(5):e0127246. 20 pages.

Sholler et al., "Maintenance DFMO Increases Survival in High Risk Neuroblastoma" Sci Rep. (2018) Sep. 27; 8(1):14445. 9 pages.

Soldin et al., "Pediatric reference ranges" 3rd ed., Washington: AACC Press, (1999) pp. 11-20.

Su et al., "Metabolite Spectral Accuracy on Orbitraps" Anal Chem. (2017) Jun. 6; 89(11): 5940-5948.

Tang et al., "Cystine Deprivation Triggers Programmed Necrosis in VHL-Deficient Renal Cell Carcinomas" Cancer Res. (2016) Apr 1; 76(7):1892-1903.

Trumbo et al., "Dietary reference intakes for energy, carbohydrate, fiber, fat, fatty acids, cholesterol, protein and amino acids" J Am Diet Assoc. (2002) Nov; 102(11):1621-1630.

Uniprot P01137, Sep. 13, 2023, 14 pages.
Uniprot P14784, Sep. 13, 2023, 7 pages.
Uniprot P16410, Sep. 13, 2023, 11 pages.
Uniprot P25942, Sep. 13, 2023, 8 pages.
Uniprot P43489, Sep. 13, 2023, 6 pages.
Uniprot Q07011, Sep. 13, 2023, 6 pages.
Uniprot Q15116, Sep. 13, 2023, 9 pages.
Uniprot Q495A1, Sep. 13, 2023, 5 pages.
Uniprot Q5ZPR3, Sep. 13, 2023, 9 pages.
Uniprot Q8TDQ0, Sep. 13, 2023, 9 pages.
Uniprot Q9H7M9, Sep. 13, 2023, 7 pages.
Uniprot Q9NZQ7, Sep. 13, 2023, 9 pages.
Uniprot Q9Y6W8, Sep. 13, 2023, 4 pages.

Wang et al., "Peak Annotation and Verification Engine for Untargeted LC-MS Metabolomics" Anal Chem. (2019) Feb 5; 91(3):1838-1846.

(56) References Cited

OTHER PUBLICATIONS

Weiss et al. "Targeted Expression of MYCN Causes Neuroblastoma in Transgenic Mice", The EMBO Journal (1997), 16(11): 2985-2995.

Wu et al., "Dietary protein intake and human health" Food Funct. (2016) Mar.; 7(3):1251-1265.

Butler et al., "Amino Acid Depletion Therapies: Starving Cancer Cells to Death," Trends in Endocrinology and Metabolism (2021) Jun.; 32(6):367-381.

Casero Jr. et al., "Polyamine metabolism and cancer: treatments, challenges and opportunities," Nature Reviews Cancer. (2018) Nov.; 18(11):681-695.

Cavuoto et al., "A review of methionine dependency and the role of methionine restriction in cancer growth control and life-span extension" Cancer Treatment Reviews (2012) Oct.; 38(6):726-736.

Doxsee et al., "Sulfasalazine-Induced Cystine Starvation: Potential Use for Prostate Cancer Therapy" Prostate (2007) Feb. 1; 67(2):162-171.

Non-Final Office Action mailed on Feb. 23, 2024, for U.S. Appl. No. 17/338,283, filed Jun. 3, 2021, 13 pages.

Non-Final Office Action mailed on Mar. 29, 2024, for U.S. Appl. No. 17/337,077, filed Jun. 2, 2021, 14 pages.

Tajan et al., "Serine synthesis pathway inhibition cooperates with dietary serine and glycine limitation for cancer therapy" Nat Commun. (2021) Jan. 14; 12(1):366. 16 pages.

Yan et al., "Effects of complex unbalanced amino acids on tumors in mice bearing liver cancer H22" Chinese Journal of Clinical Oncology (2011) 38(3):134-137 (with full English Translation). 8 total pages.

\* cited by examiner f.

homoC-cys = homocysteine + cysteine dimer
Homocysteine = homocysteine + homocysteine dimer homoC-cys = homocysteine + cysteine dimer
Homocysteine = homocysteine + homocysteine dimer a.

b.

DIETARY PRODUCT DEVOID OF AT LEAST TWO NON ESSENTIAL AMINO ACIDS

CROSS REFERENCE TO RELATED APPLICATIONS

The present application is a National Entry Application of PCT Application No. PCT/GB2017/050458, filed on Feb. 22, 2017, which claims the benefit of Great Britain Application No. 1603098.3, filed on Feb. 23, 2016 and Great Britain Application No. 1609441.9, filed on May 27, 2016, each of which are incorporated herein by reference in their entirety.

STATEMENT REGARDING ELECTRONIC FILING OF A SEQUENCE LISTING

A Sequence Listing in ASCII text format, submitted under 37 C.F.R. § 1.821, entitled 9052-348_ST25.txt 2,593 bytes in size, generated on Dec. 5, 2019 and filed via EFS-Web, is provided in lieu of a paper copy. This Sequence Listing is hereby incorporated by reference into the specification for its disclosures.

FIELD OF THE INVENTION

The present invention generally relates to the field of dietary therapies for treating cancer. More particularly, the present invention relates to altering the levels of amino acids in the diet so as to treat cancers and improve existing cancer therapies. The invention also relates to biomarkers for identifying patients that will benefit from dietary therapies for treating cancer and methods and kits using said biomarkers.

BACKGROUND OF THE INVENTION

Cancer is a disease where cells undergo uncontrolled growth, growing and dividing beyond the normal limits of cell growth. These cells can invade and destroy surrounding tissues. Furthermore, cancer cells can metastasize, where they can spread to other areas of the body via the blood or lymphatic system.

Cancer treatment can involve surgery to remove the tumours, radiotherapy to reduce tumour size, or pharmacotherapy/chemotherapy, using drugs or other medicines to treat the cancers. Survival rates for cancers vary between cancer types; however, for cancer which has metasized rates are especially low. A key reason for this is the fact that pharmacotherapeutic/chemotherapeutic treatments often fail, rarely completely eradicating the cancer. Normal, non-cancerous, cells can only tolerate a certain dose of the pharmacotherapeutic/chemotherapeutic agent, resulting in sub-optimal doses for treating cancers being utilised to prevent too many adverse side effects. To compound the problem, agents have limited selectivity for cancerous cells over normal cells, and cancerous cells can become resistant to the pharmacotherapeutic/chemotherapeutic agents over treatment periods. Surviving cancer cells are typically still able to undergo uncontrolled proliferation, and the cancer persists. This has led to researchers looking for novel methods of treating cancers.

In recent years, attention has turned to cancer metabolism, and, in particular, how cancerous cells differ to normal cells so as to present the rapid, uncontrolled cell growth typically associated with disease. It is evident that cancers can reprogram their metabolism in order to be able to grow, generate new cells and adapt to metabolic stress. In treating cancers, specific metabolic pathway enzymes can be targeted, or alternatively, the chemicals and/or metabolites utilised in the pathways can be targeted. Proteins are a key component of cells, and protein synthesis pathways are key to the growth of cancerous cells.

Proteins can be synthesised from amino acids, and there are 20 known biologically active amino acids in mammals. These can be synthesised in the body (non-essential amino acids), but those which cannot be are essential components of the diet (essential amino acids). Cancerous cells are highly dependent on utilisation of non-essential amino acids to support proliferation. Some cancers can synthesise these de novo to support proliferation, while others rely on uptake of exogenous amino acids. (Jason W. Locasale, Nature Reviews Cancer, 2013, 13, 572-583; R. Possemato et al, Nature, 2011 476, 346-350; O. Maddocks et al, Nature, 2013, 493, 542-546; C. Labuschagne et al, Cell Rep. 2014, 22, 7(4), 1248-58). Non-essential amino acids are used for protein synthesis and also many other anabolic processes necessary for cancer cell growth.

The reliance of cancers on exogenous amino acids has the potential to be exploited to treat cancers, by modulating the amount of exogenous amino acids which they can obtain, through limiting levels of amino acids in the diet. This starvation of cancerous cells of essential components required for grow and survive may have the effect of preventing cancer growth or inducing cancerous cell death. This could be used alone as a therapy, or in conjunction with other strategies such as radiotherapy and pharmacotherapy/chemotherapy.

Such strategies will require improved methods of stratifying cancer types so as to identify patients and patient populations that may benefit from such therapies.

Accordingly there remains a need for improved methods of identifying patients and patient populations that will benefit from metabolically targeted therapies.

BRIEF SUMMARY OF THE DISCLOSURE

In accordance with the present inventions there is provided a dietary product comprising a plurality of amino acids, wherein the dietary product comprises all the essential amino acids and wherein the dietary product is substantially devoid of at least two non-essential amino acids. Suitably, the dietary product may comprise at least 9 amino acids.

At least one of the substantially devoid non-essential amino acids may be selected from the group consisting of: glycine, serine, cysteine, tyrosine and arginine.

The at least two substantially devoid non-essential amino acids may comprise two or more of the following amino acids: glycine, serine, cysteine, tyrosine and arginine. Suitably, the dietary product may be substantially devoid of:

a. Glycine, serine and cysteine;
  b. Glycine serine and arginine;
  c. Glycine serine and tyrosine;
  d. Glycine, serine, arginine and cysteine;
  e. Glycine, serine, tyrosine and cysteine;
  f. Cysteine and arginine;
  g. Cysteine and tyrosine;
  h. Cysteine and glycine;
  i. Cysteine, tyrosine and arginine; or
  j. Glycine, serine, arginine, tyrosine and cysteine.

Suitably, the dietary product may further comprise one or more macronutrients and/or one or more micronutrients.

The dietary product may further comprise methionine at a level of less than 25 mg/kg body weight of the subject/day or less than 20 mg/kg/day or less than 18 mg/kg/day or less than 16 mg/kg/day.

A dietary product of the invention may be formulated to provide at least the recommended daily intake of essential amino acids (with the optional exception of methionine) based on average daily total protein consumption.

The dietary product of the invention may be in the form of a solid, or a beverage.

The present invention further provides, a process of preparing a dietary product of the invention, wherein the components are dissolved or dispersed in water and spray dried.

In another aspect the present invention provides a pharmaceutical composition comprising a dietary product of the invention or a dietary product produced in accordance with the invention and a pharmaceutically acceptable carrier, excipient or diluent.

Suitably, the pharmaceutical composition of the invention may further comprise a therapeutic agent selected from: an inhibitor of cancer cell growth, a radiotherapeutic agent and a chemotherapeutic agent. The therapeutic agent may inhibit OXPHOS and/or may increase reactive oxygen species and/or may decrease anti-oxidant defence.

In a further aspect, the present invention provides a dietary product of the invention or produced in accordance with a process of the invention or a pharmaceutical composition of the invention for use in the treatment of cancer.

The cancer may be selected from the group consisting of: intestinal, colorectal, liver, lung, osteosarcoma, lymphoma, leukaemia and breast cancer.

The cancer may be positive for wild-type KRAS.

The cancer may have deregulated cMyc expression.

The dietary product may be substantially devoid of serine and/or glycine.

The cancer may be associated with a downregulation of MTAP expression and, optionally, the dietary product may have a reduced level or be substantially devoid of cysteine.

Suitably, the dietary product for use in the treatment of cancer may be used in combination with a therapeutic agent selected from: an inhibitor of cancer cell growth, a radiotherapeutic agent, a chemotherapeutic agent, an inhibitor of amino acid metabolism/turnover/inter-conversion, an inhibitor of non-essential amino acid biosynthesis, an inhibitor of amino acid transport, an enzyme or drug which promotes amino acid degradation or substance which sequesters amino acid(s).

The therapeutic agent may inhibit OXPHOS and/or may increase reactive oxygen species and/or may decrease anti-oxidant defence.

In another aspect, the present invention provides the use of dietary product of the invention or a dietary product produced in accordance with the invention or a pharmaceutical composition of the invention in the manufacture of a medicament for use the treatment of cancer.

Suitably, the cancer may be selected from the group consisting of: colorectal, lymphoma, liver, lung, osteosarcoma and breast cancer.

The cancer may be positive for wild-type KRAS and/or the cancer may have deregulated cMyc expression and/or downregulated MTAP expression.

Suitably, the dietary product of the invention may be substantially devoid of serine, glycine or serine and glycine.

Suitably, the dietary product of the invention may have a reduced level or may be substantially devoid of cysteine.

Suitably, the dietary product may be used in combination with one or more therapeutic agent(s) selected from: an inhibitor of cancer cell growth, a radiotherapeutic agent and a chemotherapeutic agent.

The therapeutic agent may inhibit OXPHOS and/or may increase reactive oxygen species and/or may decrease anti-oxidant defence.

In another aspect, the present invention relates to a method of treating cancer in a subject, comprising administering a therapeutically effective amount of a dietary product of the invention or a dietary product produced in accordance with the invention or a pharmaceutical composition of the invention.

Suitably, the cancer may be selected from the group consisting of: colorectal, liver, osteosarcoma, lung, lymphoma and breast cancer.

The cancer may be positive for wild-type KRAS and/or may have deregulated cMyc expression.

The dietary product may be substantially devoid of serine and/or glycine.

The dietary product may be used in combination with one or more therapeutic agent(s) selected from: an inhibitor of cancer cell growth, a radiotherapeutic agent and a chemotherapeutic agent.

The therapeutic agent may inhibit OXPHOS and/or may increase reactive oxygen species and/or may decrease anti-oxidant defence.

Suitably, in all aspects of the invention, the dietary product may be the sole source of nutrition for the subject.

The treatment is administered over a period of at least 24 hours or until a therapeutic endpoint is observed.

The dietary product may be administered between 1 and 6 times a day.

Suitably, at least the recommended daily amount of essential amino acids may be met by the administration regimen each day.

The present invention further provides the use of KRAS and/or MTAP as a biomarker to identify a patient or patient population responsive to or sensitive to a cancer treatment comprising a diet substantially devoid of serine and/or glycine.

Suitably, the cancer treatment may comprise a diet substantially devoid of serine and glycine.

Suitably, the cancer treatment may further comprise administration of a therapeutic agent selected from: an inhibitor of cancer cell growth, a radiotherapeutic agent and/or a chemotherapeutic agent.

In another aspect, the present invention provides a method of identifying a subject having a decreased likelihood of responsiveness or sensitivity to a cancer treatment comprising a diet substantially devoid of serine comprising:
  a) determining the level of Kras expression or activity in a biological sample isolated from the subject;
  b) comparing the level of Kras expression or activity in the biological sample to a control sample or to a predetermined reference level of Kras expression or activity,
  wherein an increased level of Kras expression or activity the biological sample compared to the control sample or compared to the predetermined reference level is indicative of non-responsiveness or insensitivity to said cancer treatment.

In a further aspect, the present invention provides a method of identifying a subject having an increased likelihood of responsiveness or sensitivity to a cancer treatment comprising a diet substantially devoid of serine comprising:

a) determining the level of Kras expression or activity in a biological sample isolated from the subject;
b) comparing the level of Kras expression or activity in the biological sample to a control sample or to a predetermined reference level of Kras expression or activity, wherein an decreased level of Kras expression or activity in the biological sample compared to the control sample or compared to the predetermined reference level, or a level of Kras expression or activity which is substantially the same as the control sample or the predetermined reference level is indicative of responsiveness or sensitivity to said cancer treatment.

In another aspect, the present invention provides a method of identifying a subject who may benefit from a cancer treatment comprising a diet substantially devoid of serine comprising:
a) determining the level of Kras expression or activity in a biological sample isolated from the subject;
b) comparing the level of Kras expression or activity in the biological sample to a control sample or to a predetermined reference level of Kras expression or activity, wherein an decreased level of Kras expression or activity in the biological sample compared to the control sample or compared to the predetermined reference level, or a level of Kras expression or activity which is substantially the same as the control sample or the predetermined reference level indicates that the patient may benefit from said cancer treatment.

In a further aspect, the present invention provides a method of identifying a subject having an increased likelihood of responsiveness or sensitivity to a cancer treatment comprising a diet i) substantially devoid of serine and/or ii) and/or ii) with a restricted level of cysteine comprising:
a) determining the level of MTAP expression or activity in a biological sample isolated from the subject;
b) comparing the level of MTAP expression or activity in the biological sample to a control sample or to a predetermined reference level of MTAP expression or activity, wherein an decreased level of MTAP expression or activity in the biological sample compared to the control sample or compared to the predetermined reference level, or a level of MTAP expression or activity which is substantially the same as the control sample or the predetermined reference level is indicative of responsiveness or sensitivity to said cancer treatment.

In another aspect, the present invention provides a method of identifying a subject who may benefit from a cancer treatment comprising a diet: i) substantially devoid of serine and/or ii) with a restricted level of cysteine comprising:
a) determining the level of MTAP expression or activity in a biological sample isolated from the subject;
b) comparing the level of MTAP expression or activity in the biological sample to a control sample or to a predetermined reference level of MTAP expression or activity, wherein an decreased level of MTAP expression or activity in the biological sample compared to the control sample or compared to the predetermined reference level, or a level of MTAP expression or activity which is substantially the same as the control sample or the predetermined reference level indicates that the patient may benefit from said cancer treatment. Suitably, in all aspects, in the biological sample may be a cancer cell or cancerous tissue. Likewise, in all aspects, the control sample may be a normal cell or tissue sample. The normal cell or tissue sample may be of the same cell or tissue type as the cancer cell or cancerous tissue.

In a further aspect, the present invention provides a method of treating a subject having a cancer comprising:
a) determining if the level of Kras expression or activity in a biological sample isolated from the subject is indicative of responsiveness or sensitivity to a cancer treatment comprising a diet substantially devoid of serine; and
b) administering to the subject the cancer treatment, where the level of Kras expression or activity in the biological sample is indicative of responsiveness or sensitivity to said cancer treatment.

In a further aspect, the present invention provides a method of treating a subject having a cancer comprising:
a) determining if the level of MTAP expression or activity in a biological sample isolated from the subject is indicative of responsiveness or sensitivity to a cancer treatment comprising a diet i) substantially devoid of serine and/or ii) restricted in cysteine; and
b) administering to the subject the cancer treatment, where the level of MTAP expression or activity in the biological sample is indicative of responsiveness or sensitivity to said cancer treatment.

Suitably, said cancer treatment may comprise a diet substantially devoid of serine and glycine.

Suitably, said cancer treatment may further comprise administration of a therapeutic agent selected from: an inhibitor of cancer cell growth, a radiotherapeutic agent and/or a chemotherapeutic agent.

Determining if the level of Kras expression or activity in a biological sample isolated from the subject is indicative of responsiveness or sensitivity to a cancer treatment comprising a diet substantially devoid of serine may comprise:
a) determining the level of Kras expression or activity in a biological sample isolated from the subject;
b) comparing the level of Kras expression or activity in the biological sample to a control sample or to a predetermined reference level of Kras expression or activity, wherein an increased level of Kras expression or activity in the biological sample compared to a control sample or compared to a predetermined reference level is indicative of non-responsiveness or insensitivity to the subject to said cancer treatment, and wherein an decreased level of Kras expression or activity in the biological sample compared to a control sample or compared to a predetermined reference level, or a level of Kras expression or activity which is substantially the same as a control sample or a predetermined reference level, is indicative of responsiveness or sensitivity of the subject to said cancer treatment.

Determining if the level of MTAP expression or activity in a biological sample isolated from the subject is indicative of responsiveness or sensitivity to a cancer treatment comprising: i) a diet substantially devoid of serine, and/or ii) a diet restricted in cysteine may comprise:
a) determining the level of MTAP expression or activity in a biological sample isolated from the subject;
b) comparing the level of MTAP expression or activity in the biological sample to a control sample or to a predetermined reference level of Kras expression or activity, wherein an decreased level of MTAP expression or activity in the biological sample compared to a control sample or compared to a predetermined reference level, or a level of MTAP expression or activity which is substantially the same as a control sample or a predetermined reference level, is indicative of increased responsiveness or sensitivity of the subject to said cancer treatment.

In another aspect, the present invention provides a kit for use in identifying a subject who would benefit from a cancer treatment comprising a diet substantially devoid of serine and/or glycine comprising:
  a. an agent for determining the expression or activity of Kras; and
  b. reagents for the assay.

Suitably, the kit may further comprise an agent for determining the expression or activity of MTAP.

The kit may further comprise instructions that an increased level of Kras expression or activity in a biological sample compared to a control sample or compared to a predetermined reference level is indicative of non-responsiveness or insensitivity of the subject to said cancer treatment, and wherein a decreased level of Kras expression or activity in the biological sample compared to the control sample or compared to a predetermined reference level, or a level of Kras expression or activity which is substantially the same as the control sample or the predetermined reference level, is indicative of responsiveness or sensitivity to the subject to said cancer treatment.

In another aspect, the present invention provides a kit for use in identifying a subject who would benefit from a cancer treatment comprising a diet: i) substantially devoid of serine and/or glycine; and/or ii) restricted in cysteine comprising:
  a. an agent for determining the expression or activity of MTAP; and
  b. reagents for the assay.

The kit may further comprise instructions that a decreased level of MTAP expression or activity in the biological sample compared to the control sample or compared to a predetermined reference level, or a level of MTAP expression or activity which is substantially the same as the control sample or the predetermined reference level, is indicative of responsiveness or sensitivity to the subject to said cancer treatment.

BRIEF DESCRIPTION OF THE DRAWINGS

Embodiments of the invention are further described hereinafter with reference to the accompanying drawings, in which.

DETAILED DESCRIPTION

Figure 1:
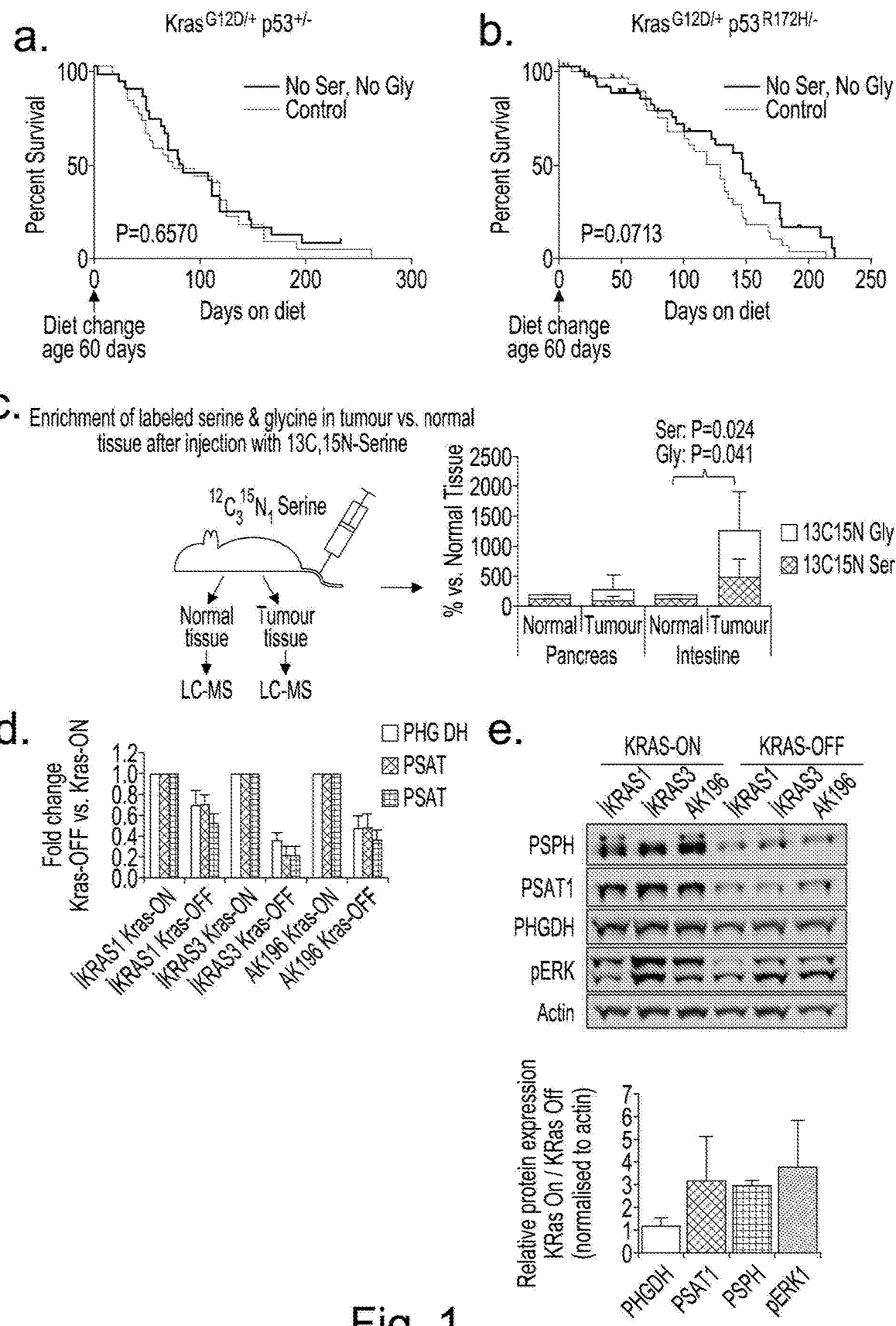
FIG. 1a. PDAC Kras G12D/+ p53+/−, and 1b. PDAC Kras G12D/+p53R172H/+: Mice placed on diet at ~60 days of age, taken until clinical end-point (PDAC related survival). Survival calculated from change of diet (not birth). P value calculated using mantel-cox test.
FIG. 1c. Mice were injected in the tail vein with 100 μl of 100 μM $^{13}C_3$ $^{15}N_1$ serine and left for 2 h. After sacrifice tissues were frozen then homogenised in metabolite extraction buffer & quantified by LCMS. P values calculated using paired T-test.
FIG. 1d. Kras inducible cell lines (iKRAS1, iKRAS3 and AK196) were grown in complete medium with doxycycline (KRAS-ON) or without doxycycline (KRAS-OFF). mRNA expression of serine synthesis pathway enzymes was analysed by qRT-PCR. Error bars=SEM.
FIG. 1e. Three Kras inducible cell lines (iKRAS1, iKRAS3 and AK196) were grown for 3 days, protein expression was analysed by western blot. Relative changes of Kras-ON/Kras-OFF (measured by LiCor infra-red quantification) in expression of SSP and Phospho-ERK1 protein averaged across iKRAS1, iKRAS3 and AK196 cells; the quantified bands are those shown in the western blot. Error bars=STDEV.
FIG. 1f. Kras inducible cell lines were grown in medium either containing or lacking serine and glycine (+SG/−SG) and counted after 48 and 96 hours. Error bars=SEM.
Figure 1:
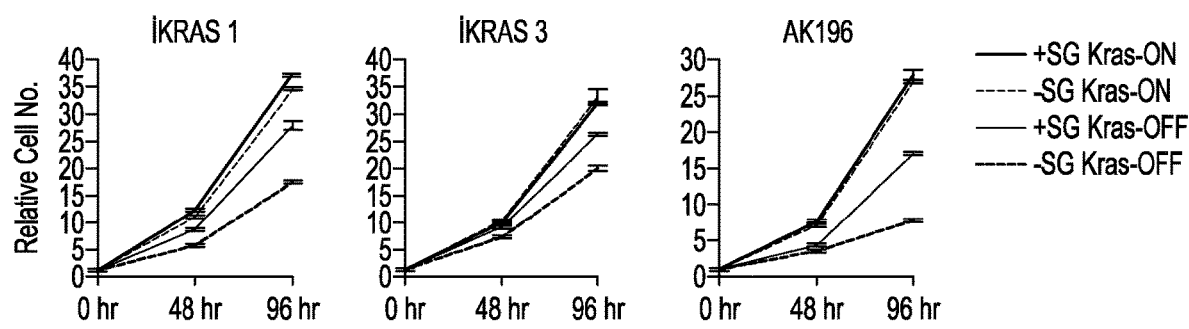
Figure 2:
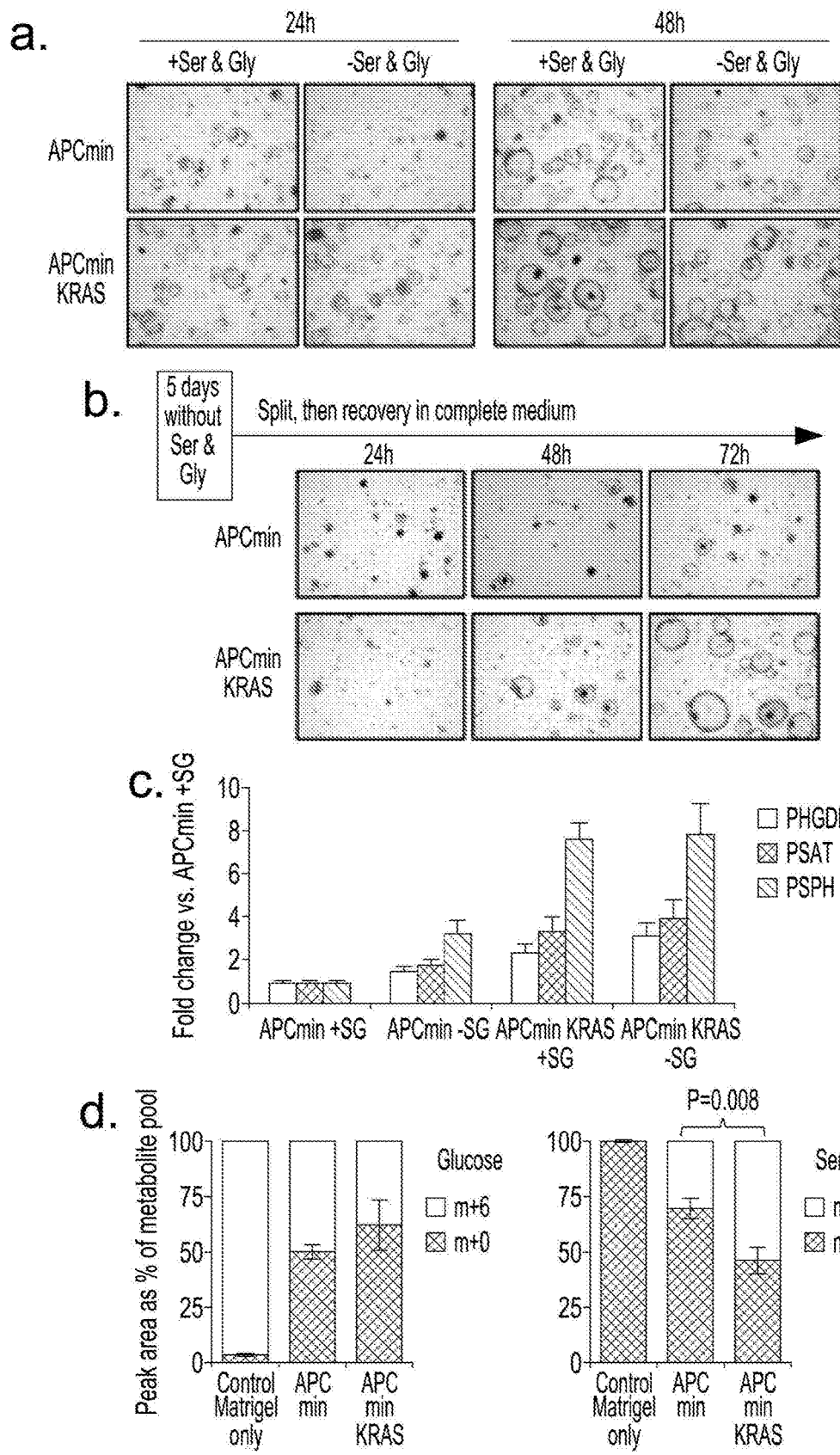
FIG. 2a. APCmin/APCmin KRAS organoids were grown with or without serine & glycine for 24-48 h.
FIG. 2b. APCmin/APCmin KRAS organoids grown without serine & glycine for 5 days then seeded into medium containing serine and glycine and grown for a further 24-72 h.
FIG. 2c. qRT-PCR on mRNA extracted from APCmin/APCmin KRAS organoids grown with or without serine & glycine.
FIG. 2d. APCmin/APCmin KRAS organoids grown in the presence of $^{13}C_6$-glucose for 5 hours, metabolites were extracted and analysed by LCMS. P values calculated using TTEST unpaired. Error bars=STDEV.
Figure 3:
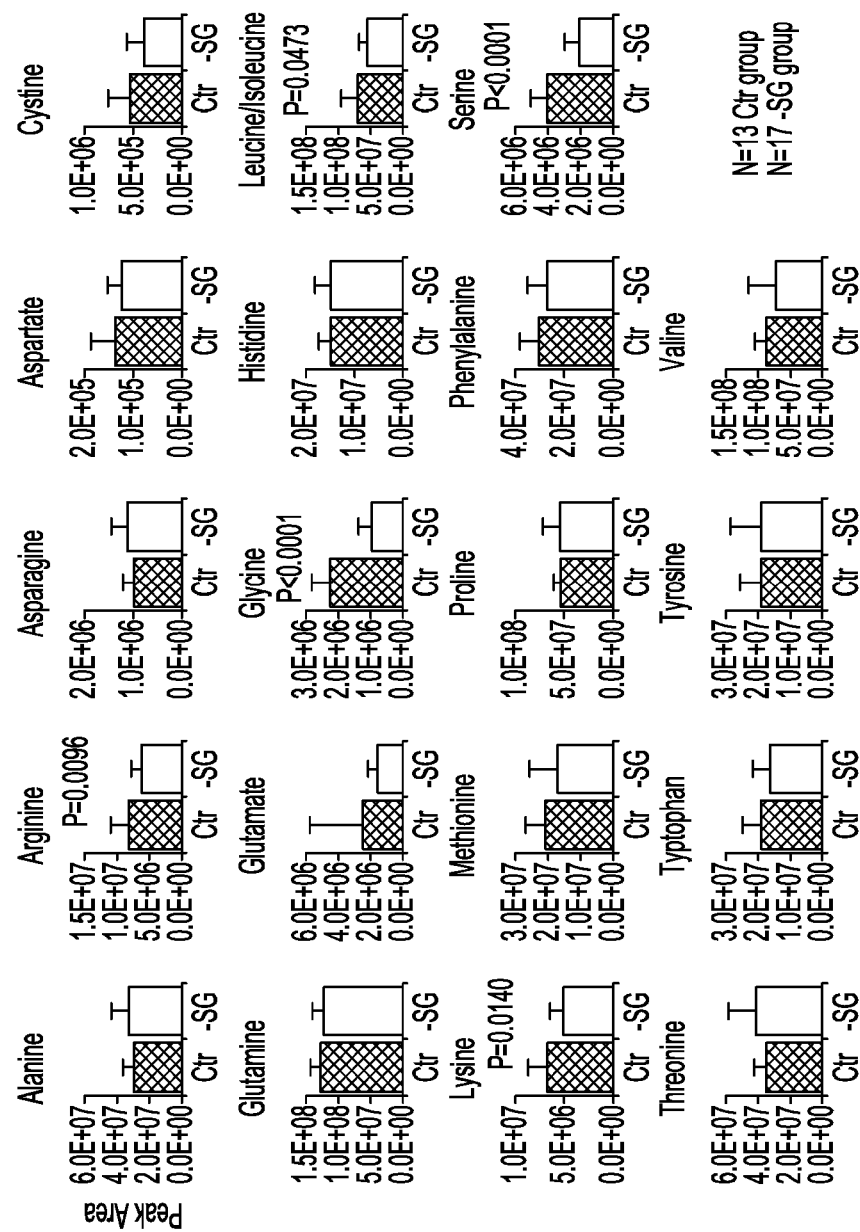
FIGS. 3a and 3b. Effect of serine/glycine free diet on serum amino acid levels in two mice models of pancreatic cancer measured by mass spec analysis of serum samples. Statistical comparisons detailed in figure. a. Pdx1$^{cre}$; KRas$^{G12D/+}$; p53$^{+/−}$ mice received normal chow until 60 days of age, then were transferred to either a control diet containing serine and glycine (Ctr) or a matched diet lacking serine and glycine (−SG) until clinical end-point. Serum isolated from terminal bleeds was analysed by LCMS. Relative quantity of metabolites are shown (x-axis=peak area). Error bars=STDEV. P values were calculated for each amino acid by T-test (unpaired, two tails), P values below 0.05 are shown. b. Pdx1$^{cre}$; KRas$^{G12D/+}$; p53$^{R172H/+}$ mice received control or SG-free (−SG) diet at 60 days of age until clinical end-point. Serum isolated from terminal bleeds was analysed by LCMS. Relative quantity of metabolites are shown (x-axis=peak area). Error bars=STDEV. P values were calculated for each amino acid by T-test (unpaired, two tails), P values below 0.05 are shown.
Figure 3:
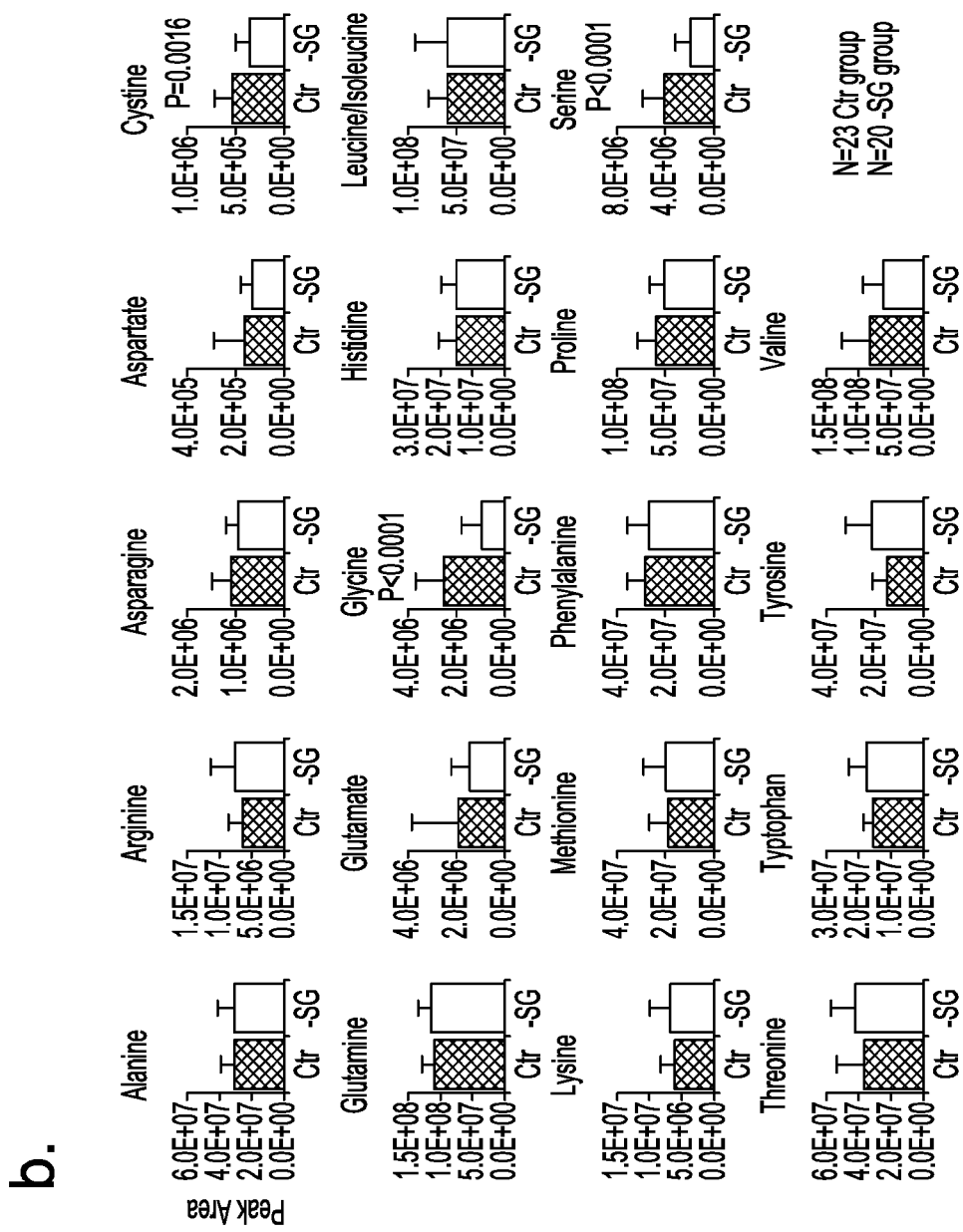
Figure 4:
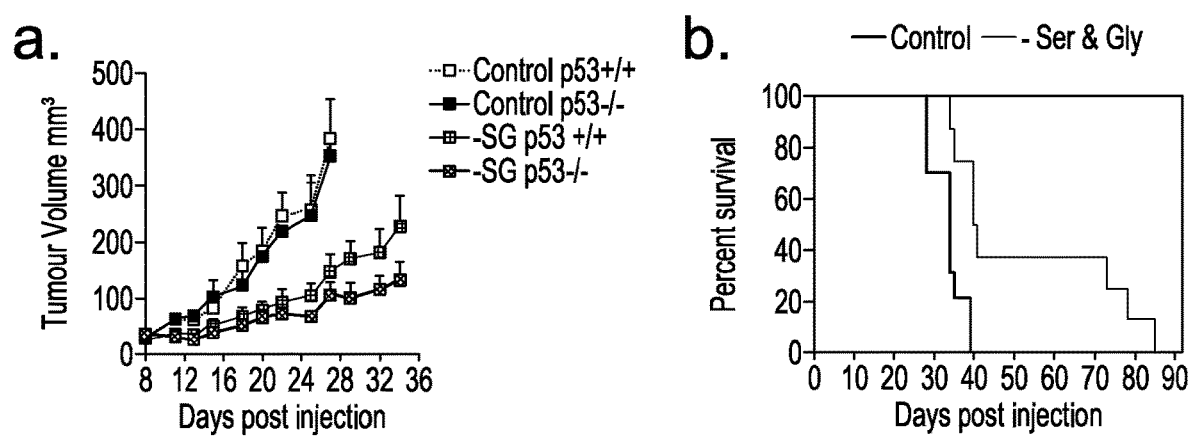
FIG. 4a. Growth rate of tumours formed from HCT116 cells (human colorectal cancer, either p53 wt or null). Tumours grew rapidly in mice fed a control diet, but a serine and glycine free diet (−SG) significantly attenuated tumour growth. b. The survival rate of the mice from the experiment shown in FIG. 4a. The serine free diet significantly improved the survival of the mice.

The inventors have surprisingly found that a diet substantially devoid of at least two non-essential amino acids can have utility in the treatment of cancer or a proliferative disorder. Without wishing to be bound by theory, by substantially removing an amino acid required for tumour cell proliferation and growth, metabolic remodelling to provide a source of the substantially devoid amino acid diverts resources and can reduce the amount of the amino acid available for rapid proliferation, thereby slowing down, or even inhibiting, the growth of, or causing the death of cancer cells.

Suitably, the present invention may involve partly or completely substituting the normal diet of a subject suffering from cancer with a prescribed diet substantially devoid of at least two non-essential amino acids. Such a diet may potentially be achieved by the provision of a dietary product as detailed herein, or by two or more dietary supplements which can be administered simultaneously or sequentially. Potentially, such a diet may be further supplemented through proper foods selection, using ingredients currently available such that the diet remains substantially devoid of two or more non-essential amino acids.

Dietary Product

In a first aspect of the present invention, there is provided a dietary product comprising a plurality of amino acids, wherein the dietary product comprises all the essential amino acids and wherein the dietary product is substantially devoid of at least two non-essential amino acids.

By "essential amino acids" it is meant methionine, leucine, phenylalanine, isoleucine, valine, lysine, threonine, histidine and tryptophan.

"Dietary product" refers to a composition comprising one or more essential amino acids or salts or esters thereof, that is used in a food product, or used or consumed in combination with a food product, to provide a desired level of the amino acid(s) or salt or esters thereof to the subject consuming the supplement. The dietary ingredients in these products may include: vitamins, minerals, herbs or other botanicals, amino acids, and substances such as enzymes, organ tissues, glandulars, and metabolites. In some embodiments, the dietary product is the sole source of exogenous amino acids consumed by the subject as part of their diet. Suitably, in some aspects, the dietary product may be intended to substantially or solely replace a subject's diet. Hence, in some aspects, the dietary product may be a complete meal replacement for the subject.

Advantageously, replacement of consumption of usual sources of amino acids such as protein with a dietary product of the invention will yield a diet substantially devoid of at least two non-essential amino acids. This may provide therapeutically benefits to a cancer subject.

As used herein, in accordance with all aspects of the invention, the term "subject" preferably refers to a mammalian animal, including a human, a veterinary or farm animal, a domestic animal or pet, and animals normally used for clinical research, including non-human primates, dogs and mice. More specifically, the subject of the present invention may be a human.

Suitably, the dietary product may comprise at least 9 amino acids. Suitably, the dietary product may comprise at least 10 or at least 11 or at least 12 or at least 13 or at least 14 or at least 15 or at least 16 or at least 17 or 18 amino acids. Suitably, the dietary product may comprise 9 to 18 amino acids or 12-18 amino acids, or 12-17 amino acids or 13-17 amino acids or 14-17 amino acids, for example.

Suitably, the at least two substantially devoid amino acids comprise (or consist essentially thereof or consist of) two or more of the following amino acids: glycine, serine, cysteine, tyrosine, proline and arginine. Alternatively, the dietary product may be devoid of at least three or at least four or at least five or at least six or at least seven of the following amino acids: glycine, serine, cysteine, tyrosine, proline, arginine, alanine, aspartic acid, glutamic acid, glutamine and asparagine. Suitably, the dietary product may be devoid of seven amino acids, wherein the dietary product is devoid of serine and glycine and five of the following amino acids: cysteine, tyrosine, proline, arginine, alanine, aspartic acid, glutamic acid, glutamine and asparagine. Suitably the dietary may be substantially devoid or may comprise a restricted level of cysteine.

In this context, by "consist essentially thereof" it is meant that that the dietary product may not lack further amino acids which have a material effect on the dietary product on the invention. By "material effect" it is meant a significant therapeutic effect which may be measured as one of the following: a) a significant effect on the specificity for cancer as opposed to healthy cells; b) a significant effect on the inhibition of cell proliferation; c) a significant effect on the toxicity of cancer cells or d) any combination of a)-c). In some aspects, this may be measured by comparing the dietary product with and without a particular amino acid and determining whether the lack of the amino acid has a material effect.

1. Method for Measuring the Effect of Amino Acid Starvation on Cell Proliferation In Vitro:

Cells are seeded into multiple replicate 24-well cell culture plates at a density of $1 \times 10^4$ to $1 \times 10^5$ cells per well in complete medium and allowed to adhere overnight. After overnight adherence cells should be 5-20% confluent. Cells are washed once with PBS and receive various cell culture media specifically formulated to contain or lack a specific amino acid/amino acids, including a control medium which contains all amino acids. The medium is replaced with fresh matched medium every 24 hours. At multiple time-points after the initial medium change (e.g. 1 day, 2 days, 3 days, 4 days and 5 days) plates are used for cell counts. At least three wells (i.e. triplicate) per condition should be used and average calculated. Cells are counted using a Casy TT cell counter, or by fixing cells, staining with DAPI and counting with an Operetta scanner. Cell numbers under the different amino acid conditions at the different time-points will be compared. A significant effect due to changed amino acid composition of the medium is deemed as greater than 5% change in cell number compared with the control medium, which is statistically significant when compared by appropriate TTEST (where $P<0.05$ qualifies as significant effect) over at least three independent experiments.

2. Methods for Measuring Effect of Amino Acid Composition of Diet on Cancer Cell Proliferation/Tumour Growth & Survival In Vivo Using Mouse Xenograft/Allograft/Orthotopic Models An appropriate cancer cell line should be selected which forms tumours when grafted sub-cutaneously into flanks of nude mice (e.g. HCT116). An appropriate number of cells to form a tumour (e.g. $3 \times 10^6$) are injected sub-cutaneously into the mouse flanks. At least 10 mice per group should be used, either with both flanks injected or single flanks. The same day as the mice are injected they should be transferred from normal chow onto experimental diets which are specifically formulated to lack a specific amino acid/amino acids. A control group which receive a diet containing all amino acids should be included. Tumour length and width are measured at least twice per week until death and used to calculate tumour volume. Mice should be allowed to live until clinical endpoint where a pre-determined maximal tumour volume (allowed by local ethics) is reached then culled. The average tumour volume at each time-point of measurement before the first mouse dies/is culled should be compared. A significant effect on tumour volume is assessed by an appropriate TTEST, where $P<0.05$ qualifies as significant effect. A significant change in survival is calculated using a Mantel-Cox (log rank) statistical test, where $P<0.05$ qualifies as significant effect.

Alternatively, the above assay can be performed where mice are kept on a normal chow diet after injection with grafted cells and only assigned to the experimental diets once measurable tumours are detected. In this case tumour volume can be compared either as absolute volume, or as a percentage of starting tumour volume at time of diet change.

Alternatively an allograft or orthotopic model can be used in the same way as described above.

3. Methods for Measuring Effect of Amino Acid Composition of Diet on Cancer Cell Proliferation/Tumour Growth & Survival In Vivo Using Genetically Engineered Mouse Models (GEMMs)

An appropriate GEMM should be selected (e.g. APC$^{min/+}$ or Eμ-myc); mice should be fed normal chow until diet change. Age at diet change should be later in life (once tumour initiation has occurred) but before death due to clinical end-point (tumour related survival) has occurred. E.g. 80 days in APC$^{min/+}$ mice and 60 days in Eμ-myc mice. At the specified age mice should be transferred from normal chow onto experimental diets which are specifically formulated to lack a specific amino acid/amino acids. A control group, which receive a diet containing all amino acids should be included. If possible tumour growth should be measured (e.g. by tumour measurement, or by biomarker analysis e.g. fluorescent signal from fluorescent protein marker in tumour), and mice allowed to reach clinical end-point (tumour related survival). At this time tumour burden should also be assessed (e.g. by counting/weighing/measuring tumours). The average tumour volume at each time-point of measurement before the first mouse dies/is culled should be compared. A significant effect on tumour volume is assessed by an appropriate TTEST, where $P<0.05$ qualifies as significant effect. A significant change in survival is calculated using a Mantel-Cox (log rank) statistical test, where $P<0.05$ qualifies as significant effect. For end-point tumour burden a significant effect on tumour burden is assessed by an appropriate TTEST, where $P<0.05$ qualifies as significant effect.

Alternatively the diet can be changed earlier in life, e.g. 10 days/20 days/40 days, and the same outcomes described above (3) are measured and compared.

Suitably, the dietary product may be substantially devoid of serine. Cancer cells may rapidly utilise large amounts of exogenous serine to support their rapid proliferation. When serine is depleted cancer cells are forced to channel glycolytic intermediates through the serine synthesis pathway. Advantageously, this may result in reduced proliferation and/or reduced cell survival.

Suitably, the dietary product may be substantially devoid of glycine. This may reduce blood levels of both glycine and serine, as serine is utilised to synthesise glycine. Advantageously, the present invention has shown that a diet substantially devoid of both serine and glycine may be particularly effective.

Suitably, the dietary product may be substantially devoid of cysteine. The present invention has surprisingly shown that numerous cancer cell lines (such as lung, colorectal and breast) avidly consume exogenous cysteine. Surprisingly, a diet substantially devoid of cysteine may inhibit cell growth and may cause cancer cell death as shown in colorectal cell lines, for example. Suitably, a dietary product substantially devoid of cysteine or having a restricted level of cysteine may be particularly effective for a subject having downregulated expression of MTAP.

Suitably, the dietary product may be substantially devoid of tyrosine. The present invention has surprisingly found that restriction of tyrosine can reduce cancer cell growth either alone or in combination with other non-essential amino acids.

Suitably, the dietary product is substantially devoid of:
a. Glycine, serine and cysteine;
b. Glycine serine and arginine;
c. Glycine serine and tyrosine;
d. Glycine, serine, arginine and cysteine;
e. Glycine, serine, tyrosine and cysteine;
f. Cysteine and arginine;
g. Cysteine and tyrosine;
h. Cysteine and glycine;
i. Cysteine, tyrosine and arginine; or
j. Glycine, serine, arginine, tyrosine and cysteine.

Advantageously, the present invention has surprisingly shown that such combinations are particularly effective at inhibiting cell proliferation and/or inducing cancer cell death.

In one aspect, the dietary product is substantially devoid of glycine, serine and cysteine. This combination has been shown by the present invention to be surprisingly effective in inhibiting cancer cell proliferation and increasing cancer cell death in numerous cancer cell lines including colorectal (such as in HCT116 and RKO), liver (HepG2), osteosarcoma (U2OS) and breast (MDA MB 231) cancer, for example.

In one aspect, the dietary product is substantially devoid of glycine, serine and arginine. This combination has been shown by the present invention to be surprisingly effective in inhibiting cancer cell proliferation and/or increasing cancer cell death in colorectal cells lines (such as RKO and HCT116).

In one aspect, the dietary product is substantially devoid of glycine, serine and tyrosine. This combination has been shown by the present invention to be surprisingly effective in inhibiting cancer cell proliferation and/or increasing cancer cell death in colorectal cells lines (such as RKO and HCT116).

In one aspect, the dietary product is substantially devoid of glycine, serine, arginine and cysteine. Surprisingly, this combination has been shown to be particular effective in inducing cell death in a colorectal cell line.

In one aspect, the dietary composition may be substantially devoid of glycine, serine, arginine, tyrosine and cysteine.

Suitably, in all aspects, the dietary product may comprise any one of or any combination of: methionine, glutamine and leucine. Advantageously, leucine and glutamine.

The dietary product may further comprises methionine at a level of less than 25 mg/kg body weight of the subject/day or less than 20 mg/kg/day or less than 18 mg/kg/day or less than 16 mg/kg/day.

A dietary product of the invention may be formulated to provide at least the recommended daily intake of essential amino acids based on average daily total protein consumption, unless otherwise stated herein.

The recommended daily intake of essential amino acids by the Institute of Medicine, as based on average daily total protein consumption, is: Histidine 18 mg/g protein consumed; isoleucine 25 mg/g protein; leucine 55 mg/g protein, lysine 51 mg/g protein, methionine and cysteine combined 25 mg/g protein; phenylalanine and tyrosine combined 47 mg/g protein, threonine 27 mg/g protein, tryptophan 7 mg/g protein and valine 32 mg/g protein. Tyrosine and cysteine are non-essential amino acids. Where a dietary product of the invention is substantially devoid of either tyrosine and/or cysteine, the dietary product is formulated to provide levels of phenylalanine and methionine in the dietary product will be adjusted such that the dietary product is formulated to provide methionine in an amount of at least 25 mg/g protein and phenylalanine in an amount of at least 47 mg/g protein based on average daily protein consumption.

Suitably, a dietary product "restricted" in cysteine is one which provides less that is formulated to provide less than the recommended daily intake of cysteine based on average daily protein consumption. For example, dietary product restricted in cysteine is may be one which provides less than 20 mg/g protein or less than 15 mg/g protein or less than 10 mg/g protein or less than 5 mg/g protein.

Suitably, the dietary product may be formulated to provide a restricted level of total non-essential amino acids per gram of protein consumption. For example, the combined daily intake of non-essential amino acids may be equivalent to the diet being substantially devoid of at least one or at least two or at least three or at least four of at least five or at least six or at least seven non-essential amino acids compared with the recommended daily intake of total non-essential amino acids per gram of protein consumed.

The institute of medicine recommends that protein is consumed at a rate of 0.8 grams per kilogram per day of body weight for adults for example. The dietary product may be formulated to provide at least 0.8 grams protein per kg body weight during recommended daily consumption of the product.

Suitably, the dietary product of the invention may be formulated to provide these above recommended levels. For example, one or more amino acids may be formulated in the dietary product to provide at least 2, 3, 4, 5, or 6 times the daily average intake based on average daily total protein consumption.

Suitably, the amino acids present in the dietary product of the invention may be amino acids in free form, in prodrug form, salts or amino acid esters. Amino acids with one or more N-terminal or C-terminal modification, and homopolymer, homodimer, heteropolymer and heterodimer forms may also be contemplated.

Suitably, the dietary product may be formulated to be administered from once to eight times daily. Preferably, once to four times daily. Thus, the dietary product may be formulated to an appropriate unit dosage form.

The dietary product of the invention may further comprise one or more macronutrients and/or micronutrients.

Guidance on macronutrients and suggested recommended daily amounts may be found in the Dietary Reference Intakes for Energy, Carbohydrate, Fiber, Fat, Fatty Acids, cholesterol, protein and amino acids released by the Institute of Medicine September 2002.

A non-exhaustive list of macronutrients which may be additional components of the dietary product include: carbohydrate, fiber and fat (such as n-6 polyunsaturated fatty acids, n-3 polyunsaturated fatty acids, saturated and trans fatty acids and cholesterol).

A non-exhaustive list of micronutrients includes Vitamin A, Vitamin C, Vitamin D, Vitamin E, Vitamin K, Thiamin, Riboflavin, Niacin, Vitamin B6, folate, Vitamin B12, Pantothenic acid, biotin, choline, calcium, chromium, copper, fluoride, iodine, iron, magnesium, molybedenum, phosphorus, selenium, zinc, potassium, sodium, and chloride. Suitably the dietary product may be formulated to provide these in acceptable or recommended daily intake amounts as detailed in the publication "Dietary Reference Intakes: RDA and AI for Vitamins and Elements", NAS. IOM. Food and Nutrition Board.

The diets contain an imbalance of amino acids generally in the form of a deficiency of two or more non-essential amino acids, optionally complemented by a surplus of one or more other amino acids. For example, a substantially devoid amino acid may be at least 10, 15, 20, 30, 45, 50, 100, or 1000 times lower than the average abundance of the other amino acids. Foods that are low in protein but rich in other nutrients, such as fruits, vegetables and certain nuts can be consumed following a dietician's recommendation, making sure the dietary amino acid intake ratios are kept at the intended ratios. This diet is intended to be consumed alone or in combination with drug therapies, such as those that have anti-cancer activity.

In some embodiments, the dietary product of the invention is formulated across two or more dietary supplements which together provide a dietary product of the invention. These may be administered simultaneously or sequentially to said subject, such that the combined average diet provided by the dietary supplements provides a dietary product of the invention. This may be advantageous to add variety to the subject's diet.

Dietary products may be provided in the form of a powder, a gel, a solution, a suspension, a paste, a solid, a liquid, a liquid concentrate, a powder which may be reconstituted, a shake, a concentrate, a pill, a bar, a tablet, a capsule or a ready-to-use product. It is contemplated that a dietary product can also be a pharmaceutical composition when the supplement is in the form of a tablet, pill, capsule, liquid, aerosol, injectable solution, or other pharmaceutically acceptable formulation. Suitably, the dietary product may be a beverage. Suitably, the beverage may be administered 2 to 6 times a day.

Suitably, the dietary product may not be a naturally occurring food.

Suitably, the dietary product may comprise additional compounds to the specified amino acids. Suitably such additional compounds may not aid de novo synthesis of the substantially devoid amino acids.

As used herein "substantially devoid" in reference to an amino acid means completely or very nearly free (such as trace amounts) of that amino acid.

Optionally, administration will be by the intravenous route. Optionally, parenteral administration may be provided in a bolus or by infusion.

Suitably, the dietary product may be:
a) A tube fed enteral nutritional product (such as a naso-gastric nutritional product, which may be administered via a NG tube; a naso-jejunal nutritional product, which may be administered via a NJ tube; or a PEG (percutaneous endoscopic gastrostomy) tube nutritional product);
b) a parenteral nutrition product (which may be administered by central venous administration, e.g. via dedicated lumen on a venous catheter); or
c) an IV infusion product.

Preferably the administration may be via tube-fed enteral nutrition.

In certain embodiments, the diet or dietary product of the invention is administered over a time period of at least 1 day, 2 days, 3 days, 4 days, 5 days, 6 days, 7 days, at least 2 weeks, 3 weeks, 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, or until a therapeutic endpoint is observed, e.g., tumor shrinkage is observed.

The present invention further provides a process of preparing a dietary product of the invention, wherein the amino acids are dissolved or dispersed in water and spray dried.

Suitably, the amino acids may be mixed with additional components such as macronutrients and micronutrients. Binders, emulsifiers or other ingredients suitable for human or animal consumption may be added as desired.

Pharmaceutical Composition

In another aspect, the present invention provides a pharmaceutical composition comprising a dietary product of the invention or a dietary product produced in accordance with the invention and a pharmaceutically acceptable carrier, excipient or diluent.

Conventional procedures for the selection and preparation of suitable pharmaceutical formulations are described in, for example, "Pharmaceuticals—The Science of Dosage Form Designs", M. E. Aulton, Churchill Livingstone, 1988.

The compositions of the invention may be in a form suitable for oral use (for example as tablets, lozenges, hard or soft capsules, aqueous or oily suspensions, emulsions, dispersible powders or granules, syrups or elixirs).

The compositions of the invention may be obtained by conventional procedures using conventional pharmaceutical excipients, well known in the art. Thus, compositions intended for oral use may contain, for example, one or more colouring, sweetening, flavouring and/or preservative agents.

Suitably, the pharmaceutical composition is formulated to provide a therapeutically effective amount of the dietary product of the invention.

An effective amount for use in therapy of a condition is an amount sufficient to symptomatically relieve in a warm-blooded animal, particularly a human the symptoms of the condition or to slow the progression of the condition.

The term "therapeutically effective amount" encompasses the amount of a compound or composition that, when administered, is sufficient to prevent development of, or alleviate to some extent, one or more of the symptoms of the condition, disorder or disease being treated. The term "therapeutically effective amount" also encompasses the amount of a compound or composition that is sufficient to elicit the biological or medical response of a cell, tissue, organ, system, animal or human, which is being sought by a researcher, medical doctor or clinician. An appropriate "effective" amount in any individual case may be determined by one of ordinary skill in the art using routine experimentation. It will be understood that the specific dose level and frequency of administration for any particular patient may be varied and will depend upon a variety of factors, including the activity of the specific compound employed; the bioavailability, metabolic stability, rate of excretion and length of action of that compound; the mode and time of administration of the compound; the age, body weight, general health, sex and diet of the patient; and the severity of the particular condition being treated.

The terms "treat", "treating" and "treatment" encompass alleviating or abrogating a condition, disorder or disease, or one or more of the symptoms associated with the condition, disorder or disease, and encompass alleviating or eradicating the cause(s) of the condition, disorder or disease itself. In certain embodiments, the terms "treat", "treating", and "treatment" refer to administration of a compound, a pharmaceutical composition or a pharmaceutical dosage form to a subject for the purpose of alleviating, abrogating or preventing a condition, disorder or disease, or symptom(s) associated therewith, or cause(s) thereof.

Suitably, the pharmaceutical composition of the invention may further comprise a therapeutic agent selected from: an inhibitor of cancer cell growth, a radiotherapeutic agent, a chemotherapeutic agent, an inhibitor of amino acid metabolism/turnover/inter-conversion, an inhibitor of non-essential amino acid biosynthesis, an inhibitor of amino acid transport, an enzyme or drug which promotes amino acid degradation or substance which sequesters amino acid(s). The therapeutic agent may inhibits OXPHOS and/or may increase reactive oxygen species and/or may decrease anti-oxidant defence.

Cancers and Proliferative Disorders

In one aspect, the present invention provides a dietary product of the invention or produced in accordance with a process of the invention or a pharmaceutical composition of the invention for use in a medicament.

For example, the present invention provides a dietary product of the invention or produced in accordance with a process of the invention or a pharmaceutical composition of the invention for use in the treatment of cancer.

In another aspect, the present invention provides the use of dietary product of the invention or a dietary product produced in accordance with the invention or a pharmaceutical composition of the invention in the manufacture of a medicament for use the treatment of cancer.

In a further aspect, the present invention provides a method of treating cancer in a subject, comprising administering a therapeutically effective amount of a dietary product to the subject.

For all aspects, exemplary cancers include, but are not limited to, adrenocortical carcinoma, AIDS-related cancers, AIDS-related lymphoma, anal cancer, anorectal cancer, cancer of the anal canal, appendix cancer, childhood cerebellar astrocytoma, childhood cerebral astrocytoma, basal cell carcinoma, skin cancer (non-melanoma), biliary cancer, extrahepatic bile duct cancer, intrahepatic bile duct cancer, bladder cancer, urinary bladder cancer, bone and joint cancer, osteosarcoma and malignant fibrous histiocytoma, brain cancer, brain tumor, brain stem glioma, cerebellar astrocytoma, cerebral astrocytoma/malignant glioma, ependymoma, medulloblastoma, supratentorial primitive neuroectodeimal tumors, visual pathway and hypothalamic glioma, breast cancer, bronchial adenomas/carcinoids, carcinoid tumor, gastrointestinal, nervous system cancer, nervous system lymphoma, central nervous system cancer, central nervous system lymphoma, cervical cancer, childhood cancers, chronic lymphocytic leukemia, chronic myelogenous leukemia, chronic myeloproliferative disorders, colon cancer, colorectal cancer, cutaneous T-cell lymphoma, lymphoid neoplasm, mycosis fungoides, Seziary Syndrome, endometrial cancer, esophageal cancer, extracranial germ cell tumor, extragonadal germ cell tumor, extrahepatic bile duct cancer, eye cancer, intraocular melanoma, retinoblastoma, gallbladder cancer, gastric (stomach) cancer, gastrointestinal carcinoid tumor, gastrointestinal stromal tumor (GIST), germ cell tumor, ovarian germ cell tumor, gestational trophoblastic tumor glioma, head and neck cancer, hepatocellular (liver) cancer, Hodgkin lymphoma, hypopharyngeal cancer, intraocular melanoma, ocular cancer, islet cell tumors (endocrine pancreas), Kaposi Sarcoma, kidney cancer, renal cancer, kidney cancer, laryngeal cancer, acute lymphoblastic leukemia, acute myeloid leukemia, chronic lymphocytic leukemia, chronic myelogenous leukemia, hairy cell leukemia, lip and oral cavity cancer, liver cancer, lung cancer, non-small cell lung cancer, small cell lung cancer, AIDS-related lymphoma, non-Hodgkin lymphoma, primary central nervous system lymphoma, Waldenstram macroglobulinemia, meduUoblastoma, melanoma, intraocular (eye) melanoma, merkel cell carcinoma, mesothelioma malignant, mesothelioma, metastatic squamous neck cancer, mouth cancer, cancer of the tongue, multiple endocrine neoplasia syndrome, mycosis fungoides, myelodysplasia syndromes, myelodysplastic/myeloproliferative diseases, chronic myelogenous leukemia, acute myeloid leukemia, multiple myeloma, chronic myeloproliferative disorders, nasopharyngeal cancer, neuroblastoma, oral cancer, oral cavity cancer, oropharyngeal cancer, ovarian cancer, ovarian epithelial cancer, ovarian low malignant potential tumor, pancreatic cancer, islet cell pancreatic cancer, paranasal sinus and nasal cavity cancer, parathyroid cancer, penile cancer, pharyngeal cancer, pheochromocytoma, pineoblastoma and supratentorial primitive neuroectodermal tumors, pituitary tumor, plasma cell neoplasm/multiple myeloma, pleuropulmonary blastoma, prostate cancer, rectal cancer, renal pelvis and ureter, transitional cell cancer, retinoblastoma, rhabdomyosarcoma, salivary gland cancer, ewing family of sarcoma tumors, Kaposi Sarcoma, soft tissue sarcoma, uterine cancer, uterine sarcoma, skin cancer (non-melanoma), skin cancer (melanoma), merkel cell skin carcinoma, small intestine cancer, soft tissue sarcoma, squamous cell carcinoma, stomach (gastric) cancer, supratentorial primitive neuroectodermal tumors, testicular cancer, throat cancer, thymoma, thymoma and thymic carcinoma, thyroid cancer, transitional cell cancer of the renal pelvis and ureter and other urinary organs, gestational trophoblastic tumor, urethral cancer, endometrial uterine cancer, uterine sarcoma, uterine corpus cancer, vaginal cancer, vulvar cancer, and Wilm's Tumor. In some embodiments, the cancer is selected from the group consisting of colorectal, liver, osteosarcoma, lymphoma and breast cancer and lymphoma.

The cancer may be positive for wild-type KRAS.

The cancer may have deregulated cMyc expression.

The cancer may be a tumour which may have downregulated MTAP expression. The tumour may be a solid tumour or a haematological malignancy.

Exemplary solid tumours include, but are not limited to, mesothelioma, lung cancer, non-small cell lung cancer (NSCLC), adenocarcinoma, squamous cell carcinoma, gliomas, pancreatic tumour, pancreatic cancer, ampullary cancer, biliary cancer, biliary tract cancer, soft tissue sarcoma, esophageal cancer, endometrial cancer, chondrosarcoma, osteosarcoma, gastrointestinal stromal tumour and chordoma, primary malignant melanoma, metastatic melanoma and primary breast cancer.

Exemplary hematologic malignancies include, but are not limited to, diffuse large cell lymphoma, low-grade lymphoma, B-lineage acute lymphocytic leukemia, mantle cell lymphoma, T-cell acute leukemia, adult T cell leukemia, lymphomas of T-cell origin. The lymphomas may optionally be transformed.

Suitably, the dietary products of the invention may have utility in treating diseases or disorders in which aberrant or otherwise undesired proliferation of cells can lead to a debilitating disorder.

The dietary product may be substantially devoid of cysteine. Suitably, a diet substantially devoid of cysteine may have utility in cancers which rely avidly consume exogenous cysteine such as lung, colorectal and breast cancer. Suitably, a diet substantially devoid of cysteine may have utility in cancers where there is a downregulated expression of MTAP.

The dietary product may be substantially devoid of serine and/or glycine. Suitably, a diet substantially devoid of serine and/or glycine may have utility in cancers which rely avidly consume exogenous serine and/or glycine such as lung, colorectal and breast cancer, lymphoma, colorectal cancer, liver cancer, osteosarcoma and breast cancer.

The dietary product may be substantially devoid of arginine and/or tyrosine. Suitably, a diet substantially devoid of arginine may have utility in cancers such as colorectal cancer.

Combination Therapy

The dietary products or pharmaceutical compositions of the invention may be used alone to provide a therapeutic effect. Suitably, the dietary products or pharmaceutical compositions of the invention may also be used in combination with one or more additional chemotherapeutic agent and/or radiotherapy.

Such chemotherapy may include one or more of the following categories of anti-cancer agents:

(i) antiproliferative/antineoplastic drugs and combinations thereof, such as alkylating agents (for example cis platin, oxaliplatin, carboplatin, cyclophosphamide, nitrogen mustard, uracil mustard, bendamustin, melphalan, chlorambucil, chlormethine, busulphan, temozolamide, nitrosoureas, ifosamide, melphalan, pipobroman, triethylene-melamine, triethylenethiophoporamine, carmustine, lomustine, stroptozocin and dacarbazine); antimetabolites (for example gemcitabine and antifolates such as fluoropyrimidines like 5 fluorouracil and tegafur, raltitrexed, methotrexate, pemetrexed, cytosine arabinoside, floxuridine, cytarabine, 6-mercaptopurine, 6-thioguanine, fludarabine phosphate, pentostatine, and gemcitabine and hydroxyurea); antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and taxotere and polokinase inhibitors); proteasome inhibitors, for example carfilzomib and bortezomib; interferon therapy; and topoisomerase inhibitors (for example epipodophyllotoxins like etoposide and teniposide, amsacrine, topotecan, irinotecan, mitoxantrone and camptothecin); bleomcin, dactinomycin, daunorubicin, doxorubicin, epirubicin, idarubicin, ara-C, paclitaxel (Taxol™), nabpaclitaxel, docetaxel, mithramycin, deoxyco-formycin, mitomycin-C, L-asparaginase, interferons (especially IFN-alpha), etoposide, teniposide, DNA-demethylating agents, (for example, azacitidine or decitabine); and histone de-acetylase (HDAC) inhibitors (for example vorinostat, MS-275, panobinostat, romidepsin, valproic acid, mocetinostat (MGCD0103) and pracinostat SB939);

(ii) cytostatic agents such as antiestrogens (for example tamoxifen, fulvestrant, toremifene, raloxifene, droloxifene and iodoxyfene), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5*-reductase such as finasteride; and navelbene, CPT-II, anastrazole, letrazole, capecitabine, reloxafme, cyclophosphamide, ifosamide, and droloxafine;

(iii) anti-invasion agents, for example dasatinib and bosutinib (SKI-606), and metalloproteinase inhibitors, inhibitors of urokinase plasminogen activator receptor function or antibodies to Heparanase;

(iv) inhibitors of growth factor function: for example such inhibitors include growth factor antibodies and growth factor receptor antibodies, for example the anti erbB2 antibody trastuzumab [Herceptin™], the anti-EGFR antibody panitumumab, the anti erbB1 antibody cetuximab, tyrosine kinase inhibitors, for example inhibitors of the epidermal growth factor family (for example EGFR family tyrosine kinase inhibitors such as gefitinib, erlotinib, 6-acrylamido-N-(3-chloro-4-fluorophenyl)-7-(3-morpholinopropoxy)-quinazolin-4-amine (CI 1033), afatinib, vandetanib, osimertinib and rociletinib) erbB2 tyrosine kinase inhibitors such as lapatinib) and antibodies to costimulatory molecules such as CTLA-4, 4-IBB and PD-I, or antibodies to cytokines (IL-10, TGF-beta); inhibitors of the hepatocyte growth factor family; inhibitors of the insulin growth factor family; modulators of protein regulators of cell apoptosis (for example Bcl-2 inhibitors); inhibitors of the platelet-derived growth factor family such as imatinib and/or nilotinib (AMN107); inhibitors of serine/threonine kinases (for example Ras/Raf signalling inhibitors such as farnesyl transferase inhibitors, sorafenib, tipifarnib and lonafarnib), inhibitors of cell signalling through MEK and/or AKT kinases, c-kit inhibitors, abl kinase inhibitors, PI3 kinase inhibitors, Plt3 kinase inhibitors, CSF-1R kinase inhibitors, IGF receptor, kinase inhibitors; aurora kinase inhibitors and cyclin dependent kinase inhibitors such as CDK2 and/or CDK4 inhibitors; CCR2, CCR4 or CCR6 antagonists; and RAF kinase inhibitors such as those described in WO2006043090, WO2009077766, WO2011092469 or WO2015075483.

(v) antiangiogenic agents such as those which inhibit the effects of vascular endothelial growth factor, [for example the anti-vascular endothelial cell growth factor antibody bevacizumab (Avastin™)]; thalidomide; lenalidomide; and for example, a VEGF receptor tyrosine kinase inhibitor such as vandetanib, vatalanib, sunitinib, axitinib and pazopanib;

(vi) gene therapy approaches, including for example approaches to replace aberrant genes such as aberrant p53 or aberrant BRCA1 or BRCA2;

(vii) immunotherapy approaches, including for example antibody therapy such as alemtuzumab, rituximab, ibritumomab tiuxetan (Zevalin®) and ofatumumab; interferons such as interferon α; interleukins such as IL-2 (aldesleukin); interleukin inhibitors for example IRAK4 inhibitors; cancer vaccines including prophylactic and treatment vaccines such as HPV vaccines, for example Gardasil, Cervarix, Oncophage and Sipuleucel-T (Provenge); gp100; dendritic cell-based vaccines (such as Ad.p53 DC); toll-like receptor modulators for example TLR-7 or TLR-9 agonists; PD-1, PD-L1, PD-L2 and CTL4-A modulators (for example Nivolumab), antibodies and vaccines; other IDO inhibitors (such as indoximod); anti-PD-1 monoclonal antibodies (such as MK-3475 and nivolumab); anti-PDL1 monoclonal antibodies (such as MEDI-4736 and RG-7446); anti-PDL2 monoclonal antibodies; and anti-CTLA-4 antibodies (such as ipilumumab); and (viii) cytotoxic agents for example fludaribine (fludara), cladribine, pentostatin (Nipent™);

(ix) targeted therapies, for example PI3K inhibitors, for example idelalisib and perifosine; SMAC (second mitochondriaderived activator of caspases) mimetics, also known as Inhibitor of Apoptosis Proteins (IAP) antagonists (IAP antagonists). These agents act to supress IAPs, for example XIAP, cIAP1 and cIAP2, and thereby re-establish cellular apoptotic pathways. Particular SMAC mimetics include Birinapant (TL32711, TetraLogic Pharmaceuticals), LCL161 (Novartis), AEG40730 (Aegera Therapeutics), SM-164 (University of Michigan), LBW242 (Novartis), ML101 (Sanford-Burnham Medical Research Institute), AT-406 (Ascenta Therapeutics/University of Michigan), GDC-0917 (Genentech), AEG35156 (Aegera Therapeutic), and HGS1029 (Human Genome Sciences); and agents which target ubiquitin proteasome system (UPS), for example, bortezomib, carfilzomib, marizomib (NPI-0052), and MLN9708; and (xii) chimeric antigen receptors, anticancer vaccines and arginase inhibitors.

Suitably, the composition of the present invention may be used in combination with one or more therapeutic enzymes which deplete amino acids. Such therapeutic enzymes may be correlated with the composition of the present invention.

For example, for compositions which are substantially devoid of arginine, a therapeutic enzyme such as arginase may be used.

In addition, or in the alternative, the composition of the present invention may be used in combination with one or more compounds involved in the inhibition of de novo synthesis of amino acids. Such compounds may be correlated with the composition of the present invention. For example, for compositions which are substantially devoid of serine, compounds which inhibit de novo synthesis of serine may be used, such as PHGDH inhibitors, PSAT1 inhibitors and PSPH inhibitors.

The therapeutic agent used in the present methods can be a single agent or a combination of agents. Preferred combinations will include agents that have different mechanisms of action.

Herein, where the term "combination" is used it is to be understood that this refers to simultaneous, separate or sequential administration. In one aspect of the invention "combination" refers to simultaneous administration. In another aspect of the invention "combination" refers to separate administration. In a further aspect of the invention "combination" refers to sequential administration. Where the administration is sequential or separate, the delay in administering the second component should not be such as to lose the beneficial effect of the combination.

The term "administered in combination with" and grammatical equivalents or the like, as used herein, are meant to encompass administration of the selected therapeutic agents to a single patient, and are intended to include treatment regimens in which the agents are administered by the same or different route of administration or at the same or different times. In some embodiments the compounds described herein will be co-administered with other agents. These terms encompass administration of two or more agents to an animal so that both agents and/or their metabolites are present in the animal at the same time.

They include simultaneous administration in separate compositions, administration at different times in separate compositions, and/or administration in a composition in which both agents are present.

The agents disclosed herein may be administered by any route, including intradermally, subcutaneously, orally, intraarterially or intravenously.

In some embodiments in which a combination treatment is used, the amount of the dietary product or pharmaceutical composition of the invention and the amount of the other pharmaceutically active agent(s) are, when combined, therapeutically effective to treat a targeted disorder in the patient. In this context, the combined amounts are "therapeutically effective amount" if they are, when combined, sufficient to reduce or completely alleviate symptoms or other detrimental effects of the disorder; cure the disorder; reverse, completely stop, or slow the progress of the disorder; or reduce the risk of the disorder getting worse. Typically, such amounts may be determined by one skilled in the art by, for example, starting with the dosage range described in this specification for the compound of the invention and an approved or otherwise published dosage range(s) of the other pharmaceutically active compound(s).

According to a further aspect of the invention there is provided a dietary product or pharmaceutical composition of the invention as defined hereinbefore and an additional anti-cancer agent as defined hereinbefore, for use in the conjoint treatment of cancer.

According to a further aspect of the invention there is provided a method of treatment of a human or animal subject suffering from a cancer comprising administering to the subject a therapeutically effective amount of a dietary product or pharmaceutical composition of the invention, simultaneously, sequentially or separately with an additional anti-cancer agent as defined hereinbefore.

According to a further aspect of the invention there is provided a dietary product or pharmaceutical composition of the invention for use simultaneously, sequentially or separately with an additional anti-cancer agent as defined hereinbefore, in the treatment of a cancer.

The dietary product or pharmaceutical composition the invention may also be used be used in combination with radiotherapy. Suitable radiotherapy treatments include, for example X-ray therapy, proton beam therapy or electron beam therapies. Radiotherapy may also encompass the use of radionuclide agents, for example 131I, 32P, 90Y, 89Sr, 153Sm or 223Ra. Such radionuclide therapies are well known and commercially available.

According to a further aspect of the invention there is provided a dietary product or pharmaceutical composition of the invention, or a pharmaceutically acceptable salt thereof as defined hereinbefore for use in the treatment of cancer conjointly with radiotherapy.

According to a further aspect of the invention there is provided a method of treatment of a human or animal subject suffering from a cancer comprising administering to the subject a therapeutically effective amount of a dietary product or pharmaceutical composition of the invention, or a pharmaceutically acceptable salt thereof simultaneously, sequentially or separately with radiotherapy.

Suitably, the present invention has surprisingly found that the combination of a diet substantially devoid of at least one amino acid in combination at least one chemotherapeutic agent or radiotherapy may be more than merely additive.

Suitably, in some embodiments, the present invention may provide a synergistic combination of a dietary product or pharmaceutical composition of the present invention in combination with at least one chemotherapeutic agent or radiotherapy.

In one embodiment, the dietary product or pharmaceutical composition of the invention may be combined with one or more classes of chemotherapeutic agents selected from the group consisting of: HDAC inhibitors, MTOR inhibitors, Tyrosine kinase inhibitors and proteasome inhibitors.

HDAC Inhibitors

Suitably, the chemotherapeutic agent may be one or more histone deacetylase (HDAC) inhibitors. Inhibitors of HDACs modulate transcription and induce cell growth arrest, differentiation, and apoptosis. HDAC inhibitors (HDACIs) also enhance the cytotoxic effects of therapeutic agents used in cancer treatment, including radiation and chemotherapeutic drugs.

The term "HDAC" refers to a family of enzymes that remove acetyl groups from a protein, for example, the ε-amino groups of lysine residues at the N-terminus of a histone. The HDAC can be a human HDAC, including, HDAC1, HDAC2, HDAC3, HDAC4, HDAC5, HDAC6, HDAC7, HDAC8, HDAC9, HDAC10, and HDAC11. The HDAC also can be derived from a protozoal or fungal source.

HDAC inhibitors (HDACIs) typically contain three structural elements which are analogous to the structure of acetyllysine. These three structural elements are a zinc binding group (M), which is responsible for chelation of zinc in the active site, a linker region (L), which binds to the hydrophobic channel that connects the active site to the outer enzyme surface, and a capping group (Cap), which interacts with residues at the outer enzyme surface, Examples of HDAC inhibitors include: SAHA, Romidepsin, Valproic Acid, PCI-24781, ITF-2357, MS275, Panbinoastat, Belinostat, Vorinostat, MGCD0103 and EVP-0334.

The present invention has surprisingly found that HDAC inhibitors such as Romidepsin and Vorinsostat can work in synergy with a dietary product or pharmaceutical composition of the present invention.

Suitably, a dietary product or pharmaceutical composition of the present invention may be used in combination with a HDAC inhibitor for any indication which HDAC inhibitors have utility in treating, HDAC inhibitors have been approved for or clinical trials are underway in at least the following: T-cell lymphoma, multiple myeloma, renal cancer, Hodgkins lymphoma, Follicular lymphoma, leukemia, acute myeloid leukemia, melanoma, non small cell lung cancer, solid tumours, prostate cancer, diffuse large B-cell lymphoma and mesothelioma, for example. Preferably, the HDAC inhibitor is Romidepsin and/or Vorinsostat, mTOR Inhibitors Suitably, the chemotherapeutic agent may be one or more mammalian target of rapamycin (mTOR) inhibitors. The phrase "mTOR inhibitor" as used herein, includes but is not limited to compounds, proteins or antibodies which target/inhibit the activity of members of the mTOR kinase family. Inhibitors of mTOR activity e.g. include rapamycin of formula:

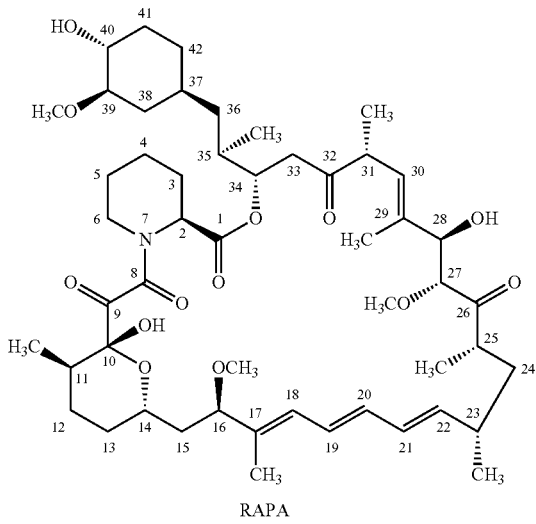 [SMILES: CO[C@@H]1C[C@@H]2CC[C@@H](C)[C@@](O)(O2)C(=O)C(=O)N2CCCC[C@H]2C(=O)O[C@H]([C@H](C)C[C@@H]2CC[C@@H](O)[C@H](OC)C2)CC(=O)[C@H](C)/C=C(\C)[C@@H](O)[C@@H](OC)C(=O)[C@@H](C)C[C@H](C)/C=C/C=C/C=C/1C]

RAPA and rapamycin derivatives, e.g. including

40-O-substituted rapamycin derivatives, such as

40-O-alkyl-rapamycin derivatives, such as 40-O-hydroxyalkyl-rapamycin derivatives, such as 40-O-(2-hydroxy)-ethyl-rapamycin (everolimus), 32-deoxo-rapamycin derivatives and 32-hydroxy-rapamycin derivatives, such as 32-deoxorapamycin, 16-O-substituted rapamycin derivatives such as 16-pent-2-ynyloxy-32-deoxorapamycin, 16-pent-2-ynyloxy-32(S or R)-dihydro-rapamycin, 16-pent-2-ynyloxy-32(S or R)-dihydro-40-O-(2-hydroxyethyl)-rapamycin, rapamycin derivatives which are acylated at the oxygen group in position 40, e.g. 40-[3-hydroxy-2-(hydroxymethyl)-2-methylpropanoate]-rapamycin (also known as CCI779), rapamycin derivatives which are substituted in 40 position by heterocyclyl, e.g. 40-epi-(tetrazolyl)-rapamycin (also known as ABT578), the so-called rapalogs, e. g. as disclosed in WO9802441 or WO0114387, e.g. such as 40-O-phospho-containing rapamycin derivatives, e.g. 40-O-dimethylphosphinyl-rapamycin, including AP23573, and 40-O-alkoxy-alkyl-rapamycin derivatives, such as compounds as disclosed under the name biolimus (biolimus A9), including 40-O-(2-ethoxy)-ethyl-rapamycin (everolimus), and compounds disclosed under the name TAFA-93, AP23464, AP23675 or AP23841.

The present invention has surprisingly found that mTOR inhibitors such as Temsirolimus and Everolimus can work in synergy with a dietary product or pharmaceutical composition of the present invention.

Suitably, a dietary product or pharmaceutical composition of the present invention may be used in combination with an mTOR inhibitor for any indication which mTOR inhibitors have utility in treating. mTOR inhibitors have been approved for or clinical trials are underway in at least the following: lymphatic leukemia, colon and mammary cancers, melanocarcinoma and ependymoblastoma; U.S. skin carcinomas, central nervous system neoplasms; Renal cell carcinoma, Mantle cell lymphoma, Breast and Pancreatic Neuroendocrine, for example. Preferably, the mTOR inhibitor is Temsirolimus and/or Everolimus.

Tyrosine Kinase Inhibitors

Suitably, the chemotherapeutic agent may be one or more tyrosine kinase inhibitors. Tyrosine kinases function in cellular signal transduction. Cell proliferation, differentiation, migration, metabolism and programmed death are examples of tyrosine kinase-mediated cellular responses. Various tyrosine kinase inhibitors are known to have utility in the treatment of cancer and, in one embodiment, any known tyrosine kinase inhibitor may be used. Such inhibitors include commercially available inhibitors and inhibitors under development.

Small molecule inhibitors, such as curcumin, difluorinated curcumin (DFC), [3-{5-[4-(cyclopentyloxy)-2-hydroxybenzoyl]-2-[(3-hydroxy-1,2-benzisoxazol-6-yl)methoxy]phenyl}propionic acid] (T5224, Roche), nordihydroguaiaretic acid (NDGA), dihydroguaiaretic acid (DHGA), [(E,E,Z,E)-3-methyl-7-(4-methylphenyl)-9-(2,6,6-trimethyl-1-cyclohexen-1-yl)-2,4,6,8-nonatetraenoic acid (SR1 1302, Tocris Biosciences), (EJ-2-benzylidene-3-(cyclohexylamino)-2,3-dihydro-1H-inden-1-one (BCI), TPI-2, TPI-3, triptolide, lapatinib, erlotinib, sunitinib, and vemurafenib (PLX4032) are encompassed. In one embodiment, inhibitors of c-Fos used in the composition are curcumin, difluorinated curcumin (DFC), [3-{5-[4-(cyclopentyloxy)-2-hydroxybenzoyl]-2-[(3-hydroxy-1,2-benzisoxazol-6-yl)methoxy]phenyl}propionic acid] (T5224, Roche), nordihydroguaiaretic acid (NDGA), dihydroguaiaretic acid (DHGA), and [(E,E,Z,E)-3-methyl-7-(4-methylphenyl)-9-(2,6,6-trimethyl-1-cyclohexen-1-yl)-2,4,6,8-nonatetraenoic acid (SR1 1302, Tocris Biosciences). In one embodiment, inhibitors of Dusp-1 are (EJ-2-benzylidene-3-(cyclohexylamino)-2,3-dihydro-1H-inden-1-one (BCI), also known as NSC 1501 17, TPI-2, TPI-3, and triptolide. In one embodiment, inhibitors of tyrosine kinase are lapatinib, erlotinib, sunitinib, and vemurafenib Further examples of Tyrosine kinase inhibitors which may be used as a chemotherapeutic agent in accordance with the present invention include: Afatinib (Giotrif), Axitinib (Inlyta), Bosutinib (Bosulif), Crizotinib (Xalkori), Dasatinib (Sprycel), Erlotinib (Tarceva), Gefitinib (Iressa), Imatinib (Glivec), Lapatinib (Tyverb), Nilotinib (Tasigna), Pazopanib (Votrient), Regorafenib (Stivarga), Sorafenib (Nexavar) and Sunitinib (Sutent).

The present invention has surprisingly found that tyrosine kinase inhibitors such as Dasatnib and Regorafenib can work in synergy with a dietary product or pharmaceutical composition of the present invention.

Suitably, a dietary product or pharmaceutical composition of the present invention may be used in combination with tyrosine kinase inhibitor for any indication which tyrosine kinase inhibitors have utility in treating. Tyrosine inhibitors have been approved for or clinical trials are underway in at least the following: non small cell lung cancer, kidney cancer, soft tissue sarcoma, thyroid cancer, chronic myeloid leukaemia (CML), lung cancer, acute myeloid leukaemia, acute lymphoblastic leukaemia, gastro intestinal stromal tumour (GIST), sarcoma, chronic eosinophilic leukaemia, bowel cancer, liver cancer and pancreatic cancer for example. Preferably, the Tyrosine kinase inhibitor is Dasatnib and/or Regorafenib.

Suitably, the cancer to be treated when using Dasatnib and/or Regorafenib is colorectal cancer, chronic myeloid leukaemia (CML), acute myeloid leukaemia. acute lymphoblastic leukaemia, bowel cancer or GIST.

Proteasome Inhibitors

Suitably, the chemotherapeutic agent may be one or more proteasome inhibitors. Proteasome inhibitors refer to inhibitors of the ubiquitin proteasome system (UPS). UPS is a non-lysomal protein degradation pathway. The conjugation of ubiquitin to protein surfaces is a multistep process in which ubiquitin is activated by the E1 conjugating enzyme and is transferred is mediated by ubiquitin conjugases (E2) and E3 ubiquitin ligases. Such inhibitors may include commercially available inhibitors and inhibitors under development.

Examples include: bortezomib (Velcade) and analogs thereof (such as boronic acid derivatives, benzylmalonic- and amino acid-based derivatives and boronic ester), salinosporamide A (NPI-0052), PR-171, E1-conjugating enzyme inhibitors, POSH inhibitors, MDM2-p53 inhibitors and deubiquitylating enzyme inhibitors.

The present invention has surprisingly found that proteasome inhibitors such as Carfilzomib can work in synergy with a dietary product or pharmaceutical composition of the present invention.

Suitably, a dietary product or pharmaceutical composition of the present invention may be used in combination with a proteasome inhibitor for any indication which proteasome inhibitors have utility in treating. Non-limiting examples of solid tumors that can be treated with the disclosed proteasome inhibitors include pancreatic cancer; bladder cancer; colorectal cancer; breast cancer, including metastatic breast cancer; prostate cancer, including androgen-dependent and androgen-independent prostate cancer; renal cancer, including, e.g., metastatic renal cell carcinoma; hepatocellular cancer; lung cancer, including, e.g., non-small cell lung cancer (NSCLC), bronchioloalveolar carcinoma (BAC), and adenocarcinoma of the lung; ovarian cancer, including, e.g., progressive epithelial or primary peritoneal cancer; cervical cancer; gastric cancer; esophageal cancer; head and neck cancer, including, e.g.; squamous cell carcinoma of the head and neck; melanoma; neuroendocrine cancer, including metastatic neuroendocrine tumors; brain tumors, including, e.g., glioma, anaplastic oligodendroglioma, adult glioblastoma multiforme, and adult anaplastic astrocytoma; bone cancer; and soft tissue sarcoma.

Non-limiting examples of hematologic malignancies that can be treated with the disclosed proteasome inhibitors include acute myeloid leukemia (AML); chronic myelogenous leukemia (CML), including accelerated CML and CML blast phase (CML-BP); acute lymphoblastic leukaemia (ALL); chronic lymphocytic leukaemia (CLL); Hodgkin's disease (HD); non-Hodgkin's lymphoma (NHL), including follicular lymphoma and mantle cell lymphoma; B-cell lymphoma; T-cell lymphoma; multiple myeloma (MM); Waldenstrom's macroglobulinemia; myelodysplastic syndromes (MDS), including refractory anemia (RA), refractory anemia with ringed sideblasts (RARS), (refractory anemia with excess blasts (RAEB), and RAEB in transformation (RAEB-T); and myeloproliferative syndromes.

Preferably, the proteasome inhibitor is Carfilzomib.

Suitably, the cancer to be treated when using Carfilzomib is multiple myeloma or T-cell lymphoma.

EGFR Inhibitors

Suitably, the chemotherapeutic agent may be one or more epidermal growth factor receptor (EGFR) inhibitors. EGFR (also known as ErbB-1 or HER-1) inhibitors refer to inhibitors of the cell-surface receptor for members of the EGF-family of extracellular protein ligands. EGFRs play an important role in controlling normal cell growth, apoptosis and other cellular functions. Mutations of EGFRs can lead to continual or abnormal activation of the receptors causing unregulated cell division, which can account for some types of cancers.

In one aspect, the term "EGFR" refers to HER2/c-neu (ErbB-2), HER 3 (ErbB-3) and HER 4 (ErbB-4) as well as EGFR (ErbB-1).

The present invention has surprisingly found that EGFR inhibitors such as cetimuxab can wor kin synergy with a dietary product or pharmaceutical composition of the present invention.

Suitably, a dietary product or pharmaceutical composition of the present invention may be used in combination with an EGFR inhibitor for any indication which EGFR inhibitors have utility in treating. Non-limiting examples of solid tumors that can be treated with the disclosed EGFR inhibitors include non-small-cell lung cancer, pancreatic cancer, breast cancer, colon cancer and some other cancers that are caused by epidermal growth factor receptor up-regulation.

Examples of EGFR inhibitors include: cetuximab, gefitinib, erlotinib, lapatinib, panitumumab, vandetanib, necitumumab and osimertinib.

Preferably, the proteasome inhibitor is cetuximab.

Other Chemotherapeutic Agents of Interest.

In one aspect, the dietary product or pharmaceutical composition of the invention may be combined with one or more chemotherapeutic agents selected from the group consisting of: Tamoxifen citrate, Metformin, Erlotinib hydrochloride, Dasatinib, Estramustine phosphate sodium, Daunorubicin hydrochloride, Vorinostat, Cabozantinib, Idelalisib, Vinorelbine tartrate, Temsirolimus, Hydroxyurea, Melphalan hydrochloride, Valrubicin, Everolimus, Amifostine, Tretinoin, Fludarabine phosphate, Dacarbazine, Vemurafenib, Ceritinib, Arsenic trioxide, Temozolomide, Dexrazoxane, Regorafenib, Sorafenib, Exemestane, Romidepsin, Bosutinib, Capecitabine, Lenalidomide, Allopurinol, Streptozocin, Altretamine, Cisplatin, Doxorubicin hydrochloride, Nilotinib, Imiquimod, Carfilzomib, Vandetanib, Vismodegib, Fluorouracil, Olaparib, Mitotane, Anastrozole, Epirubicin hydrochloride, Raloxifene, Lapatinib, Pazopanib hydrochloride, Fulvestrant, Uracil mustard, Afatinib, Ifosfamide, Etoposide, Triethylenemelamine, Ponatinib and analogues thereof.

Advantageously, the present invention has shown that these chemotherapeutic agents have more than additive (i.e, synergistic effects) when combined with a diet in which serine and glycine are restricted.

Accordingly, in one aspect, the present invention provides a synergistic combination of a dietary product or pharmaceutical composition of the invention and one or more chemotherapeutic agents for use in the treatment of cancer. Any dose of chemotherapeutic agent which results in a synergistic combination may be used.

Suitably, the chemotherapeutic agent may be daunorubicin. A combination of a dietary product or pharmaceutical composition of the invention and daunorubicin may be used in the treatment of acute myeloid leukaemia, acute lymphocytic leukaemia, chronic myelogenous leukaemia and Kaposki's sarcoma, for example.

In one aspect, the dose of each chemotherapeutic agent (or total combined dose of chemotherapeutic agents) may be equivalent to at least 0.1 g/Kg body weight of patient per day, preferably at least 0.2 g/Kg per day or 0.3 g/Kg per day or 0.4 g/Kg per day or 0.5 g/Kg per day. Suitably, the dose of chemotherapeutic agent (or combined combinations of chemotherapeutic agents) may be equivalent to at least 1 g/Kg per day, preferably 2 g/Kg per day.

For example; when the subject is a human for metformin the dose may be equivalent to at least 1 g per day, preferably 2 g per day or an equivalent dose for a non-human.

Further, in another aspect, the present invention provides a method of treating cancer in a subject comprising administering a synergistically effective combination of: a) a dietary product of the invention and b) a chemotherapeutic agent. Suitably, the components of the synergistic combination may be administered simultaneously or sequentially.

Suitably, in accordance with all aspect of the invention, the chemotherapeutic agents may: a) inhibit OXPHOS; b) increase reactive oxygen species (ROS); c) decrease antioxidant defence, or d) provide any combination of a)-c).

Suitably, the chemotherapeutic agent may inhibit OXPHOS. For example, the chemotherapeutic agent may be a biguanide. Without wishing to be bound by theory, it is believed that a dietary product or pharmaceutical composition of the invention (particularly a dietary product or pharmaceutical composition substantially devoid of at least serine) will improve the anti-tumour effects of biguanides.

Suitably, the chemotherapeutic agent may increase ROS levels. Without wish to be bound by theory, it is believed that a dietary product or pharmaceutical composition of the invention (particularly a dietary product or pharmaceutical composition substantially devoid of at least serine) will have an enhanced effect when used in combination with a compound which increases ROS levels. Cancer cells utilise large amounts of exogenous serine to support rapid proliferations in order to deal with elevated ROS levels. Without wishing to be bound by theory, it is believed that when exogenous serine is depleted, cancer cells are forced to channel glycolytic intermediates through the serine synthesis pathway, and the metabolic remodelling may result in reduced proliferation and cell survival.

KRAS

The inventors have surprisingly identified that the level of Kras expression or activity in cancerous cells/tissues is indicative of likelihood of responsiveness or sensitivity of a patient to a cancer treatment comprising a diet substantially devoid of serine (and/or glycine). The level of Kras expression or activity can be used to identify cancer cells, for example tumours, in a subject that will be responsive to a cancer treatment comprising a diet substantially devoid of serine. The biomarker can also be used to identify a subject having an increased likelihood or decreased likelihood of responsiveness or sensitivity to a cancer treatment comprising a diet substantially devoid of serine. The biomarker can also be used to aid in the selection of a treatment for a patient's cancer. In this regard the invention provides biomarkers, and use thereof, including methods and kits comprising use of the biomarker.

In one aspect the invention provides use of KRAS as a biomarker to identify a patient population responsive to or sensitive to a cancer treatment comprising a diet substantially devoid of serine. The term "biomarker" or "marker" refers to an organic biomolecule which is differentially present in a sample taken from a subject of one phenotypic status as compared with another phenotypic status. A biomarker is differentially present between different phenotypic statuses if the difference in the mean or median expression levels of the biomarker in the different groups is calculated to be statistically significant. Biomarkers, alone or in combination, provide measures of relative risk that a subject belongs to one phenotypic status or another. For the purpose of this invention, biomarkers are the markers for predicting likelihood of responsiveness or sensitivity to a cancer treatment comprising a diet substantially devoid of serine. In some embodiments, the biomarkers are the genes disclosed herein (e.g. nucleic acids). In some other embodiments, the biomarkers are the product of the genes (e.g. proteins).

As used herein, the term "KRAS" refers to the human cellular homolog of a transforming gene isolated from the Kirsten rat sarcoma virus. KRAS gene belongs to a class of genes known as oncogenes. When mutated, oncogenes have the potential to cause normal cells to become cancerous. The KRAS gene is in the Ras family of oncogenes, which also includes two other genes: HRAS and NRAS. The proteins produced from these three genes are GTPases. These proteins play important roles in cell division, cell differentiation, and the self-destruction of cells (apoptosis).

KRAS belongs to the RAS family of proteins with a molecular weight of about 21 kDa and GTP hydrolytic activity. KRAS is found inside the cell membrane, and has a role to transmit signals into cells in response to the binding of extracellular growth factors such as Epidermal Growth Factor (EGF) with the receptors. Activating mutations can be found in KRAS, and they are found in about 20% of human cancer.

As used herein, the term "KRAS" is used to refer to both polypeptides and nucleic acid molecules.

Preferably the KRAS is a human KRAS polypeptide or nucleic acid molecule.

As used herein, the term "nucleic acid molecule" includes DNA molecules (e.g., a cDNA or genomic DNA) and RNA molecules (e.g., a mRNA) and analogs of the DNA or RNA generated, e.g., by the use of nucleotide analogs. The nucleic acid molecule can be single-stranded or double-stranded, but preferably is double-stranded DNA.

The nucleic acid sequence information of human KRAS can be found under the Ensembl accession number ENSG00000133703. In one specific embodiment, the KRAS gene of the present invention comprises KRAS nucleic acid (e.g. Ensembl accession number ENSG00000133703) or contiguous fragment thereof, or sequences at least 60%, 65%, 70%, 75%, 80%, 85%, 90%, 95%, 98% or at least 99% identical to the nucleic acid sequence of Ensembl accession number ENSG00000133703 or the contiguous fragment thereof.

As used herein the term "wild-type" KRAS refers to a KRAS polypeptide or nucleic acid containing no mutation, e.g. no mutation compared to the KRAS nucleic acid or polypeptide found under the Ensembl accession number ENSG00000133703. The nucleic acid sequences of KRAS of mammalian or non-mammalian species other than the herein provided sequences for human KRAS can be identified by the skilled person using methods known in the art, e.g. by nucleic acid sequencing or using hybridization assays or by using alignments, either manually or by using computer programs such as those mentioned herein below in connection with the definition of the term "hybridization" and degrees of homology.

Hybridization assays for the characterization of orthologs of known nucleic acid sequences/promoters are well known in the art; see e.g. Sambrook, Russell "Molecular Cloning, A Laboratory Manual", Cold Spring Harbor Laboratory, N.Y. (2001): Ausubel, "Current Protocols in Molecular Biology", Green Publishing Associates and Wiley Interscience, N.Y. (1989). The term "hybridization" or "hybridizes" as used herein may relate to hybridizations under stringent or non-stringent conditions. If not further specified, the conditions are preferably non-stringent. Said hybridization conditions may be established according to conventional protocols described, e.g. in Sambrook (2001) loc. cit.; Ausubel (1989) loc. cit., or Higgins and Hames (Eds.) "Nucleic acid hybridization, a practical approach" IRL Press Oxford, Washington D.C., (1985). The setting of conditions is well within the skill of the artisan and can be determined according to protocols described in the art. Thus, the detection of only specifically hybridizing sequences will usually require stringent hybridization and washing conditions such as, for example, the highly stringent hybridization conditions of 0.1×SSC, 0.1% SDS at 65° C. or 2×SSC, 60° C., 0.1% SDS. Low stringent hybridization conditions for the detection of homologous or not exactly complementary sequences may, for example, be set at 6×SSC, 1% SDS at 65° C. As is well known, the length of the probe and the composition of the nucleic acid to be determined constitute further parameters of the hybridization conditions As used herein, the terms "homology" and "identity" are used interchangeably. Calculations of sequence homology or identity between sequences are performed as follows.

To determine the percent identity of two amino acid sequences, or of two nucleic acid sequences, the sequences are aligned for optimal comparison purposes (e.g. gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 75%, 80%, 82%, 84%, 85%, 86%, 87%, 88%, 89%, 90%, 91%, 92%, 93%, 94%, 95%, 96%, 97%, 98%, 99%, or 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman et al. (1970) *J. Mol. Biol.* 48:444-453) algorithm which has been incorporated into the GAP program in the GCG software package (available at http://www.gcg.com), using either a BLOSUM 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available at http://www.gcg.com), using a NWSgapdna.CMP matrix and a gap weight of 40, 50, 60, 70, or 80 and a length weight of 1, 2, 3, 4, 5, or 6. A particularly preferred set of parameters (and the one that should be used if the practitioner is uncertain about what parameters should be applied to determine if a molecule is within a sequence identity or homology limitation of the invention) are a BLOSUM 62 scoring matrix with a gap penalty of 12, a gap extend penalty of 4, and a frameshift gap penalty of 5.

Alternatively, the percent identity between two amino acid or nucleotide sequences can be determined using the algorithm of Meyers et al. (1989) CAB/OS 4:11-17) which has been incorporated into the ALIGN program (version 2.0), using a PAM120 weight residue table, a gap length penalty of 12 and a gap penalty of 4.

As used herein, the term "contiguous fragment" refers to a non-interrupted sequence of nucleic acids or amino acids also occurring in the same order in the sequence referred to. Particularly envisaged are contiguous fragments having a length of at least 25%, 50%, 70%, 75%, 80% or 90% of the length of the reference sequence, and contiguous fragments having typically at least 25 nucleic acids or at least 8 amino acids.

In one embodiment, a nucleic acid fragment comprises or consists of a sequence corresponding to a domain, region, or functional site of KRAS. Alternatively a nucleic acid fragment of KRAS encodes an epitope bearing region of a KRAS polypeptide.

In an alternative embodiment, KRAS may be selected from the group consisting of, but not limited to, human KRAS (NP_004976.2, NP_203524.1, etc.), mouse KRAS (NP_067259.4, etc.), zebrafish KRAS (NP_001003744.1, etc.), frog KRAS (NP_001095209.1), cow KRAS (NP_001103471.1), chicken KRAS (NP_001243091.1), monkey KRAS (NP_001248441.1), NP_001028153.1, NP_113703.1, and NP_001008034.1, or a variant or mutation thereof.

The polypeptide sequence information of human KRAS can be found under the Ensembl accession number ENSG00000133703. In one specific embodiment, the KRAS polypeptide of the present invention comprises KRAS (e.g. Ensembl accession number ENSG00000133703) or contiguous fragment thereof, or sequences at least 60%, 65%, 70%, 75%, 80%, 85%, 90%, 95%, 98% or at least 99% identical to the polypeptide sequence of Ensembl accession number ENSG00000133703 or the contiguous fragment thereof.

The KRAS polypeptide may be an allelic variant of the KRAS polypeptide sequence of Ensembl accession number ENSG00000133703. The KRAS polypeptide may be an epitope bearing region of a KRAS polypeptide of the KRAS polypeptide sequence of Ensembl accession number ENSG00000133703. The KRAS polypeptide may be a fragment, for example a biologically active fragment, of the KRAS polypeptide sequence of Ensembl accession number ENSG00000133703.

As used herein, a "biologically active fragment" of a KRAS polypeptide includes peptides comprising amino acid sequences sufficiently homologous to or derived from the amino acid sequence of a KRAS polypeptide, e.g., polypeptide sequence of Ensembl accession number ENSG00000133703, which include fewer amino acids than the full length KRAS polypeptide, and exhibit at least one activity of a KRAS polypeptide. For example, a biologically active fragment of a KRAS polypeptide can be a polypeptide which comprises or consists of 10, 25, 50, 100, 200 or more contiguous amino acids a KRAS polypeptide of the KRAS polypeptide sequence of Ensembl accession number ENSG00000133703.

In the context of the determination of the activity of KRAS, the term "activity" used herein comprises, for example, determining the enzymatic activity at the protein level and/or the determination of the expression level (e.g. mRNA or protein). Methods for determining the activity as defined herein are well known in the art and also described herein below.

In one embodiment the KRAS is a mutant KRAS, for example an activating KRAS mutant. The term "activating mutation" used herein refers to a mutation in a gene, in particular in the KRAS gene, which leads to an increased activity of the corresponding gene product, i.e. the protein, in particular the KRAS protein compared to wild type. Methods for measuring the (increased) activity of a protein, in particular the KRAS protein, are known in the art and also described herein below. Mutations in the KRAS gene, can be detected by methods known in the art. Such methods are, for example described in (Papadopoulos et al., 2006; Shendure et al., 2004).

The invention provides methods of identifying a subject having a decreased likelihood of responsiveness or sensitivity to a cancer treatment comprising a diet substantially devoid of serine comprising:
 a) determining the level of Kras expression or activity in a biological sample isolated from the subject;
 b) comparing the level of Kras expression or activity in the biological sample to a control sample or to a predetermined reference level of Kras expression or activity,
 wherein an increased level of Kras expression or activity in the biological sample compared to the control sample or compared to the predetermined reference level is indicative of non-responsiveness or insensitivity to said cancer treatment.

The invention also provides methods of identifying a subject having an increased likelihood of responsiveness or sensitivity to a cancer treatment comprising a diet substantially devoid of serine comprising:
 a) determining the level of Kras expression or activity in a biological sample isolated from the subject;
 b) comparing the level of Kras expression or activity in the biological sample to a control sample or to a predetermined reference level of Kras expression or activity,
 wherein an decreased level of Kras expression or activity in the biological sample compared to the control sample or compared to the predetermined reference level, or a level of Kras expression or activity which is substantially the same as the control sample or the predetermined reference level is indicative of responsiveness or sensitivity to said cancer treatment.

The invention also provides methods of identifying a subject who may benefit from a cancer treatment comprising a diet substantially devoid of serine comprising:
 a) determining the level of Kras expression or activity in a biological sample isolated from the subject;
 b) comparing the level of Kras expression or activity in the biological sample to a control sample or to a predetermined reference level of Kras expression or activity,
 wherein an decreased level of Kras expression or activity in the biological sample compared to the control sample or compared to the predetermined reference level, or a level of Kras expression or activity which is substantially the same as the control sample or the predetermined reference level indicates that the patient may benefit from said cancer treatment.

MTAP

The inventors have surprisingly identified that the level of methylthioadenosine phosphorylase (MTAP) expression or activity in cancerous cells/tissues is indicative of likelihood of responsiveness or sensitivity of a patient to a cancer treatment comprising a diet substantially devoid of: i) cysteine and/or ii) serine. The level of MTAP expression or activity can be used to identify cancer cells, for example tumours, in a subject that will be responsive to a cancer treatment comprising a diet substantially devoid of cysteine and/or cysteine. The biomarker can also be used to aid in the selection of a treatment for a patient's cancer. In this regard the invention provides biomarkers, and use thereof, including methods and kits comprising use of the biomarker.

In a further aspect the invention provides use of MTAP as a biomarker to identify a patient population responsive to or sensitive to a cancer treatment comprising a diet substantially devoid of cysteine and/or serine.

The invention also provides methods of identifying a subject who may benefit from a cancer treatment comprising a diet substantially devoid of cysteine comprising:
 a) determining the level of MTAP expression or activity in a biological sample isolated from the subject;
 b) comparing the level of MTAP expression or activity in the biological sample to a control sample or to a predetermined reference level of MTAP expression or activity,
 wherein an decreased level of MTAP expression or activity in the biological sample compared to the control sample or compared to the predetermined reference level, or a level of MTAP expression or activity which is substantially the same as the control sample or the predetermined reference level indicates that the patient may benefit from said cancer treatment.

As used herein, the term "MTAP" refers to S-methyl-5'thioadenosine phosphorylase which catalyses the reversible phosphorylation of S-methyl-5'-thioadnosine (MTA) to adenine and 5-methylthioribose-1-phosphate. This enzyme plays a major role in polyamine metabolism and is important for the salvage of both adenosine and methionine. MTAP is known to be deficient in many cancers, this is often due to the co-deletion of the MTAP gene with the tumour suppressor gene p16.

As used herein, the term "MTAP" is used to refer to both polypeptides and nucleic acid molecules.

Preferably the MTAP is a human MTAP polypeptide or nucleic acid molecule.

The nucleic acid sequence information of human MTAP gene can be found under the Ensembl accession number ENSG00000099810. In one specific embodiment, the MTAP gene of the present invention comprises a MTAP nucleic acid (e.g. Ensembl accession number ENSG00000099810) or contiguous fragment thereof, or sequences at least 60%, 65%, 70%, 75%, 80%, 85%, 90%, 95%, 98% or at least 99% identical to the nucleic acid sequence of Ensembl accession number ENSG00000099810 or the contiguous fragment thereof.

The nucleic acid sequences of MTAP of mammalian or non-mammalian species other than the herein provided sequences for human MTAP can be identified by the skilled person using methods known in the art, e.g. by nucleic acid sequencing or using hybridization assays or by using alignments, either manually or by using computer programs such as those mentioned herein below in connection with the definition of the term "hybridization" and degrees of homology.

In one embodiment, a nucleic acid fragment comprises or consists of a sequence corresponding to a domain, region, or functional site of MTAP. Alternatively a nucleic acid fragment of MTAP encodes an epitope bearing region of a MTAP polypeptide.

In an alternative embodiment, MTAP may be a nucleotide sequence encoding a human MTAP polypeptide, or a variant or mutation thereof.

The polypeptide sequence information of human MTAP can be found under UniProtKB-Q13126. In one specific embodiment, the MTAP polypeptide of the present invention comprises human MTAP or contiguous fragment thereof, or sequences at least 60%, 65%, 70%, 75%, 80%, 85%, 90%, 95%, 98% or at least 99% identical to the polypeptide sequence of UniProtKB-Q13126 (e.g. Q13126-1) or the contiguous fragment thereof.

The MTAP polypeptide may be an allelic variant of the MTAP polypeptide sequence of UniProtKB-Q13126. The MTAP polypeptide may be an epitope bearing region of a MTAP polypeptide sequence of UniProtKB-Q13126. The MTAP polypeptide may be a fragment, for example a biologically active fragment, of the MTAP polypeptide sequence of UniProtKB-Q13126.

As used herein, a "biologically active fragment" of a MTAP polypeptide includes peptides comprising amino acid sequences sufficiently homologous to or derived from the amino acid sequence of a MTAP polypeptide, e.g., polypeptide sequence of UniProtKB—Q131263, which include fewer amino acids than the full length MTAP polypeptide, and exhibit at least one activity of a MTAP polypeptide. For example, a biologically active fragment of a MTAP polypeptide can be a polypeptide which comprises or consists of 10, 25, 50, 100, 200 or more contiguous amino acids a MTAP polypeptide of the MTAP polypeptide sequence of UniProtKB accession number Q13126 (e.g. Q13126-1)..

In the context of the determination of the activity of MTAP, the term "activity" used herein comprises, for example, determining the enzymatic activity at the protein level and/or the determination of the expression level (e.g. mRNA or protein). Methods for determining the activity as defined herein are well known in the art and also described herein below.

As used herein, a subject is "responsive" or "sensitive to" to a cancer treatment comprising a diet substantially devoid of serine if the treatment slows cancer or tumor growth, prevents cancer or tumor growth, or reduces one or more symptoms of the cancer or tumor, for example tumor burden, after or following the treatment. Therefore, in a preferred embodiment, the subject is responsive, if the treatment reduces tumor burden during or after treatment. In some embodiments, a subject is responsive to the treatment if the tumor or cancer goes into remission or is eradicated.

As used herein, a subject is "non-responsive" or "insensitivity" to a cancer treatment comprising a diet substantially devoid of serine if the treatment does not slow cancer or tumor growth, prevents cancer or tumor growth, or does not reduce one or more symptoms of the cancer or tumor, for example, tumor burden, after or following the treatment. Therefore, in a preferred embodiment, the subject is non-responsive, if tumor burden is increased during or after treatment. In some embodiments, a subject is non-responsive to the treatment if the tumor or cancer expands, spreads, or metastasizes, or if one or more symptoms of the cancer worsen during or after treatment.

The disclosed methods of the invention typically include detecting the expression level of KRAS or MTAP in a biological sample obtain from a subject. As used herein, the term "biological sample" and "sample isolated from a subject" are used interchangeably to refer to tissues, cells and biological fluids isolated from a subject, as well as tissues, cells and fluids present within a subject.

In preferred embodiments the subject is a subject with cancer and more preferably the sample is a sample of cancer cells or cancer tissue. The biological sample can include a single cancer cell, or preferable includes multiple cancer cells.

In some embodiments, the biological sample includes cancer cells obtained from a tumor. In some embodiments, the biological sample includes cancer cells that are not obtained from a tumor. For example, in some embodiments, the cancer cells are circulating cancer cells. The biological sample can include other components or cells that are not cancer cells. For example, the sample can include non-cancerous cells, tissue, etc. In preferred embodiments, the biological sample includes cancer cells that isolated or separated away from normal tissue. In some embodiments, the biological sample is obtained from a cancerous tissue or organ.

A biological sample can be obtained from a subject using a variety of methods that are known in the art. In some embodiments, the sample is a tissue biopsy, for example a punch biopsy. The sample should be handled in accordance with the method of detection that will be employed. In some embodiments, a biological sample that is of tissue or cellular origin can be solubilized in a lysis buffer optionally containing one or more of a chaotropic agent, detergent, reducing agent, buffer, and salts. The conditions for handling biological samples that are analyzed for mRNA level may be different than the conditions for handling biological samples that are analyzed for protein level, and such conditions are known in the art. If the sample is a blood sample that include clotting factors (e.g., a whole blood sample), the preparation may include an anti-coagulant.

The sample can be concentrated, or diluted with a suitable diluent before the sample is analyzed. The sample can be frozen, fresh, fixed (e.g. formalin fixed), centrifuged, and/or embedded (e.g. paraffin embedded), etc. The cell sample can be subjected to a variety of well-known post-collection preparative and storage techniques (e.g., nucleic acid and/or protein extraction, fixation, storage, freezing, ultrafiltration, concentration, evaporation, centrifugation, etc.) prior to assessing the amount of the marker in the sample. Likewise, biopsies may also be subjected to post-collection preparative and storage techniques, e.g., fixation.

The types of cancer that can be assayed and treated with the methods of the invention include, but are not limited to, the following: colorectal, liver, osteosarcoma, lymphoma and breast cancer.

In the context of the present invention, the expression of KRAS/MTAP means the gene or protein expression level of the KRAS/MTAP gene or protein as measured by any suitable methods.

Typically, the level of expression of a particular gene may be reflected at the transcription level by measuring the level of mRNA transcribed from the KRAS/MTAP gene in a cell or tissue, or at the translation level by measuring the protein level in a cell or tissue. The methods can be cell-based or cell-free assays.

Methods of detecting the level of expression of KRAS or MTAP in a sample in accordance with the present invention are provided. The expression level of KRAS or MTAP may be determined by measuring the mRNA or protein level of KRAS or MTAP in the sample.

Methods for measuring mRNA in a sample include, for example, quantitative polymerase chain reaction (qPCR), reverse transcription PCR (RT-PCR), reverse transcription real-time PCR (RT-qPCR), transcriptome analysis using next-generation sequencing, array hybridization analysis, digital PCR, Northern analysis, dot-blot, in situ hybridization, and RNase protection assay.

Quantitative real-time PCR is particularly suitable for determining a particular mRNA level in a cell or tissue sample, in which case mRNA is first reverse transcribed into cDNA, which is then amplified by PCR using gene-specific oligonucleotide PCR primers. This qRT-PCR method is well-known in the art. Next-generation sequencing or microarray may also be used for detecting mRNA levels. Additionally, in situ hybridization may also be used to detect in situ the mRNA level of KRAS in a cell or tissue sample, e.g., in a FFPE tissue sample.

In some embodiments, the expression of KRAS and/r MTAP may be determined using PCR, (e.g., qPCR, RT-PCR, RT-qPCR, etc.). Such PCR assays are well known in the art. For example, in some embodiments, a method for detecting mRNA from KRAS/MTAP in a biological sample includes producing cDNA from the sample by reverse transcription using at least one primer; amplifying the cDNA so produced; and detecting the presence of the amplified cDNA. In addition, such methods can include one or more steps that allow one to determine the levels of mRNA in a biological sample (e.g., by simultaneously examining the levels a comparative control mRNA sequence of a "housekeeping" gene such as an actin family member). Optionally, the sequence of the amplified cDNA can be determined. Northern blot analysis is a conventional technique well known in the art and is described, for example, in Sambrook, et al., Molecular Cloning, a Laboratory Manual, third edition, Cold Spring Harbor Press, NY (2000) 11803-2500.

In some embodiments, the KRAS/MTAP genes can be detected by, for example, a probe or primer. The term "probe" as used herein refers to an oligonucleotide, polynucleotide or nucleic acid, either RNA or DNA, whether occurring naturally as in a purified restriction enzyme digest or produced synthetically, which is capable of annealing with or specifically hybridizing to a nucleic add with sequences complementary to the probe. A probe may be either single-stranded or double-stranded. The exact length of the probe will depend upon many factors, including temperature, source of probe and use of the method. For example, for diagnostic applications, depending on the complexity of the target sequence, the oligonucleotide probe typically contains 15-25 or more nucleotides, although it may contain fewer nucleotides.

In some embodiments, the biological sample contains a low quantity of cells, or is a single cell. Methods of amplifying cDNA and analyzing mRNA expression levels in low quantities of cells (e.g., 1,000 to 10 cells) and single cells, are well known in the art. Such methods can include, for example, semirandom primed PCR and phi29-based cDNA amplification steps.

These and other suitable methods for binding (specific) mRNA are well known in the art and are, for example, described in Sambrook and Russell (2001, loc. cit.). A skilled person is capable of determining the amount of the component, in particular said gene products, by taking advantage of a correlation, preferably a linear correlation, between the intensity of a detection signal and the amount of the gene product to be determined.

For detecting the KRAS/MTAP protein expression in a cell or tissue sample, any known methods for measuring protein level in cells or tissue samples may be used for the present invention.

Methods for measuring KRAS/MTAP protein expression in a sample include, for example, immunoassay, ligand binding assay, mass spectroscopy, or high performance liquid chromatography (HPLC). Some methods include immunoassays whereby an antibody specifically immunoreactive with a KRAS/MTAP protein is contacted with a cell or tissue sample under conditions to allow immunoreaction with KRAS/MTAP proteins in the sample, and the amount of bound antibody is measured. Exemplary immunoassays include, but are not limited to radioimmunoassays, ELISAs, immunoprecipitation assays, Western blot, fluorescent immunoassays, and immunohistochemistry, flow cytometry, protein arrays, multiplexed bead arrays, magnetic capture, in vivo imaging, fluorescence resonance energy transfer (FRET), and fluorescence recovery/localization after photobleaching (FRAP/FLAP). In other preferred embodiments, the presence or absence of KRAS in a cell or tissue sample, is determined by IHC.

It will be appreciated that some immunoassays, for example ELISAs, can require two different biomarker specific antibodies or ligands (e.g., a capture ligand or antibody, and a detection ligand or antibody). In certain embodiments, the KRAS is captured with a ligand or antibody on a surface and the protein biomarker is labeled with an enzyme. In one example, a detection antibody conjugated to biotin or streptavidin—to create a biotin-streptavidin linkage to an enzyme that contains biotin or streptavidin. A signal is generated by the conversion of the enzyme substrate into a colored molecule and the intensity of the color of the solution is quantified by measuring the absorbance with a light sensor. Contemplated assays may utilize chromogenic reporters and substrates that produce an observable color change to indicate the presence of the protein biomarker. Fluorogenic, electrochemiluminescent, and real-time PCR reporters are also contemplated to create quantifiable signals.

Some assays optionally including fixing one or more antibodies to a solid support to facilitate washing and subsequent isolation of the complex, prior to contacting the antibody with a sample. Examples of solid supports include glass or plastic in the form of, e.g., a microtiter plate, a stick, a bead, or a microbead. Antibodies can also be attached to a probe, substrate or a ProteinChip® array.

Flow cytometry is a laser based technique that may be employed in counting, sorting, and detecting protein biomarkers by suspending particles in a stream of fluid and passing them by an electronic detection apparatus. A flow cytometer has the ability to discriminate different particles on the basis of color. Differential dyeing of particles with different dyes, emitting in two or more different wavelengths allows the particle to be distinguished. Multiplexed analysis, such as FLOWMETRIX™ is discussed in Fulton, et al., Clinical Chemistry, 43(9):1749-1756 (1997) and can allow one to perform multiple discrete assays in a single tube with the same sample at the same time.

In another preferred embodiment, the expression of KRAS and/or MTAP of the present invention is detected by mass spectrometry. Multidimensional HPLC (High Performance Liquid Chromatography) can be combined with mass spectrometry to separate KRAS.

Also, the presence, absence or level of expression of the KRAS and/or MTAP gene or polypeptide in the patient's cancer can be detected in vivo or in vitro. In some embodiments, expression is detected in vitro, in a biological sample containing genetic material that is isolated from the patient. In some other embodiments, expression of the marker gene can be carried out in vivo, for example using techniques such as "Quantum Dot" labeling or CT scan.

The activity of KRAS may, not only be determined by measuring the expression level but also, be determined, for example, by measuring GTPase activity of KRAS or by measuring the activation of downstream signaling pathway members, e.g., by determining the level of phospho-Akt or phospho-Erk. in case of KRAS. Means and methods for determining the activity of said proteins are well known in the art and may, for example, be deduced from Lottspeich (Spektrum Akademischer Verlag, 1998). KRAS activation assay kits that detect cellular Ras-GTP are well known in the art e.g. Jena Bioscience's Ras activation Kit and Cell Biolabs, Inc K-Ras activation assay kit).

The activity of MTAP may, not only be determined by measuring the expression level but also, be determined, for example, by measuring the cellular efflux of methylthioadenosine (MTA).

Suitably, MTA may be used as a biomarker in accordance with the present invention. In one embodiment, the method and uses relating to MTAP may be substituted with MTA, in this embodiment the correlation between MTA and "responsiveness" or "sensitivity" to treatment with a diet i) substantially devoid of serine and/or ii) restricted in cysteine is reversed. An enhanced efflux of MTA is indicative of responsiveness or sensitivity to such treatment.

The term "activity" as used herein refers to the activity of a protein (e.g. KRAS), whereas the term expression level refers to expression on a protein level (e.g. to be determined by Western Blots and the like) or transcriptional level (e.g. spliced, unspliced or partially spliced mRNA, which may be determined by Northern Blots, Real time PCR and the like).

As used herein, the term "increase" can refer to an increase of 5%, 10%, 20%, 25%, 30%, 40%, 50%, 60%, 70%, 80%, 85%, 90%, 95%, 96%, 97%, 98%, 99% or greater, in biomarker level detected (e.g. expression or activity) by the methods described herein, as compared to the level of the same biomarker from a control or in a reference level. In certain embodiments, the term increase refers to the increase in biomarker level, wherein the increased level is 0.1, 0.5, 1, 2, 3, 4, 5-fold or more higher compared to the level of the biomarker in the control or reference level.

As used herein, the term "decrease" can refer to a reduction of 5%, 10%, 20%, 25%, 30%, 40%, 50%, 60%, 70%, 80%, 85%, 90%, 95%, 96%, 97%, 98%, 99% or greater, in biomarker level detected (e.g. expression or activity) by the methods described herein, as compared to the level of the same biomarker from a control or in a reference level. In certain embodiments, the term decrease refers to the decrease in biomarker level, wherein the decreased level is 0.1, 0.5, 1, 2, 3, 4, 5-fold or more lower compared to the level of the biomarker in the control or reference level.

As used herein, the phrases or "substantially the same" denotes a sufficiently high degree of similarity between two numeric values (for example, one associated with KRAS expression or activity in a test biological sample and the other associated with KRAS expression or activity in a control sample), such that one of skill in the art would consider the difference between the two values to be of little or no biological and/or statistical significance within the context of the biological characteristic measured by said values. The difference between said two values is, for example, less than about 50%, less than about 40%, less than about 30%, less than about 20%, and/or less than about 10% as a function of the reference/comparator value.

The methods disclosed herein include comparing the level of the biomarker (e.g. KRAS and/or MTAP) detected in a sample isolated from the subject to a control or predetermined reference level.

As used herein "control", refers to a sample having a normal level of biomarker expression, for example a sample from a healthy subject not having or suspected of having cancer or, in the case of KRAS, a sample not having or suspected of having a KRAS mutation. Preferably, the control sample is a normal (e.g. non-diseased) cell or tissue sample. Preferably, where the biomarker to be measured in KRAS, the control sample is positive for a wild type KRAS. The control sample may be the same tissue or cell type as the sample isolated from the subject.

As used herein, the term "reference level" refers to a biomarker level (i.e. a KRAS level) that is the same as the level of the same biomarker, detected by the methods described herein, from a control sample. Alternatively, the reference level may be comprised of a biomarker (e.g, KRAS) expression level from a reference database, which may be used to generate a pre-determined cut off value, i.e. a diagnostic score that is statistically predictive of a symptom or disease or lack thereof or may be a pre-determined reference level based on a standard population sample, or alternatively, a pre-determined reference level based on a subject's base line level of expression, i.e. prior to organ transplantation. Preferably biological sample isolated from the subject is assayed using the same testing platform (e.g., analysis of mRNA by RT-PCT, analysis of protein by immunoassay, etc.) as was used to obtain the reference value.

Alternatively, predictions may be based on the normalized expression level of the biomarker (e.g. KRAS). Expression levels are normalized by correcting the absolute expression level of the biomarker (e.g., KRAS) in a sample by comparing its expression to the expression of a reference nucleic acid that is not a marker, e.g., an mRNA, such as an mRNA that is constitutively expressed. This normalization allows the comparison of the expression level in one sample to another sample, or between samples from different sources. This normalized expression can then optionally be compared to a reference level or control.

^^In one aspect the invention provides a method of treating a subject having a cancer comprising:
  a) determining if the level of Kras expression or activity
    in a biological sample isolated from the subject is indicative of responsiveness or sensitivity to a cancer treatment comprising a diet substantially devoid of serine; and b) administering to the subject the cancer treatment, where the level of Kras expression or activity in the biological sample is indicative of responsiveness or sensitivity to said cancer treatment.

In certain embodiment the diet substantially devoid of serine comprises or consists of a dietary product. As used herein, the term "dietary product" refers to a composition comprising one or more essential amino acids or salts or esters thereof, that is used in a food product, or used or consumed in combination with a food product, to provide a desired level of the amino acid(s) or salt or esters thereof to the subject consuming the supplement. The dietary ingredients in these products may include: vitamins, minerals, herbs or other botanicals, amino acids, and substances such as enzymes, organ tissues, glandulars, and metabolites.

Dietary products may be provided in the form of a powder, a gel, a solution, a suspension, a paste, a solid, a liquid, a liquid concentrate, a reconstitutable powder, a shake, a concentrate, a pill, a bar, a tablet, a capsule or a ready-to-use product. It is contemplated that a dietary product can also be a pharmaceutical composition when the supplement is in the form of a tablet, pill, capsule, liquid, aerosol, injectable solution, or other pharmaceutically acceptable formulation.

As used herein "substantially devoid" means completely or very nearly free of serine. In various embodiments, the diet or dietary product is substantially devoid of serine.

In one embodiment said cancer treatment comprises a diet substantially devoid of serine and glycine.

In some embodiments, said cancer treatment comprises a diet substantially devoid of serine is administered to a cancer patient during a chemotherapeutic or radiotherapeutic regimen. Preferably, said cancer treatment further comprises administration of a therapeutic agent selected from: an inhibitor of cancer cell growth, a radiotherapeutic agent and a chemotherapeutic agent.

As used herein an inhibitor of cancer cell growth, a radiotherapeutic agent and a chemotherapeutic agent and/or radiotherapy.

Such chemotherapy may include one or more of the following categories of anti-cancer agents:

(i) antiproliferative/antineoplastic drugs and combinations thereof, such as alkylating agents (for example cis platin, oxaliplatin, carboplatin, cyclophosphamide, nitrogen mustard, uracil mustard, bendamustin, melphalan, chlorambucil, chlormethine, busulphan, temozolamide, nitrosoureas, ifosamide, melphalan, pipobroman, triethylene-melamine, triethylenethiophoporamine, carmustine, lomustine, stroptozocin and dacarbazine); antimetabolites (for example gemcitabine and antifolates such as fluoropyrimidines like 5 fluorouracil and tegafur, raltitrexed, methotrexate, pemetrexed, cytosine arabinoside, floxuridine, cytarabine, 6-mercaptopurine, 6-thioguanine, fludarabine phosphate, pentostatine, and gemcitabine and hydroxyurea); antibiotics (for example anthracyclines like adriamycin, bleomycin, doxorubicin, daunomycin, epirubicin, idarubicin, mitomycin-C, dactinomycin and mithramycin); antimitotic agents (for example *vinca* alkaloids like vincristine, vinblastine, vindesine and vinorelbine and taxoids like taxol and taxotere and polokinase inhibitors); proteasome inhibitors, for example carfilzomib and bortezomib; interferon therapy; and topoisomerase inhibitors (for example epipodophyllotoxins like etoposide and teniposide, amsacrine, topotecan, irinotecan, mitoxantrone and camptothecin); bleomcin, dactinomycin, daunorubicin, doxorubicin, epirubicin, idarubicin, ara-C, paclitaxel (Taxol™), nabpaclitaxel, docetaxel, mithramycin, deoxyco-formycin, mitomycin-C, L-asparaginase, interferons (especially IFN-alpha), etoposide, teniposide, DNA-demethylating agents, (for example, azacitidine or decitabine); and histone de-acetylase (HDAC) inhibitors (for example vorinostat, MS-275, panobinostat, romidepsin, valproic acid, mocetinostat (MGCD0103) and pracinostat SB939);

(ii) cytostatic agents such as antiestrogens (for example tamoxifen, fulvestrant, toremifene, raloxifene, droloxifene and iodoxyfene), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5*-reductase such as finasteride; and navelbene, CPT-II, anastrazole, letrazole, capecitabine, reloxafme, cyclophosphamide, ifosamide, and droloxafine;

(iii) anti-invasion agents, for example dasatinib and bosutinib (SKI-606), and metalloproteinase inhibitors, inhibitors of urokinase plasminogen activator receptor function or antibodies to Heparanase;

(iv) inhibitors of growth factor function: for example such inhibitors include growth factor antibodies and growth factor receptor antibodies, for example the anti erbB2 antibody trastuzumab [Herceptin™], the anti-EGFR antibody panitumumab, the anti erbB1 antibody cetuximab, tyrosine kinase inhibitors, for example inhibitors of the epidermal growth factor family (for example EGFR family tyrosine kinase inhibitors such as gefitinib, erlotinib, 6-acrylamido-N-(3-chloro-4-fluorophenyl)-7-(3-morpholinopropoxy)-quinazolin-4-amine (CI 1033), afatinib, vandetanib, osimertinib and rociletinib) erbB2 tyrosine kinase inhibitors such as lapatinib) and antibodies to costimulatory molecules such as CTLA-4, 4-IBB and PD-I, or antibodies to cytokines (IL-10, TGF-beta); inhibitors of the hepatocyte growth factor family; inhibitors of the insulin growth factor family; modulators of protein regulators of cell apoptosis (for example Bcl-2 inhibitors); inhibitors of the platelet-derived growth factor family such as imatinib and/or nilotinib (AMN107); inhibitors of serine/threonine kinases (for example Ras/Raf signalling inhibitors such as farnesyl transferase inhibitors, sorafenib, tipifarnib and lonafarnib), inhibitors of cell signalling through MEK and/or AKT kinases, c-kit inhibitors, abl kinase inhibitors, PI3 kinase inhibitors, Plt3 kinase inhibitors, CSF-1R kinase inhibitors, IGF receptor, kinase inhibitors; aurora kinase inhibitors and cyclin dependent kinase inhibitors such as CDK2 and/or CDK4 inhibitors; CCR2, CCR4 or CCR6 antagonists; and RAF kinase inhibitors such as those described in WO2006043090, WO2009077766, WO2011092469 or WO2015075483.

(v) antiangiogenic agents such as those which inhibit the effects of vascular endothelial growth factor, [for example the anti vascular endothelial cell growth factor antibody bevacizumab (Avastin™)]; thalidomide; lenalidomide; and for example, a VEGF receptor tyrosine kinase inhibitor such as vandetanib, vatalanib, sunitinib, axitinib and pazopanib;

(vi) gene therapy approaches, including for example approaches to replace aberrant genes such as aberrant p53 or aberrant BRCA1 or BRCA2;

(vii) immunotherapy approaches, including for example antibody therapy such as alemtuzumab, rituximab, ibritumomab tiuxetan (Zevalin®) and ofatumumab; interferons such as interferon α; interleukins such as IL-2 (aldesleukin); interleukin inhibitors for example IRAK4 inhibitors; cancer vaccines including prophylactic and treatment vaccines such as HPV vaccines, for example Gardasil, Cervarix, Oncophage and Sipuleucel-T (Provenge); gp100; dendritic cell-based vaccines (such as Ad.p53 DC); toll-like receptor modulators for example TLR-7 or TLR-9 agonists; PD-1, PD-L1, PD-L2 and CTL4-A modulators (for example Nivolumab), antibodies and vaccines; other IDO inhibitors (such as indoximod); anti-PD-1 monoclonal antibodies (such as MK-3475 and nivolumab); anti-PDL1 monoclonal antibodies (such as MEDI-4736 and RG-7446); anti-PDL2 monoclonal antibodies; and anti-CTLA-4 antibodies (such as ipilumumab; and (viii) cytotoxic agents for example fludaribine (fludara), cladribine, pentostatin (Nipent™);

(ix) targeted therapies, for example PI3K inhibitors, for example idelalisib and perifosine; SMAC (second mitochondriaderived activator of caspases) mimetics, also known as Inhibitor of Apoptosis Proteins (IAP) antagonists (IAP antagonists). These agents act to supress IAPs, for example XIAP, cIAP1 and cIAP2, and thereby re-establish cellular apoptotic pathways. Particular SMAC mimetics include Birinapant (TL32711, TetraLogic Pharmaceuticals), LCL161 (Novartis), AEG40730 (Aegera Therapeutics), SM-164 (University of Michigan), LBW242 (Novartis), ML101 (Sanford-Burnham Medical Research Institute), AT-406 (Ascenta Therapeutics/University of Michigan), GDC-0917 (Genentech), AEG35156 (Aegera Therapeutic), and HGS1029 (Human Genome Sciences); and agents which target ubiquitin proteasome system (UPS), for example, bortezomib, carfilzomib, marizomib (NPI-0052), and MLN9708; and (xii) chimeric antigen receptors, anticancer vaccines and arginase inhibitors.

The therapeutic agent used in the present methods can be a single agent or a combination of agents. Preferred combinations will include agents that have different mechanisms of action.

The term "administered in combination with" and grammatical equivalents or the like, as used herein, are meant to encompass administration of the selected therapeutic agents to a single patient, and are intended to include treatment regimens in which the agents are administered by the same or different route of administration or at the same or different times. In some embodiments the compounds described herein will be co-administered with other agents. These terms encompass administration of two or more agents to an animal so that both agents and/or their metabolites are present in the animal at the same time. They include simultaneous administration in separate compositions, administration at different times in separate compositions, and/or administration in a composition in which both agents are present. Thus, in some embodiments, the compounds of the invention and the other agent(s) are administered in a single composition.

The agents disclosed herein may be administered by any route, including intradermally, subcutaneously, orally, intraarterially or intravenously. Preferably, administration will be by the intravenous route. Preferably parenteral administration may be provided in a bolus or by infusion.

The concentration of a therapeutic agent to be administered in accordance with the invention will vary depending on several factors, including the dosage of the compound to be administered, the pharmacokinetic characteristics of the compound(s) employed, and the route of administration. The agent may be administered in a single dose or in repeat doses. Treatments may be administered daily or more frequently depending upon a number of factors, including the overall health of a patient, and the formulation and route of administration of the selected compound(s).

Preferably, said cancer treatment further comprises administration of a therapeutically effective amount of said therapeutic agent. The term "therapeutically effective amount" as used herein, refer to an amount of at least one agent or compound being administered that is sufficient to treat or prevent the particular disease or condition. The result can be reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in a disease. An appropriate "effective" amount in any individual case may be determined using techniques, such as a dose escalation study.

In certain embodiments, the diet is administered over a time period of at least 1 day, 2 days, 3 days, 4 days, 5 days, 6 days, 7 days, at least 2 weeks, 3 weeks, 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, or until a therapeutic endpoint is observed, e.g., tumor shrinkage is observed.

Where the diet the diet substantially devoid of serine comprises or consists of a dietary product, the dietary product is administered from one to ten times daily.

The invention also includes kits for detecting the presence of KRAS and/or MTAP in a sample. The kits of the invention have particular use in identifying subject who would benefit from a cancer treatment comprising a diet substantially devoid of serine. For example, the kit can include a compound or agent capable of detecting the expression or activity of a KRAS polypeptide or nucleic acid in a biological sample. The kit can include a compound or agent capable of detecting the expression or activity of a MTAP polypeptide or nucleic acid in a biological sample. The compound(s) or agent(s) can be packaged in a suitable container. The kit can further comprise instructions for using the kit to detect KRAS and/or MTAP protein or nucleic acid molecule.

In one aspect, the invention provides a kit for use in identifying a subject who would benefit from a cancer treatment comprising a diet substantially devoid of serine comprising:

a. an agent for determining the expression or activity of Kras; and b. reagents for the assay.

The kit may further comprise an agent for determining the expression or activity of MTAP.

In another aspect the invention provides a kit for use in identifying a subject who would benefit from a cancer treatment comprising a diet: i) substantially devoid of serine and/or ii) restricted in cysteine comprising:

a. an agent for determining the expression or activity of MTAP; and b. reagents for the assay.

In the kits of the invention, the agent may be an antibody or a nucleic acid molecule.

For antibody-based kits, the kit can include: (1) a first antibody (e.g., attached to a solid support) which specifically binds to to a polypeptide marker of the invention (e.g. KRAS or MTAP); and, optionally, (2) a second, different antibody which binds to either the polypeptide marker or the first antibody and is conjugated to a detectable agent.

For oligonucleotide-based kits, the kit can include: (1) a nucleotide probe, e.g., a detectably labeled primer, which hybridizes to a biomarker (e.g. KRAS or MTAP) nucleic acid molecule or (2) a pair of primers or amplifying a biomarker nucleic acid molecule.

The kits can also include components necessary for detecting the detectable agent (e.g., an enzyme or a substrate). The kits can also contain a control sample or a series of control samples which can be assayed and compared to the test sample contained.

The kit may also comprising instructions for use.

In one embodiment, when the kit determine KRAS expression or activity, the kit comprises comprising instructions that an increased level of Kras expression or activity in a biological sample compared to a control sample or compared to a predetermined reference level is indicative of non-responsiveness or insensitivity of the subject to said cancer treatment, and wherein a decreased level of Kras expression or activity in the biological sample compared to the control sample or compared to a predetermined reference level, or a level of Kras expression or activity which is substantially the same as the control sample or the predetermined reference level, is indicative of responsiveness or sensitivity to the subject to said cancer treatment.

In one embodiment, when the kit determines MTAP expression or activity, the kit comprises instructions that a decreased level of MTAP expression or activity in the biological sample compared to the control sample or compared to a predetermined reference level, or a level of MTAP expression or activity which is substantially the same as the control sample or the predetermined reference level, is indicative of responsiveness or sensitivity to the subject to said cancer treatment.

EXAMPLES

Example 1 (FIGS. 1, 2, 3, 4, 18, 19, 20, 21, 22 & 23)

Methods

Cell lines & Cell Culture.

DLD1, and SW480 cells were obtained from ATCC and authenticated using Promega GenePrint 10. iKRAS cells (iKRAS1, iKRAS3, AK196) were kindly supplied by Ron DePinho (Ying et al., Cell, 2012), (The University of Texas MD Anderson Cancer Center). Cell culture media were purchased from GIBCO, product numbers are shown in parenthesis. SW480 & iKRAS (DMEM—21969) and DLD1 (RPMI-1640-31870) were maintained in the stated media supplemented with 10% FBS (10270), penicillin-streptomycin & amphotericin with L-glutamine at final concentration of 2 mM. Stock iKRAS cells were grown in the presence of doxycycline 2 ug/ml (KRAS-ON) and in medium with/without doxycycline (KRAS-ON/OFF) for experiments. Cells were maintained in 37° C., 5% $CO_2$ humidified incubators. Cultured cells were routinely tested for mycoplasma using Mycoalert detection kit (Lonza).

Proliferation Assays.

iKRas cell were seeded in complete DMEM medium+doxycycline 2 ug/ml in 24-well plates and allowed to adhere overnight. Cells were then washed with PBS and received either assay medium with or without serine and glycine, with or without doxycycline 2 ug/ml. Triplicate wells were counted (using Casy TT cell counter, Innovatis, Roche Applied Science) at 48 h and 96 h, using a "time=0" plate to calculate relative cell number from time of medium change. Data presented are from three independent experiments.

Metformin In Vitro Assays

DLD1 and SW480 cells were seeded into 24-well plates and allowed to adhere overnight. Cells were washed with PBS and received either assay medium with or without serine and glycine, with or without metformin at the stated doses and allowed to grow for three days. Representative wells were photographed using a light microscope and counted using a Casy TT cell counter (FIG. 19d). For the dose-response experiment (FIG. 23e) cells were seeded in the same way, either in assay medium without serine and glycine, or in assay medium with low serine and glycine (10 uM), triplicate wells were counted after three days.

Organoid Culture.

ADF=Advanced DMEM F/12, with 2 mM glutamine, 1% of penicillin/streptomycin solution, 0.1% of AlbuMAX I BSA, 10 mM HEPES (all Gibco/Life Technologies). Adenomas were removed from the small intestine of mice and cut into smaller pieces and washed 5 times with ice cold PBS. Pieces were incubated in 5 mM EDTA for 10 min at 4° C. on a roller. Crypts were washed 2 times with ice cold PBS to remove EDTA and incubated in 10× trypsin for 30 min at 37° C. The crypt-enriched supernatant was collected and washed approximately 5 times with 5 ml ADF through mechanical pipetting. Crypts were pelleted via centrifugation at 1,200 rpm for 5 min. Crypts were re-suspended in growth factor reduced matrigel (BD Biosciences) and 20 µl was plated per well in a 12-well plate. Matrigel was allowed to solidify for 30 min in a 37° C. incubator before appropriate ADF was added supplemented with 0.05 µg/ml EGF and 0.1 µg/ml noggin (Total volume per well 1 ml). Crypts were split by harvesting in ice cold PBS and spun down at 600 rpm for 3 min. Supernatant was aspirated and the pellet dissociated with 100 µl ice cold PBS using mechanical pipetting. 5 ml of PBS was added to tube and spun own at 600 rpm for 3 min, repeated until supernatant was clear of debris. The final crypt pellet was re-suspended with growth factor reduced matrigel and plated as before. For serine/glycine starvation, amino acid free Advanced DMEM F/12 (Gibco/Life Technologies) was used to construct assay medium for organoids with or without serine and glycine, containing all other amino acids.

Diets.

From weaning, mice received 'normal chow' (Rat and Mouse Breeder and Grower, 801730, Special Diet Services, SDS, UK) and water ad libitum. On normal chow, dietary amino acids are derived from whole proteins contained in the raw ingredients (wheat, wheatfeed, barley, de-hulled extracted toasted soya, maize and fish meal), with a small amount of purified lysine added as a supplement. Two sets of experimental diets were used, both based on Baker Purified Amino Acid Diet (Hirakawa et al Nutr. Res. 1984) from TestDiet (Richmond, IN): "Diet 1-Control" contained all essential amino acids plus serine, glycine, glutamine, arginine, cystine, and tyrosine; "Diet 1-No Ser, No Gly" was the same as Diet 1-Control, but without serine and glycine, with the other amino acid levels increased proportionally to achieve the same total amino acid content. These "Diet 1"

formulations were used previously (Maddocks et al, Nature, 2013, and see under "Xenografts" below). "Diet 2—Control" contained all essential amino acids plus serine, glycine, glutamine, arginine, cystine, tyrosine, alanine, proline, glutamate and asparagine; "Diet 2—No Ser, No Gly/Diet 2—SG-free" was the same as Diet 2-Control, but without serine and glycine, with the other amino acid levels increased proportionally to achieve the same total amino acid content. "Diet 2" formulations were used for the Eµ-Myc-Tigar$^{-/-}$ cohort (FIG. 19f). All other cohorts received the previously published "Diet 1" formulations.

Mice.

All animal work was carried out in line with the Animals (Scientific Procedures) Act 1986 and the EU Directive 2010 and was sanctioned by the local ethical review process (University of Glasgow). Mus Musculus cohorts were housed in a barriered facility proactive in environmental enrichment. The Eµ-Myc11, ApcMin/+, Lgr5creER; Apcfl/fl and Pdx1cre; KrasG12D; Trp53fl/+ or Trp53R172H/+ mice/models have been previously described. Mixed male and female populations were used for each genotype. The number of mice (or number of samples from individual mice) is shown in each Figure/Figure Legend. Eµ-Myc, and ApcMin/+ mice were at least 20 generations C57BL/6J. Eµ-Myc; Tigarfl/fl mice were at least 50% C57BL/6J. Mice were put on the appropriate diet at the following times: Eµ-Myc pure bred 60 days post-natal, Eµ-Myc; Tigarfl/fl 55 days post-natal, ApcMin/+80 days post-natal, Lgr5creER; Apcfl/fl 7 days post-induction, Pdx1cre; KrasG12D; Trp53fl/+ or Trp53R172H/+60 days post-natal. Recombination by Lgr5creER was induced with two intraperitoneal injections of 120 mg/kg tamoxifen, with a day's rest between the injections. For the phenformin experiment, Eµ-Myc mice were gavaged daily with 100 mg/kg mouse body weight, starting the same day as the diet change. For the metformin experiment, ApcMin/+ mice were given 200 mg/kg/day in their drinking water, starting 4 days after the diet change. All mice were taken to clinical end-point. Intestines from ApcMin/+ mice were fixed in methacarn (4:2:1 ratio of methanol, chloroform, acetic acid) to facilitate scoring of tumour number and area (width×length).

Sample sizes for mouse studies were estimated from previous experience with these models where potential differences in survival are tested by Mantel-Cox (Log Rank) analysis. After data was collected for the first experimental groups (e.g. Eµ-Myc and APCMin/+ on diet only) subsequent groups were reduced in size to minimize animal numbers used (e.g. Phenformin and Metformin treatment groups. In all experiments, only mice with overt phenotype at time of enrolment into the study were excluded (i.e. not enrolled): e.g. enlarged lymph nodes or signs of enlarged thymus in the Eµ-Myc cohorts, anemia in the APCMin/+ cohorts. Animals that died due to illness unrelated to tumour(s) were included as censored observations. Mice were allocated into the experimental groups according to a randomized block design: as mice became available through breeding, they were split into blocks based on gender and then randomly assigned to a treatment. Care was taken to keep the male/female ratio similar, in order to remove gender as a potential source of variability. The investigator allocating mice to the experimental groups and collecting the endpoint data was not blinded.

Liquid Chromatography Mass Spectrometry (LCMS).

Samples were prepared in cold (−20° C.) lysis solvent (LS) consisting of methanol, acetonitrile, and $H_2O$ (50:30:20). Serum samples of 10 µl were added to 490 µl of LS and vortexed, precipitated protein was cleared by centrifugation. Organoid extracts were prepared by washing wells with PBS then adding 250 µl LS per well and shaking at 4° C. for 10 minutes, LS was removed from wells and then proteins cleared by centrifugation. Tissue samples were snap frozen and stored at −80° C. Prior to lysis, frozen samples were weighed then homogenized in 1 ml cold LS using a Precellys homogeniser (Bertin Technologies). Lysates were cleared of protein by centrifugation and lysate concentrations were normalized post-homogenisation with LS based on weight. Extracts were analysed on an LCMS platform consisting of an Accela 600 LC system and an Exactive mass spectrometer (Thermo Scientific). A SeQuant ZIC-pHILIC column (2.1 mm×150 mm, 5 µm) (Merck) was used to separate the metabolites with the mobile phase mixed by A=Ammonium carbonate 20 mM (adjusted to pH 9.4) and B=Acetonitrile. A gradient program starting at 20% of A and after 2 mins linearly increasing to 80% at 17 min was used followed by washing and re-equilibration steps. The total run time of the method was 25 min. The LC stream was desolvated and ionised in the HESI probe. The Exactive mass spectrometer was operated in full scan mode over a mass range of 75-1,000 m/z at a resolution of 50,000 with polarity switching. The raw data was analysed by LCquan (Thermo Scientific) and MZMine 2.10 for metabolite identification and quantification.

Western Blot.

Western blots on cells were performed as described previously (Maddocks et al, Nature, 2013; Labuschagne et al., Cell. Rep., 2014; Maddocks et al, Mol. Cell, 2016), briefly, whole-cell protein lysates were prepared in RIPA-buffer supplemented with complete protease inhibitors (Roche), sodium orthovanadate, and sodium fluoride (both Sigma). Tissue samples were lysed in RIPA buffer supplemented with protease and phosphatase inhibitor cocktail (Pierce/Thermo Scientific) using a TissueLyser II (Qiagen). Lysates were cleared by centrifugation and separated using precast 4-12% 'NuPAGE' or 'Bolt' gels (Invitrogen, Life Technologies) and transferred to nitrocellulose membranes. Proteins were detected and quantified using a Li-Cor Odyssey Infrared scanner and software (Li-Cor Biosciences). Secondary antibodies for the relevant species were IRDye680 and IRDye800 conjugated (Li-Cor Biosciences). Primary antibodies used were: PHGDH (Sigma Life Science, HPA021241), PSAT1 (Novus Biologicals, NBP1-32920), PSPH (Santa Cruz, sc-98683), Actin 1-19-R (Santa-Cruz, sc-1616-R), pERK [Phospho-p44/p42 MAPK (Erk1/2) (Thr202/Tyr204)] (Cell Signalling Technology 9101), AMPKa1 (R&D Systems, AF3197) and Phospho-AMPK T172 (Cell Signalling Technology 2535).

qRT-PCR.

RNA was extracted using RNeasy kit with DNase (both Qiagen) to remove DNA. qRT-PCR was performed as described previously (Maddocks et al, Nature, 2013) using an Applied Biosystems 7500 Fast Real-Time PCR system with SYBR Green master mix (Applied Biosystems). Primers (5'-3'): Mouse PHGDH For TGGCCTCGGCAGAAT-TGGAAG; Mouse PHGDH Rev TGTCATTCAGCAAGC-CTGTGGT; Mouse PSAT1 For GATGAACATCCCAT-TTCGCATTGG; Mouse PSAT1 Rev GCGTTATA-CAGAGAGGCACGAATG; Mouse PSPH For GAGATG-GAGCTACGGACATGGAAG; Mouse PSPH Rev CTCCTCCAGTTCTCCCAGCAGCTC. Mouse ActinB purchased from Primer Design (HK-SY-mo-900 ACTB). Sequences synthesized and purified by Eurofins MWG Operon.

Statistics.

Statistical comparisons for survival data were calculated with Graphpad Prism (v6) software using Mantel-Cox (Log Rank) test. T-tests were either performed using Microsoft excel (v14.6.1) or Graphpad Prism (v7). Type-1/paired (samples taken from the same animal) and type-2/unpaired (samples taken from different animals) T-tests were used. Where no prediction was made about the direction of potential difference a two-sided/2 tailed T-test was used (e.g. across all amino acid levels in serum samples, FIG. 21). Where pre-existing data supported a prediction in the direction of difference between samples a one-sided/one tailed T-test was used (e.g. de novo serine synthesis, FIG. 2d). Where data presented is the mean of individual data-points error bars are STDEV, where data is a mean of means error bars are SEM. In each instance the relevant type of T-test or error bar is specified in the figure legend. Where T-tests were performed with multiple comparisons, P values were corrected using the Holm-Sidak method using Graphpad Prism (v7) software.

Xenografts

Bilateral subcutaneous injections of 3×106 HCT116 cells were carried out on 8 week CD-1-Foxn1nu female mice (Charles River); p53+/+ on right flank and p53−/− (1ex) on the left. Immediately following injection mice were placed either on control diet (n=10) (containing serine and glycine as part of the amino-acid mix) or diet deficient in serine & glycine (n=10) (Test Diet, International Product Supplies)—formulations as follows:

Control diet ingredients: sucrose (25.9%), corn starch (41.8%), corn oil (5.0%), Baker amino acid vitamin mix (0.2%), Baker amino acid mineral mix (10.0%), sodium bicarbonate (1.0%), DL-alpha tocopheryl acetate (0.004%), ethoxyquin (preservative, 0.019%), choline chloride (0.1%), amino acid premix (16.0%). Amino acid pre-mix: L-arginine-HCL (1.60%), L-cystine (0.64%), L-glutamine (1.60%), glycine (1.33%), L-histidine-HCL (0.80%), L-isoleucine (1.07%), L-leucine (1.60%), L-lysine-HCL (1.87%), L-methionine (0.80%), L-phenylalanine (1.07%), L-serine (1.33%), L-threonine (1.07%), L-tryptophan (0.27%), L-tyrosine (0.53%), L-valine (1.07%). The serine- and glycine-free diet has the same basic formulation as the control diet, but the amino acid mix lacks serine and glycine. Serine- and glycine-free diet ingredients: sucrose (25.9%), corn starch (41.8%), corn oil (5.0%), Baker amino acid vitamin mix (0.2%), Baker amino acid mineral mix (10.0%), sodium bicarbonate (1.0%), DL-alpha tocopheryl acetate (0.004%), ethoxyquin (preservative, 0.019%), choline chloride (0.1%), amino acid premix (16.0%). Amino acid pre-mix: L-arginine-HCL (1.60%), L-cystine (0.64%), L-glutamine (1.60%), L-histidine-HCL (0.96%), L-isoleucine (1.28%), L-leucine (1.92%), L-lysine-HCL (2.24%), L-methionine (0.96%), L-phenylalanine (1.28%), L-threonine (1.28%), L-tryptophan (0.32%), L-tyrosine (0.64%), L-valine (1.28%).

The diets had equal calorific value and equal total amino acid content. Animals were housed in sterile IVC cages, monitored thrice weekly and humanely sacrificed when tumours reached clinical endpoint of predetermined size (volume=(length×width2)/2) or ulceration. All animal work was approved by the Ethical Review Process (University of Glasgow) and undertaken in line with the UK Animals (Scientific Procedures) Act of 1986 (PPL 60/4181) and the EU directive 2010.

Results

We tested two mouse models of pancreas cancer driven by activation of KRas and either loss ($Kras^{G12D}p53^{+/-}$) or mutation ($Kras^{G12D}p53^{R172H}$) of p53. Surprisingly, no significant change in survival was observed in response to serine/glycine free diet in either model (FIGS. 1a & b), despite a clear decrease in serum serine and glycine levels (FIGS. 3a & b). Intra-venous injection of $^{13}C$-$^{15}N$-labeled serine revealed that serine uptake was comparable in pancreatic normal and tumour tissue, whereas intestinal tumours in the APCmin model took up significantly more serine (as measured by label in serine and glycine derived from serine) compared to normal tissue (FIG. 1c). These results are consistent with an increased requirement of APCmin tumours for exogenous serine, and thus their sensitivity to dietary serine restriction. The pancreatic tumours, however, appeared to be less reliant on exogenous serine, explaining their resistance to the diet.

An obvious difference between the lymphoma/intestinal tumour models and the pancreatic models is the presence of activated KRas in the latter. Activated Ras has been shown to increase the ability of cells to access extracellular protein through macropinocytosis, a mechanism that could make cells less dependent on free circulating serine levels.

However, overexpression of the SSP pathway enzymes can also remove dependence on extracellular serine, prompting us to examine the effect of $KRas^{G12D}$ expression on the ability of these cells to carry out de novo serine synthesis. Using pancreatic cells with doxycycline inducible $Kras^{G12D}$ we found a consistent decrease in SSP enzyme expression at both RNA and protein level following down-regulation of $KRas^{G12D}$ (FIGS. 1d & e). Cells expressing $Kras^{G12D}$ were completely resistant to serine and glycine starvation. Inactivation of $Kras^{G12D}$ slowed the proliferation rate of these cells in complete medium and, importantly, cells without $Kras^{G12D}$ regained sensitivity to serine starvation, showing a further decrease in proliferation in serine and glycine free medium (FIG. 1f).

Figure 28:
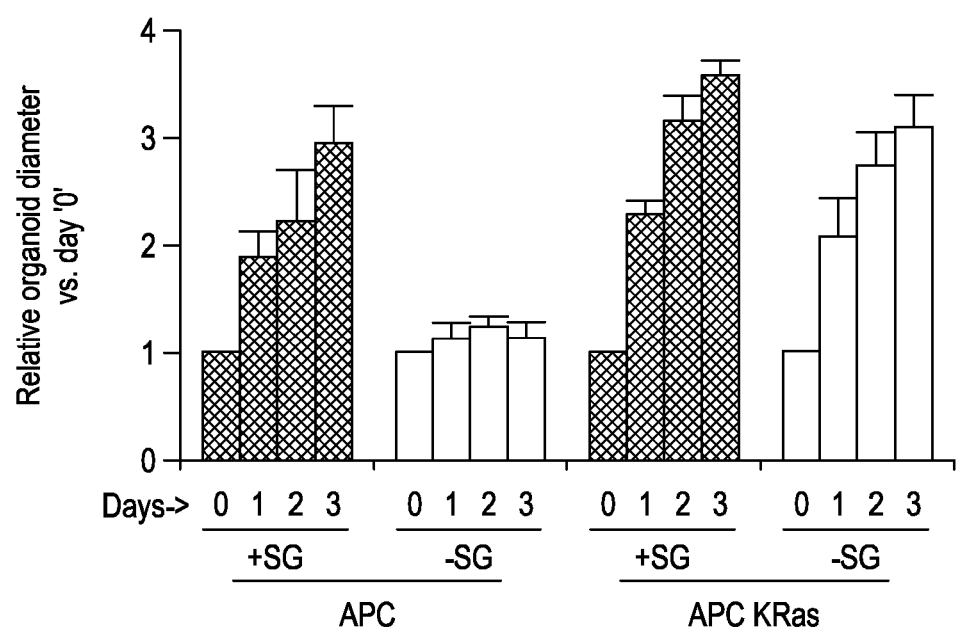
FIG. 28. Tumour-organoids expressing Kras were more resistant to serine and glycine starvation. $Villin^{creER}$; $APC^{fl/fl}$ and $Villin^{creER}$; $APC^{fl/fl}$; $KRas^{G12D/+}$ intestinal tumour organoids (from n=3 mice per genotype) were grown without serine & glycine for five days then dissociated and seeded into complete growth medium. Organoid diameter was measured for each day in complete (recovery) medium. Data are averages of organoids from three mice, obtained in a single experiment. Error bars=SEM
Figure 29:
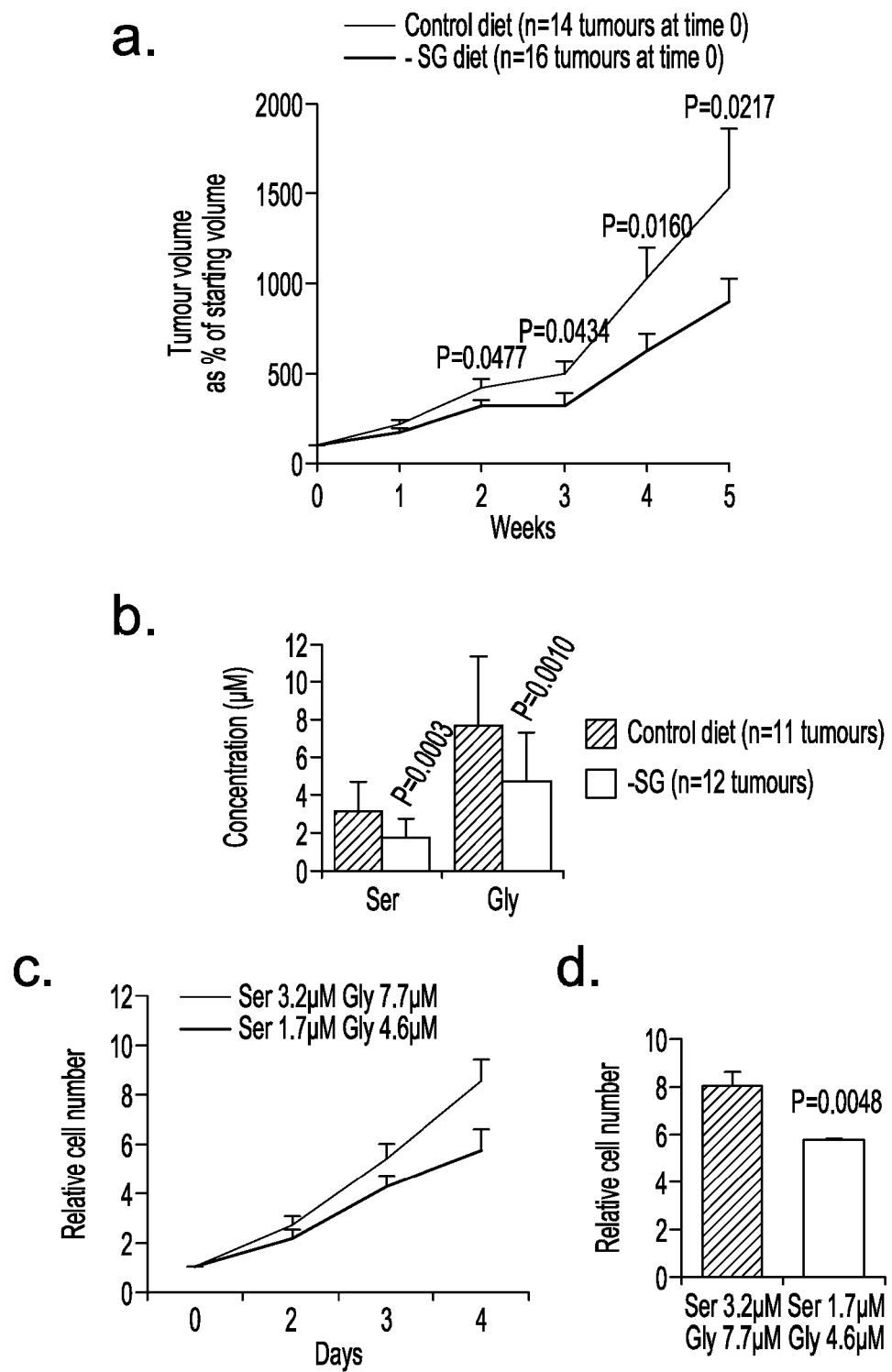
FIG. 29 shows that a diet devoid in glycine and serine decreases growth of xenograft tumours already formed in vivo, decreases intra-tumour serine and glycine levels and that such levels translate to slower cancer cell proliferation in vitro a. HCT116 cells were injected bilaterally (3×10^6 per flank) and allowed to form tumours. Once tumours were visible and measurable by calipers mice were transferred to control diet or serine and glycine free diet (−SG). Tumours were measured three times per week and average weekly tumour volume is plotted, Error bars=SEM. P values were calculated by T-test (unpaired, one tail). b. HCT116 tumours (taken at clinical end-point) were analysed by LCMS for absolute concentration of serine and glycine (1-3 pieces of each tumour were analysed). Data are averages, bars are STDEV. P values were calculated by T-test (unpaired, one tail). c. HCT116 cells were grown in vitro (24-well plates) in the intra-tumoural serine and glycine concentrations displayed in Medium was replaced every 24 hours and cell counts were performed on the stated days. Data are averages of 12 replicate wells for each condition from an individual experiment, error bars=STDEV. d. HCT116 cells were grown in vitro (24-well plates, 12 replicate wells for each condition) in the intra-tumoural serine and glycine concentrations displayed in Medium was replaced every 24 hours and cell counts were performed after four days. Data are averages of three independent experiments, error bars=SEM. P values were calculated by T-test (unpaired, one tail).

We also tested whether $Kras^{G12D}$ expression could confer resistance to serine sensitive intestinal tumour cells, using the organoid culture model. APCmin intestinal organoids grow as spheres in vitro, and consistent with our in vivo studies the growth of these organoids was impeded by serine and glycine removal (FIG. 2a). By contrast APCmin/$Kras^{G12D}$ organoids were much less affected by serine starvation (FIG. 2a). Furthermore, growth in serine and glycine free conditions for five days severely impaired the ability of APCmin organoids to recover after re-seeding into complete medium, whereas $Kras^{G12D}$ expressing organoids made a rapid recovery (FIG. 2b and FIG. 28). These phenotypic changes were reflected by higher basal expression of SSP enzymes in the $Kras^{G12D}$ expressing intestinal cells (FIG. 2c). The SSP utilizes glycolytic intermediates to make serine, so to test SSP activity in these cells, we grew organoids in medium containing $^{13}C$-labeled glucose and measured levels of labelled glucose and serine (synthesised from glucose) (FIG. 2d). While labelled glucose levels were comparable in APCmin and APCmin $Kras^{G12D}$ cells, indicating equal ability to take up glucose in these cells, labelled serine levels were significantly higher in the $Kras^{G12D}$ expressing cells, supporting increased rates of serine synthesis in these cells (FIG. 2d).

Analysis of serum amino acid levels in the GEM models for PDAC showed that the diet significantly decreased the systemic levels of serine and glycine in both models (FIGS. 3a & b), whereas other amino acids levels were either unchanged or showed minor/inconsistent variation. Despite this systemic decrease in serine and glycine the PDAC tumours were resistant to serine/glycine starvation, due to their ability to up-regulate de novo serine synthesis as described above (FIGS. 1 & 2). In contrast, tumours formed in nude mice from a xenografted human colorectal cancer cell line (HCT116) were sensitive to dietary serine/glycine starvation. In the xenograft model the serine/glycine free diet caused a significant decrease in tumour volume (FIG. 4a) and significantly increased the survival of the mice (FIG. 4b).

Figure 20:
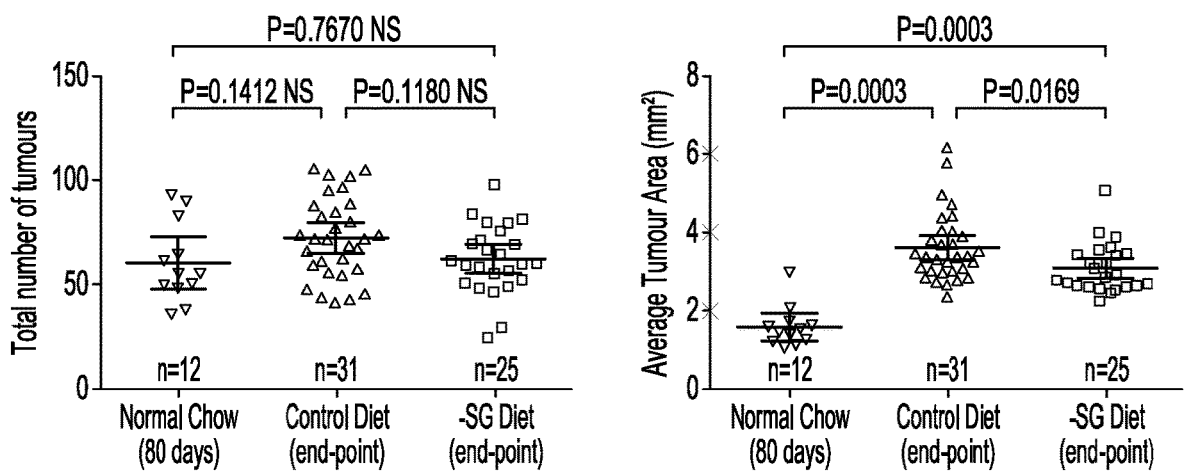
FIG. 20. Effect of serine and glycine free diet on tumour burden in APC$^{min/+}$ mice. APC$^{min/+}$ mice received normal chow until 80 days of age, then were transferred to either a control diet (containing serine and glycine) or a matched diet lacking serine and glycine (No Ser, No Gly; −SG) until clinical end-point (intestinal tumour related survival). Post-mortem tumour measurement was performed on intestinal tissue at time of diet change (80 days) or clinical endpoint. P values calculated by T-test (unpaired, two tails, with correction for multiple comparisons).
Figure 21:
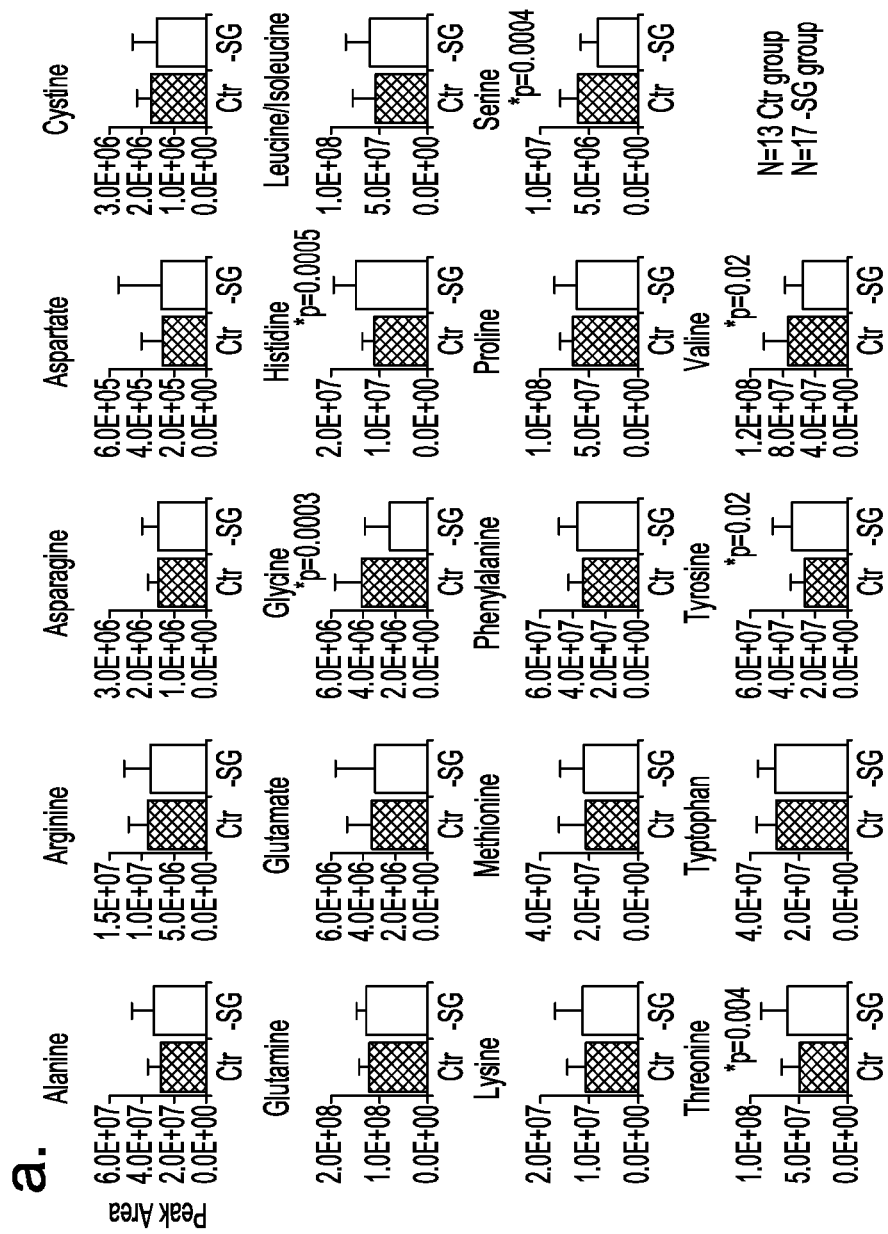
FIG. 21. Effect of serine and glycine free diet on serum amino acids a. Eμ-myc and b. $APC^{min/+}$ mice received normal chow until ~60 & ~80 days of age respectively, then were transferred to either a control diet containing serine and glycine (Ctr) or a matched diet lacking serine and glycine (−SG) until clinical end-point. Serum isolated from terminal bleeds was analysed by LCMS. Relative quantity of metabolites are shown (x-axis=peak area). Error bars=STDEV. P values were calculated by T-Test (unpaired).
Figure 21:
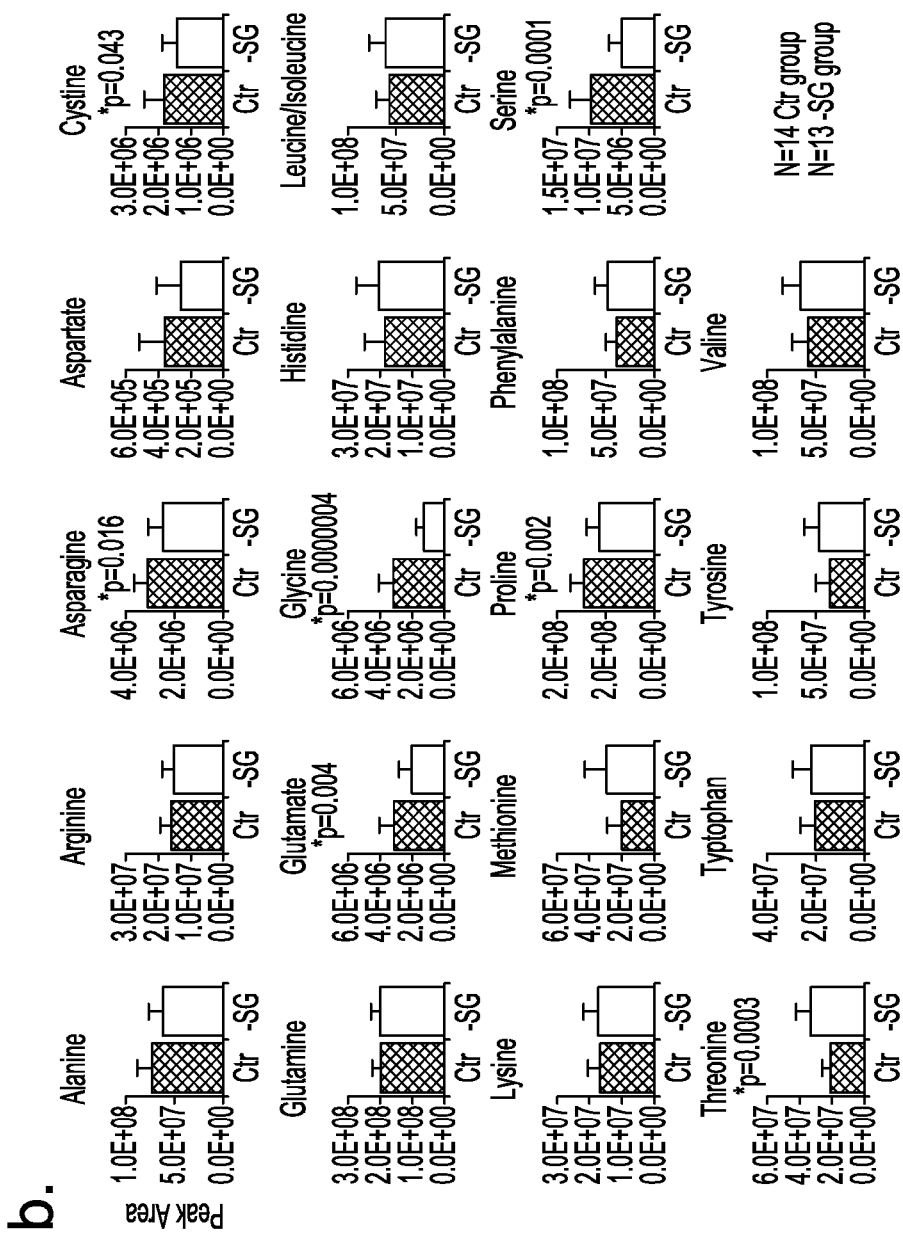
Figure 22:
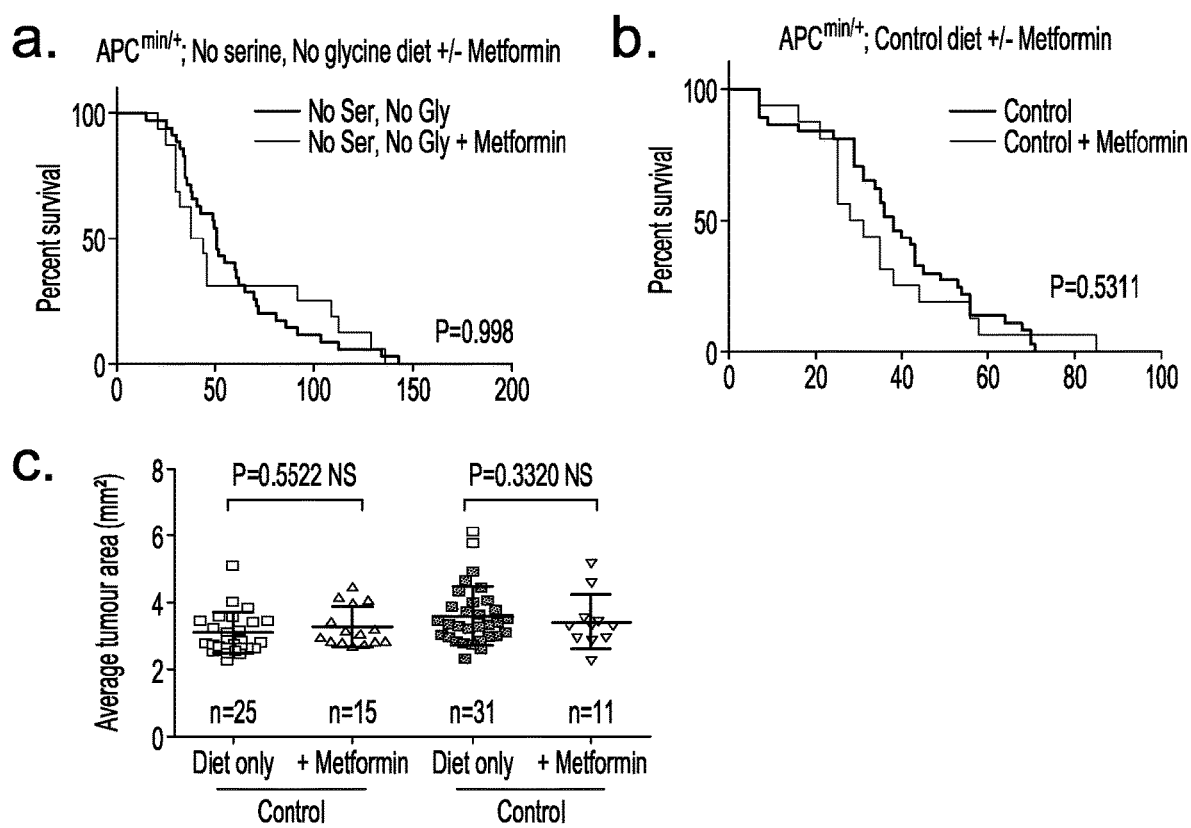
FIG. 22. Metformin treatment did not enhance the anti-cancer effect of serine and glycine free diet in $APC^{min/+}$ mice. Mice were transferred to serine and glycine free diet (No Ser, No Gly) (a) or Control diet (b) at ~80 days of age, then four days later received Metformin (Metf.) 200 mg/kg/day in drinking water. Intestinal tumour-related survival calculated from change of diet, not birth. P value calculated by Mantel-Cox test. c. Comparison of diet-only tumour burden data with metformin+diet tumour burden. Post-mortem tumour area measurement was performed on the small intestine (SI) of $APC^{min/+}$ mice. P values were calculated by T Test (unpaired, two tails) "Diet only" data is replicated from FIG. 20.
Figure 23:
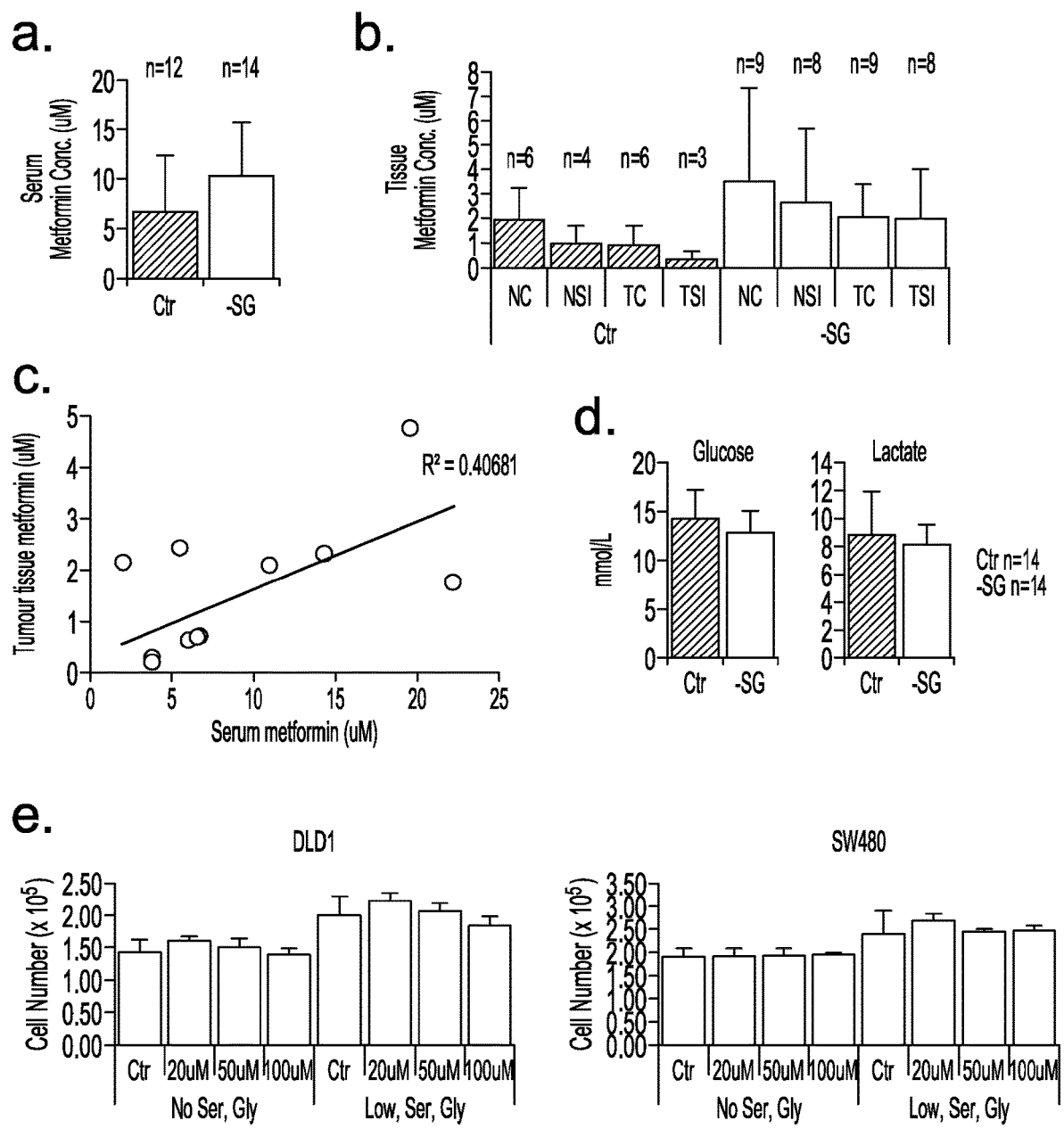
FIG. 23. In vivo metformin levels had little impact on systemic metabolism and were too low to potentiate the anti-cancer effect of the serine & glycine free diet. a. $APC^{min/+}$ mice were transferred to Control or serine and glycine free diet (−SG) then received Metformin 200 mg/kg/day in drinking water. Serum isolated from terminal bleeds was analysed by LCMS. Error bars=STDEV. b. Tissue samples from metformin treated mice were analysed by LCMS. NC=normal colon, NSI=normal small intestine, TC=tumour colon, TSI=tumour small intestine. Error bars=STDEV c. For mice where matching serum and tumour (SI or colon) tissue samples were available (Ctr diet n=7, −SG diet n=6), serum versus tumour metformin concentrations are plotted. Metformin concentrations were determined in all samples using a six-point calibration curve using the relevant biological matrix (tissue/serum). d. Serum from $APC^{min/+}$ mice treated with metformin was analysed for glucose and lactate levels using an Agilent 2100 Bioanalyser. e. Human colorectal cancer cells DLD1 and SW480, which express truncated APC, were grown in varying concentrations of Metformin either without serine and glycine (No Ser, No Gly) or in low serine and glycine (10 μM) for three days after which cell number was counted. Data are averages of triplicate wells, error bars=STDEV.

To assess whether the observations made in the xenograft model translated to autochthonous tumours we used well-established models for lymphoma (based on Eµ-Myc expression) and intestinal tumours (based on defective APC expression). Mice were transferred from normal chow diet to experimental diet 60-80 days after birth, following the development of premalignant lesions (adenoma initiation occurs days after birth $APC^{Min/+}$ mice, Eµ-Myc mice develop pre-neoplastic lesions within 28-42 days after birth), to mimic a therapeutic (rather than preventative) intervention. In both genotypes the serine and glycine free diet significantly extended survival (FIGS. 18a & b). Tumour area in $APC^{Min/+}$ mice indicated there was also a small but significant trend for smaller tumour size in mice on the serine/glycine free diet at clinical endpoint, but no significant difference in the number of tumours in mice on the serine/glycine free diet at clinical endpoint (FIG. 20).

Liquid chromatography-mass spectrometry (LCMS) analysis of serum samples indicated that diet reproducibly caused a significant decrease in serine and glycine levels with minimal or inconsistent impact on other amino acids (FIGS. 18c & d, FIGS. 21a & b). These changes translated to a reduction in serum serine and glycine from around 150 µM on control diet, to 65 µM on the serine and glycine free diet (FIG. 18e). We further validated the survival effect of the diet using an inducible intestinal tumour model (Lgr5-creER $APC^{fl/fl}$); in this case mice were transferred to diet a week after tumour induction was initiated. Again, the diet caused a significant increase in survival compared to control diet (containing purified amino acids) or normal chow (containing whole protein as a source of amino acids) (FIG. 18f).

Serine starvation activates de novo serine synthesis, diverting glycolytic intermediates away from energy production. Cells respond by increasing OXPHOS to maintain ATP levels, and inhibiting OXPHOS can enhance the anti-proliferative effect of serine starvation. To test whether these observations would translate to an autochthonous tumour model we combined serine and glycine starvation with the biguanide phenformin (a complex I inhibitor) in Eµ-Myc mice. A maximal dose of phenformin (100 mg/kg/day) was tolerated by mice on normal diet, but elicited significant toxicity (symptoms resembling dyschezia) in mice receiving the serine and glycine deficient diet. While this forced us to curtail recruitment into this study, mice that were already recruited and did not succumb to toxicity (7/14) did not suffer further adverse effects. These mice were maintained on diet with phenformin and showed a trend for improved survival compared to animals on the serine and glycine free diet alone. However, due to initial toxicity, too few mice survived to make this effect statistically significant (FIG. 19a). These results are consistent with a previous study showing cooperation between serine deprivation and biguanide treatment in a tumour allograft system.

To further explore the potential synergy between biguanide treatment and serine starvation we turned to metformin, which has lower toxicity, is widely used in the clinic as an anti-diabetic agent and is being trialled as an anti-cancer agent. While systemic availability of oral metformin is generally poor, some tissues (including the intestine) express OCT1 transporters that facilitate metformin uptake, making $APC^{Min/+}$ mice a viable model. Guided by previous studies, we selected dose of metformin (200 mg/kg/day) in mice equivalent (by body surface-area calculation) to a daily human dose of 1 g/day. Doses of 0.5-1 g/day have been used in multiple clinical trials of metformin in colorectal cancer, hence we selected a clinically relevant dose, but chose a sub-maximal dose to avoid toxicity seen with phenformin. However, we failed to detect a significant impact of metformin on the survival of $APC^{Min/+}$ mice—although the beneficial effect of serine starvation persisted (FIG. 19b & FIGS. 22a & b). Intriguingly, metformin actually increased the number of tumours present in both diet groups (statistically significant for the serine and glycine free diet group) (FIG. 19c), without a substantial change in average tumour area (FIG. 22c). While this result was surprising given the ability of metformin (1000 uM) to synergise with serine starvation in intestinal tumour organoids derived from a $Villin^{creER}$; $APC^{fl/fl}$ mouse (FIG. 19d), the tumour-organoid data also showed that low dose metformin antagonizes serine and glycine starvation, protecting tumour cells from starvation (FIG. 19d). These dose dependent effects of metformin (to either protect from or potentiate the effects of serine and glycine starvation) are likely to be related to the effect of metformin on reactive oxygen species (ROS) levels, which decrease with low dose metformin, but increase with high dose metformin (FIG. 19e).

To investigate why metformin treatment didn't appear effective in serine/glycine-starved mice, we analysed serum and tissues by mass spectrometry. Analysis of serum and tissue from metformin treated mice (FIGS. 23a, 23b & 23c) showed that metformin levels were relatively low, and in the range expected to antagonize (rather than potentiate) the anti-proliferative effect of serine and glycine starvation. Analysis of serum glucose and lactate showed that these low levels of metformin had minimal impact on systemic metabolism (FIG. 23d). At these concentrations metformin did not have a synergistic effect with serine/glycine starvation APC deficient organoids (FIG. 19d, as discussed above) or in APC-truncated colorectal cell lines, at 20 µM showing a trend for increased cell number (FIG. 23e). Metformin has long-established anti-oxidant properties including up-regulation of thioredoxin, and we have shown that anti-oxidants improve cell survival during serine and glycine starvation by protecting from ROS. The present study therefore suggests that despite a clinically relevant dose and tissue penetration, metformin levels were too low to inhibit tumour growth. This contrasts with a previous study showing a moderate decrease in tumour area (without change in tumour number) in $APC^{Min/+}$ mice on metformin, albeit at higher dose.

We showed previously that serine depletion makes cells in culture more sensitive to ROS, so to test directly whether increasing ROS levels in vivo could enhance the anti-tumour effect of the serine depleted diet, we used mice deleted of Tigar. The TIGAR protein has been shown to support tumour development by limiting ROS. While Eµ-Myc expression on this mixed strain background caused mice to die of lymphoma more rapidly than the pure Bl6 Eµ-Myc (shown in FIG. 18a), as expected, we found increased survival following Tigar deletion (FIG. 19f). Importantly, a combination of Tiger deletion with serine and glycine free diet had an improved effect, producing a significant overall increase in survival (FIG. 19f). These data support the concept that increasing tumour ROS levels will result in improved survival when combined with serine and glycine free diet. As many chemotherapeutics and radiotherapy induce ROS, there is excellent potential to combine this diet with standard anti-cancer treatments.

Figure 5:
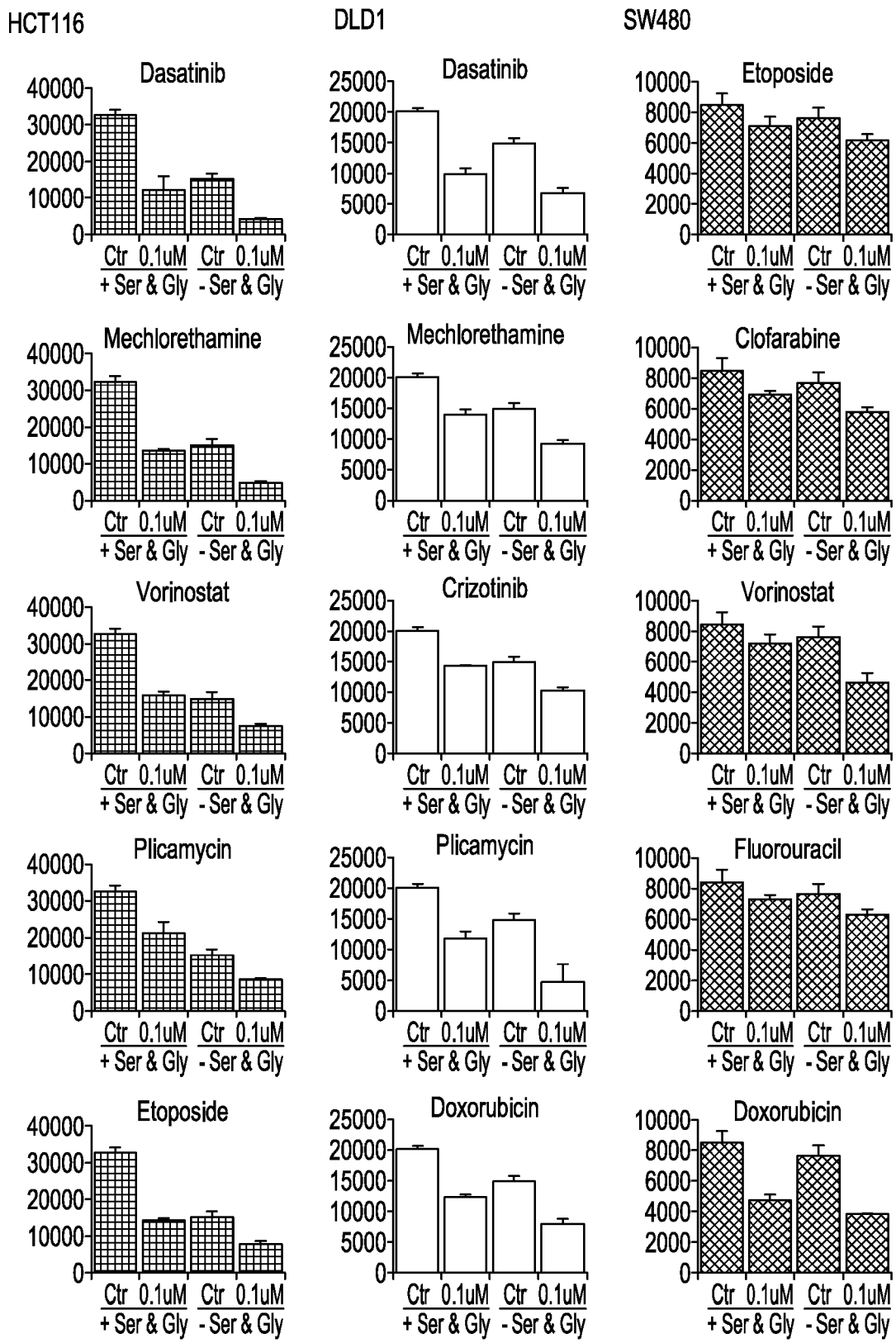
FIG. 5. Effect of serine starvation on the growth inhibitory effects of anti-cancer drugs with HCT116, DLD1 and SW480 cell lines. A significant proportion of the chemotherapies show an enhanced anti-proliferative effect when given at the same time as serine and glycine starvation.

Example 2 (FIG. 5 and Table 1)

Methods

HCT116 (6,000 cells per well), DLD1 (6,000 cells per well) and SW480 (10,000 cells per well) cells were seeded in 96-well plates either in medium containing or lacking serine and glycine (but containing all other amino acids). After 6 hours the stated drugs at the stated doses (ranging from 0.1-10 uM) were added to the plates and cells were incubated for a further 48 hours. After this time cells were fixed in formalin (4%) solution and stained with DAPI nuclear stain. Cell counts were performed using an Operetta system. The results are shown in FIG. 5.

Human cell lines HCT116, DLD1 and SW480 were seeded into 96-well plates either in complete medium containing serine, glycine and cysteine at 100 uM, with all other amino acids present, or low serine, glycine, cysteine (17-23 uM) medium with all other amino acids present. After 6 hours the stated chemotherapeutic agents were added (at doses of 0.01, 0.1 and 1 uM) to the wells and cells were incubated for a further 48 hours. After this time cells were formalin fixed and stained with a fluorescent nuclear stain for cell counting on an automated (Operetta) plate reader. Cell number data was used to derive a synergy score to calculate which drugs had a synergistic (i.e. greater than additive effect) when given in combination with low serine/glycine/cysteine (see below). The results are shown in Table 1.

The data shown in FIG. 5 demonstrate that multiple anti-cancer chemotherapeutic agents (from multiple drug classes) have enhanced anti-proliferative activity in human cancer cells when combined with serine and glycine starvation. This data therefore suggest that combining a serine and glycine free diet with conventional chemotherapies in cancer patients could enhance the anti-tumour activity of the chemotherapies, and/or allow them to be used at lower doses.

Table 1 shows the average synergy score for three colorectal cells lines for a combination of the specified drug with a reduction of serine, glycine and cysteine in the medium.

TABLE 1

| DRUG | SYNERGY SCORE |
| --- | --- |
| Tamoxifen citrate | 9.12 |
| Cetuximab | 7.68 |
| Metformin | 7.53 |
| Erlotinib hydrochloride | 6.66 |
| Dasatinib | 6.61 |
| Estramustine phosphate sodium | 5.81 |
| Daunorubicin hydrochloride | 5.29 |
| Vorinostat | 4.94 |
| Cabozantinib | 4.51 |
| Idelalisib | 4.05 |
| Vinorelbine tartrate | 3.96 |
| Temsirolimus | 3.90 |
| Hydroxyurea | 3.88 |
| Melphalan hydrochloride | 3.53 |
| Valrubicin | 3.36 |
| Everolimus | 3.33 |
| Amifostine | 3.01 |
| Tretinoin | 2.85 |
| Fludarabine phosphate | 2.76 |
| Dacarbazine | 2.65 |
| Vemurafenib | 2.57 |

TABLE 1-continued

| DRUG | SYNERGY SCORE |
| --- | --- |
| Ceritinib | 2.56 |
| Arsenic trioxide | 2.52 |
| Temozolomide | 2.47 |
| Dexrazoxane | 2.31 |
| Regorafenib | 2.29 |
| Sorafenib | 2.26 |
| Exemestane | 2.14 |
| Romidepsin | 2.03 |
| Bosutinib | 1.95 |
| Capecitabine | 1.94 |
| Lenalidomide | 1.94 |
| Allopurinol | 1.85 |
| Streptozocin | 1.81 |
| Altretamine | 1.81 |
| Cisplatin | 1.79 |
| Doxorubicin hydrochloride | 1.76 |
| Nilotinib | 1.70 |
| Imiquimod | 1.68 |
| Carfilzomib | 1.65 |
| Vandetanib | 1.61 |
| Vismodegib | 1.53 |
| Fluorouracil | 1.48 |
| Olaparib | 1.46 |
| Mitotane | 1.43 |
| Anastrozole | 1.43 |
| Epirubicin hydrochloride | 1.40 |
| Raloxifene | 1.38 |
| Lapatinib | 1.36 |
| Pazopanib hydrochloride | 1.32 |
| Fulvestrant | 1.26 |
| Uracil mustard | 1.21 |
| Afatinib | 1.18 |
| Ifosfamide | 1.16 |
| Etoposide | 1.07 |
| Triethylenemelamine | 1.03 |
| Ponatinib | 1.00 |

The data shown in Table 1 show that human cancer cells exposed to low concentrations of serine, glycine and cysteine (as would occur in vivo when a serine & glycine free, or serine, glycine & cysteine free diet is taken) are more sensitive to the anti-proliferative effects of multiple chemotherapeutic agents. For the chemotherapeutic agents listed in Table 1 there is a synergistic effect on anti-proliferative activity when combined with low serine, glycine & cysteine; i.e. the anti-proliferative effect of each agent in combination with amino acid limitation is greater that than the sum of the anti-proliferative the agent given alone, or the effect of amino acid limitation alone. This data therefore suggest that combining a serine and glycine/serine, glycine and cysteine free diet with conventional chemotherapies in cancer patients could enhance the anti-tumour activity of the chemotherapies, and/or allow them to be used at lower doses.

Example 3 (FIGS. 6, 7, 10 & 11)

Methods

Figure 6:
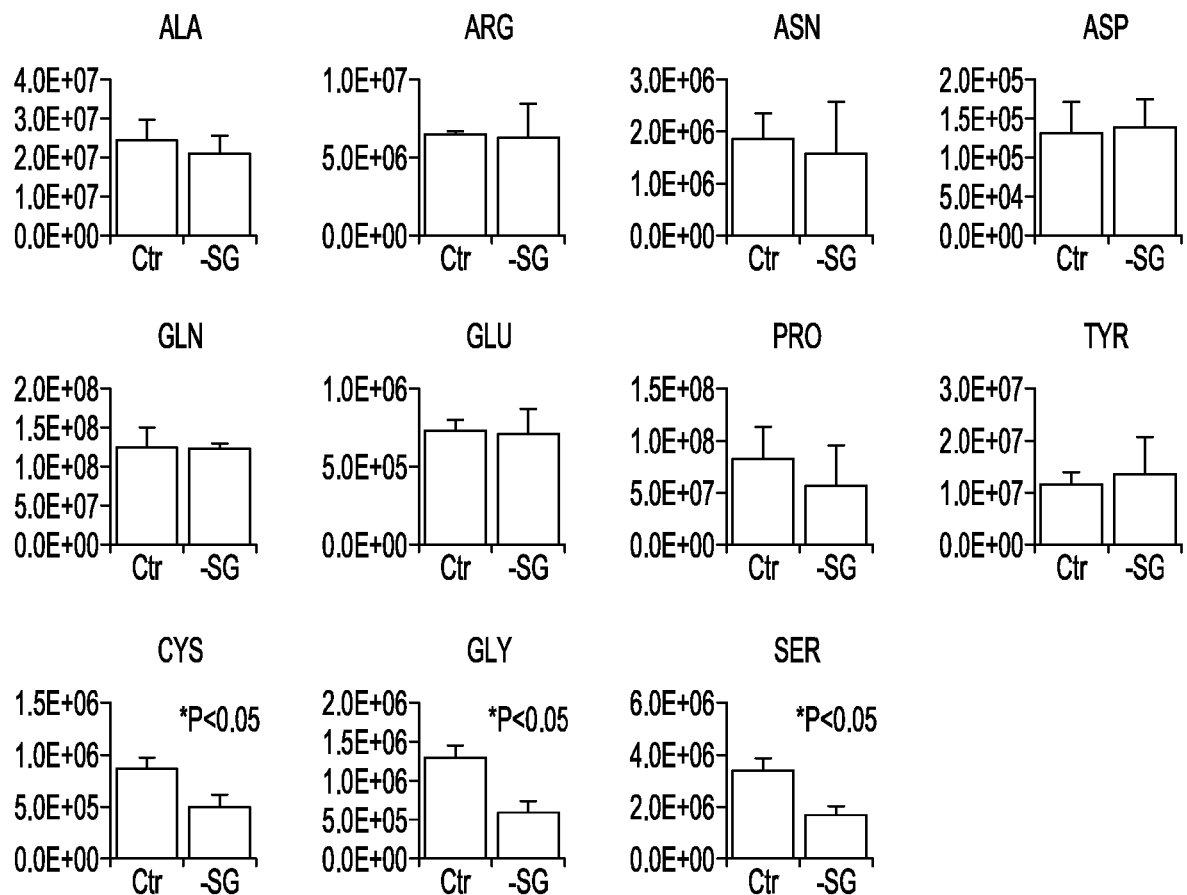
FIG. 6. Effect of dietary serine & glycine restriction on levels of amino acids in serum samples from mice. C57Bl6 mice were either fed a control diet containing all 20 amino acids, or a diet lacking serine and glycine but containing all 18 other amino acids. Serum samples were analysed by LCMS, relative quantities of all non-essential amino acids are shown. With the diet, reduced serine, glycine and cysteine levels are seen.

C57Bl6 mice (n=3 per diet group) were either fed a control diet (see "Diet 2-Control" above), or a diet lacking serine and glycine ("Diet 2—No Ser, No Gly" above) for six weeks. Terminal serum samples were analysed by LCMS as described above, relative quantities of all non-essential amino acids are shown. *P<0.05 unpaired t test. The results are shown in FIG. 6.

Cell Culture:

HCT116 and RKO cells were a gift of Prof. Bert Vogelstein. SW480, A549, MDA-MB-231, MDA-MB-468, and MCF7 cells were obtained from ATCC. Cell-culture products were obtained from Gibco unless otherwise stated;

catalog numbers are shown in parentheses. Cells were grown in a humidified atmosphere of 5% $CO_2$ in air at 37° C. Stock cells were maintained in McCoy's 5A medium (26600) supplemented with 10% fetal bovine serum (FBS; 10270) and penicillin-streptomycin, or in DMEM (21969) supplemented with 10% FBS (G10270), 2 mM L-glutamine, and penicillin-streptomycin. For starvation experiments, "assay medium" lacking serine and glycine was formulated with MEM (21090) supplemented with dialysed FBS (HyClone, Thermo Scientific), 2 mM L-glutamine, D-glucose (Sigma-Aldrich; final concentration 17 mM), MEM vitamins (11120), and penicillin-streptomycin.

Uptake/Release Assay:

The stated cells were seeded in 6-well plates (at appropriate seeding density to be ~90% confluent by the end of the assay) in complete medium and allowed to grow for 48 hr (medium was refreshed after 24 hr). At the start of the assay, cells were washed with PBS and received 1.5 ml per well of assay medium supplemented with both serine and glycine (0.4 mM). At the stated time points, 10 µl of medium was removed and added to 490 µl ice-cold methanol/acetonitrile/$H_2O$ (50:30:20). These samples were prepared for LC-MS as described below.

Liquid Chromatography-Mass Spectrometry:

Samples were shaken at 4° C. for 10 min, then centrifuged for 15 min at 16,000×g, and the supernatant was collected and analyzed by LC-MS. Analytes were separated using hydrophilic interaction liquid chromatography with a SeQuant ZIC-pHILIC column (2.1×150 mm, 5 µm) (Merck) and detected with high-resolution, accurate-mass mass spectrometry using an Orbitrap Exactive in line with an Accela autosampler and an Accela 600 pump (Thermo Scientific). The elution buffers were acetonitrile for buffer A and 20 mM $(NH_4)_2CO_3$ and 0.1% $NH_4OH$ in $H_2O$ for buffer B. A linear gradient was programmed starting from 80% buffer A and ending at 20% buffer A after 20 min, followed by wash (20% buffer A) and re-equilibration (80% buffer A) steps with a flow rate of 100 µl/min. The mass spectrometer was fitted with an electrospray-ionization probe and operated in full-scan and polar-switching mode with the positive voltage at 4.5 kV and negative voltage at 3.5 kV. Serine and glycine levels were quantified using five-point calibration curves spiked in cell lysates and media. Metabolite identification and data analysis were carried out using LCQUAN software (Thermo Scientific). The results are shown in FIG. 7.

Results

Figure 7:
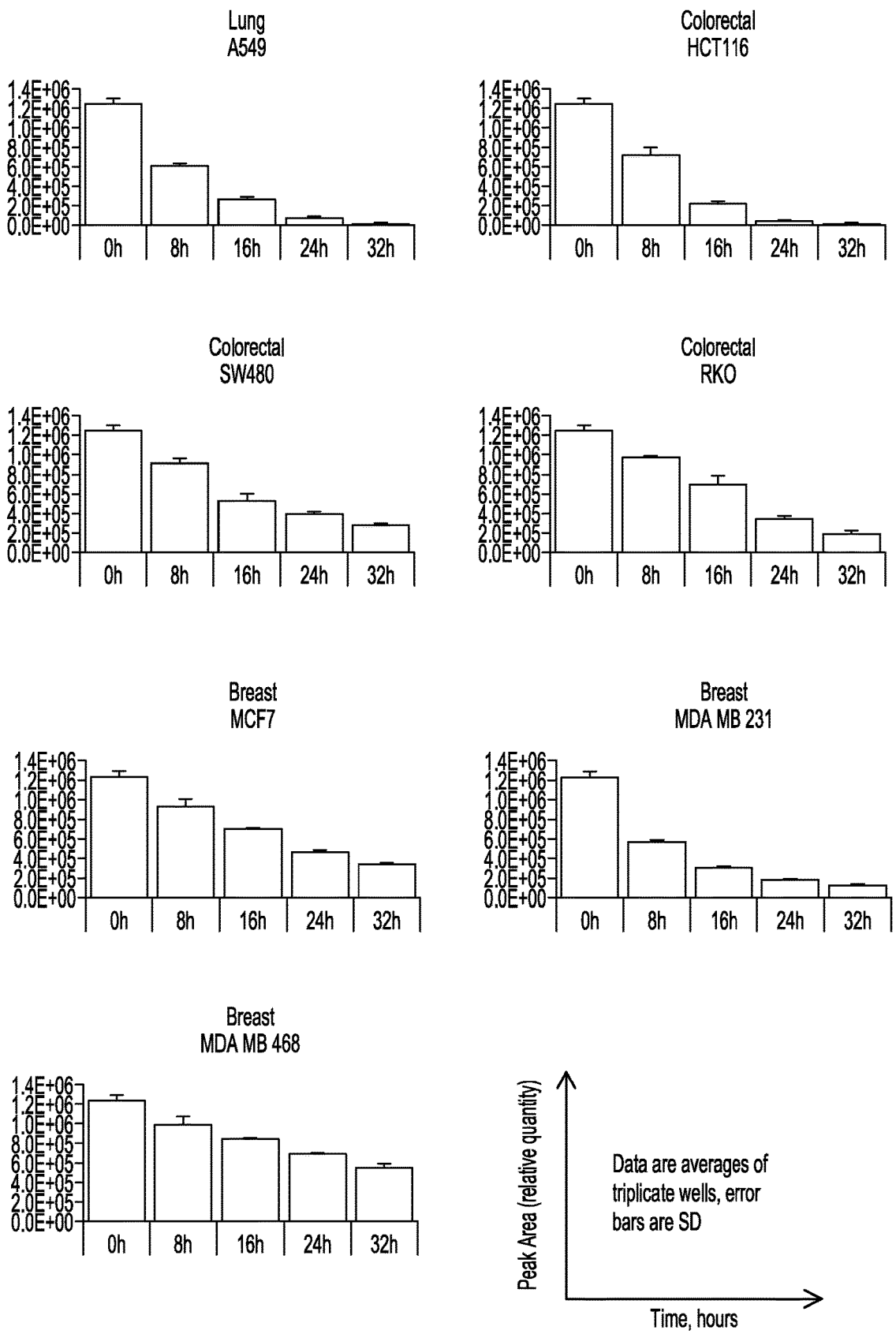
FIG. 7. Cysteine uptake from cell culture medium in multiple cell lines (A549, HCT116, SW480, RKO, MCF7, MDA MB 231 and MDA MB 468). Cancer cell lines are shown to avidly consume exogenous cysteine.

The data shown in FIG. 7 demonstrates that removing serine and glycine from the diet can also result in a depletion of cysteine/cystine levels in vivo, even when dietary cysteine/cystine is present. This effect is likely to occur because serine is used to synthesise cysteine de novo (See FIGS. 10 & 11). This data also suggests that dietary limitation of methionine (an essential amino acid that is also a precursor for cysteine in vivo) could further deplete systemic cysteine levels in vivo. The data shown in FIG. 7 show that cancer cell lines of multiple forms of cancer avidly consume exogenous cysteine/cystine, this suggests that cancer cells require exogenous cysteine to grow and may be defective for de novo cysteine synthesis (See FIGS. 10 & 11).

Example 4 (FIGS. 8, 9, 12 & 13)

Methods

Figure 8:
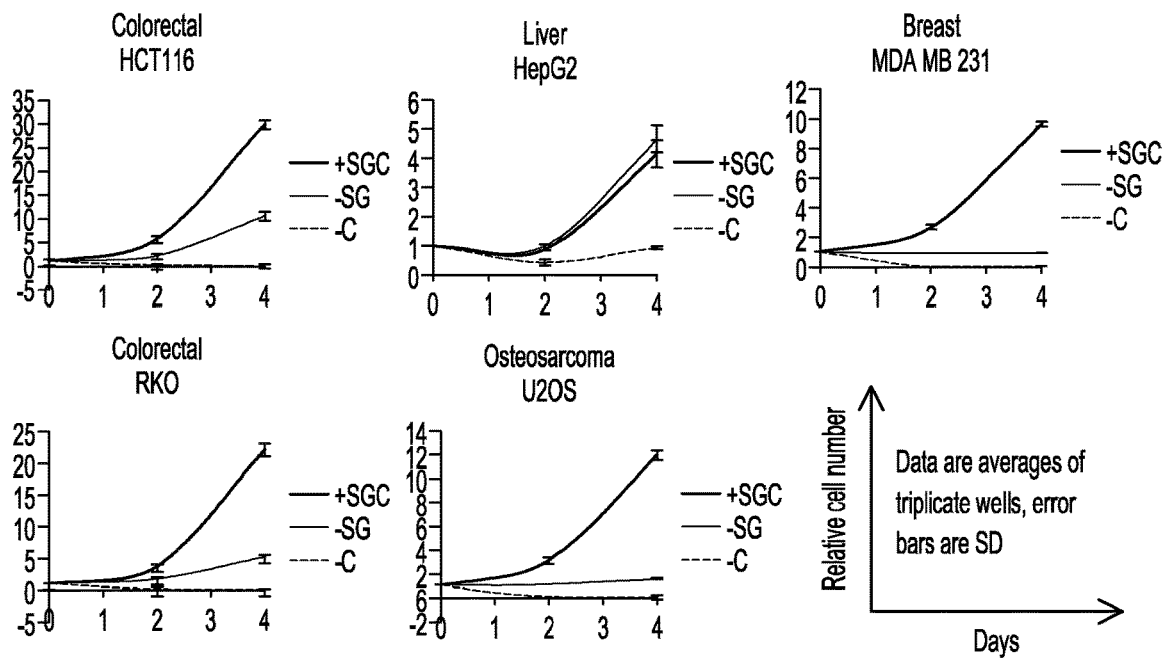
FIG. 8. Effects of cysteine starvation in multiple cell lines (HCT116, HepG2, MDA MB 231, RKO and U2O5). Base medium=all amino acids added except: serine, glycine, cysteine. S=Serine 0.8 mM G=Glycine 0.4 mM C=Cysteine 0.4 mM Medium replaced every 24 h.

The stated cells were seeded into 24-well plates at $2\times10^4$ to $1\times10^5$ cells per well and allowed to adhere overnight. Cells were then washed once with PBS and Experimental growth medium was added. Medium was either complete (+SGC) containing serine, glycine, cysteine and all other amino acids, or lacked only serine and glycine (–SG), or lacked only cysteine (–C). A separate "time-zero" counting plate was used to record starting cell number. Media were changed every 24 hours, and plates were counted after 2 and 4 days. Relative cell number was calculated by comparison to cell number at "time-zero." For counting, cells were trypsinized, re-suspended in PBS-EDTA, and counted with a CASY Model TT Cell Counter (Innovatis, Roche Applied Science). Data are averages of triplicate wells, error bars are standard deviation. The results are shown in FIG. 8.

Figure 9:
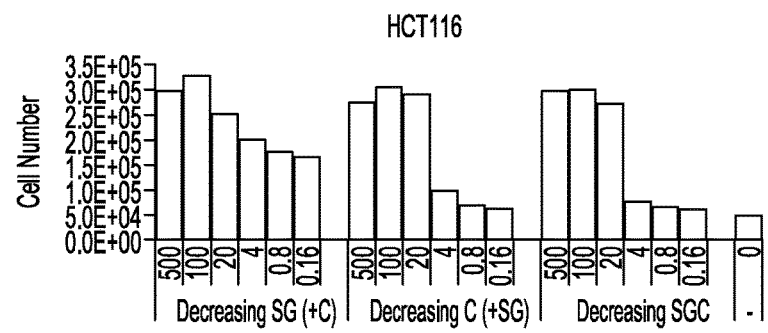
FIG. 9. Effects of the combined and separate starvation of cysteine and serine & glycine on cell numbers of three cell lines (HCT116, SW480 and DLD1). Cells were seeded in media with varying concentrations of serine, glycine and cysteine (but replete for all other amino acids) and counted after 48 h.
Figure 9:
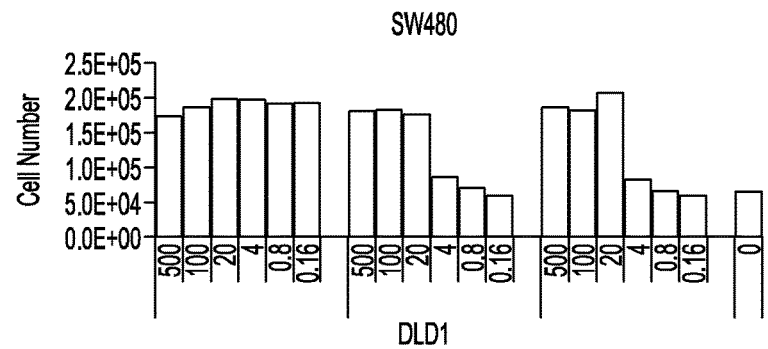
Figure 9:
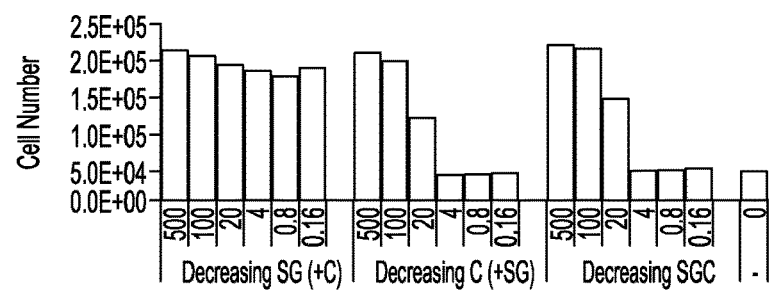
Figure 10:
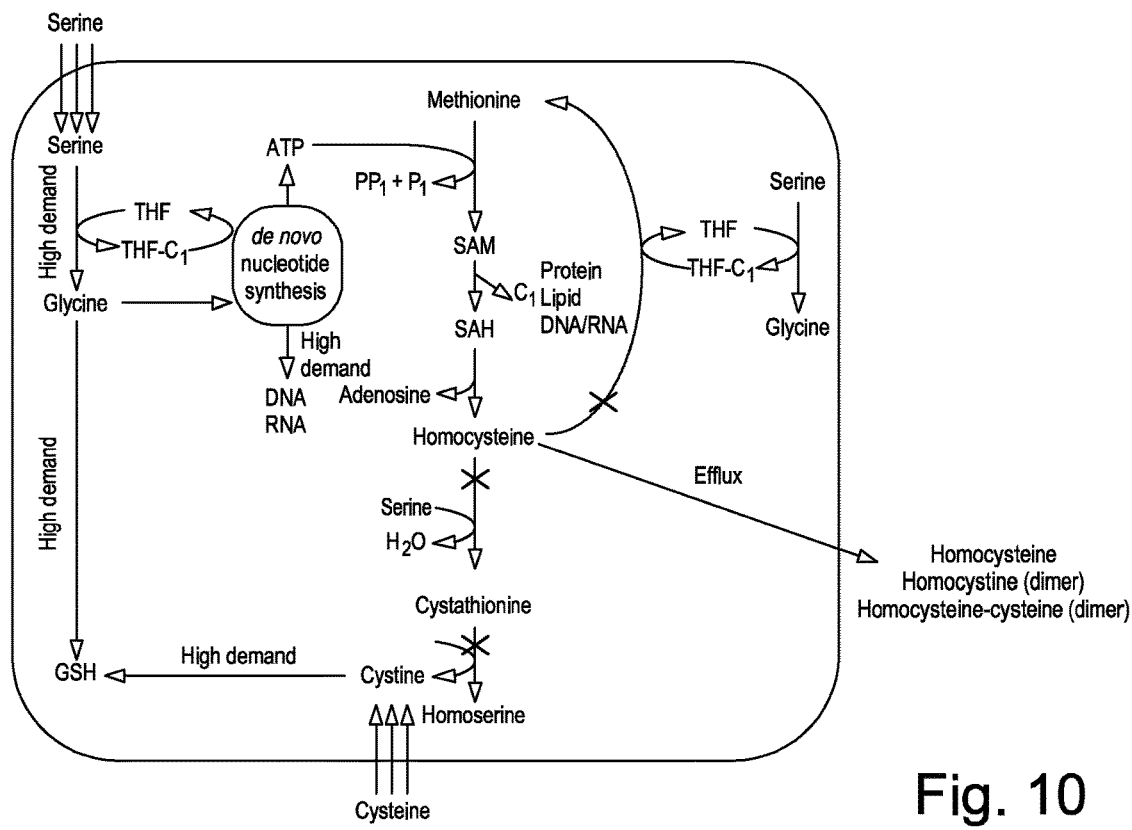
FIG. 10. Mechanism for serine and cysteine interdependence. Homocysteine efflux prevents depletion of serine pools in two ways; 1. Serine-derived one-carbons are not used for re-methylation, which allows the serine derived one-carbon pool to be used for nucleotide (DNA, RNA) synthesis instead 2. Serine is not needed to make cysteine. However, homocysteine efflux means cysteine can no longer be synthesized de novo, so must come from outside of the cancer cell. To meet the high anabolic demands for nucleotide and glutathione (GSH) synthesis, cancer cells require uptake of exogenous serine and cysteine.
Figure 11:
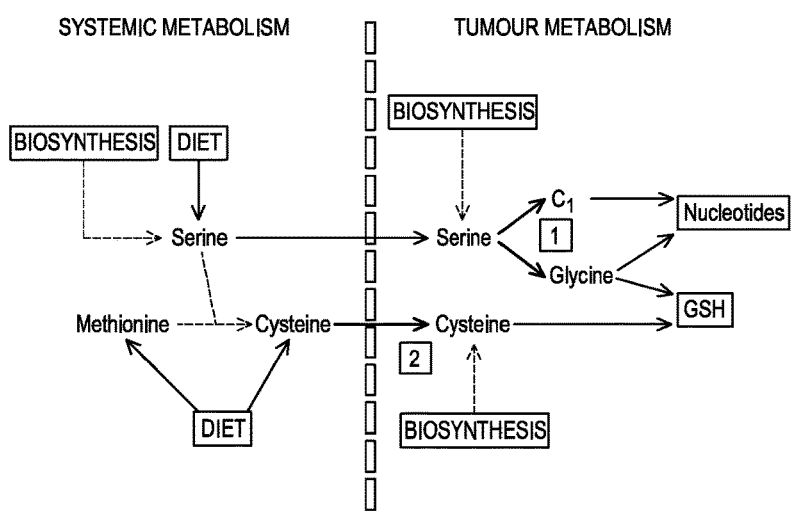
FIG. 11. Summary of systemic metabolism and tumour metabolism.

The stated cells were seeded into 24-well plates (at $2\times10^4$ to $1\times10^5$ cells per well) in media with the stated concentrations (ranging from 500 uM to 0.16 uM) of serine, glycine and cysteine (but replete for all other amino acids) and counted after 48 h. For counting, cells were trypsinized, re-suspended in PBS-EDTA, and counted with a CASY Model TT Cell Counter (Innovatis, Roche Applied Science). The results are shown in FIG. 9.

Figure 12:
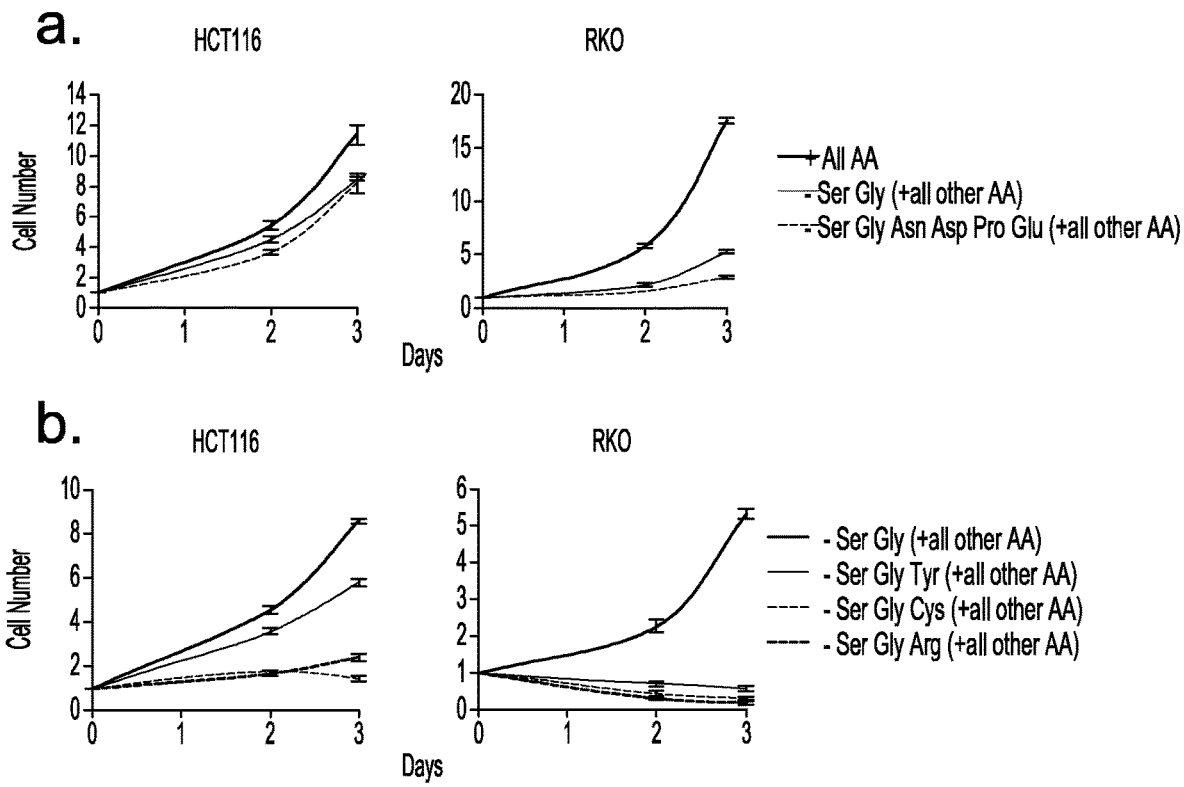
FIG. 12. Effect of withdrawal of non-essential amino acids, in addition to serine and glycine, on the growth of HCT116 and RKO cells. Showing an improvement to the anti-cancer effect of a serine and glycine free diet by modulating other amino acids. a. Serine and glycine starvation alone decreases proliferation rate. In addition to serine and glycine removal, withdrawing certain other non-essential amino acids (aspartic acid, glutamic acid, proline and asparagine) has a minor further additional effect on cell proliferation rate at 2 days. b. Serine and glycine starvation alone decreases proliferation rate. Furthermore, removal of tyrosine, arginine or cysteine individually has a greater anti-proliferative effect.

The stated cells were seeded into 24-well plates at $2\times10^4$ to $1\times10^5$ cells per well and allowed to adhere overnight. Cells were then washed once with PBS and Experimental growth medium was added. Medium was either complete with all amino acids (+All AA), or lacked only serine and glycine (-Ser Gly), or lacked serine, glycine, asparagine, aspartic acid, proline and glutamic acid (-Ser Gly Asn Asp Pro Glu), or lacked serine, glycine & tyrosine (-Ser Gly Tyr), or lacked serine, glycine & cysteine (-Ser Gly Cys), or lacked serine, glycine & arginine (-Ser Gly Arg). A separate "time-zero" counting plate was used to record starting cell number. Media were changed every 24 hours, and plates were counted after 2 and 3 days. Relative cell number was calculated by comparison to cell number at "time-zero." For counting, cells were trypsinized, re-suspended in PBS-EDTA, and counted with a CASY Model TT Cell Counter (Innovatis, Roche Applied Science). Data are averages of triplicate wells, error bars are standard deviation. The results are shown in FIG. 12.

Figure 13:
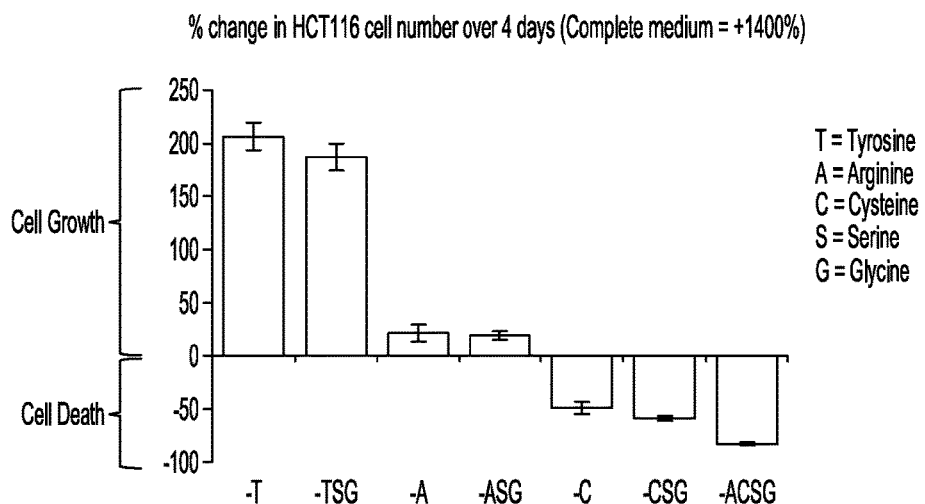
FIG. 13. Effect of the different combinations of serine, glycine, cysteine, arginine and tyrosine starvation on the cell growth and cell death (shown by a % change in cell numbers) of HCT116 cells over 4 days. The cell growth for complete medium (the control) was +1400%. Tyrosine starvation alone; tyrosine, serine and glycine starvation; arginine starvation alone; and arginine, serine and glycine starvation all resulted in growth inhibition. Cysteine starvation alone; cysteine, serine and glycine starvation; serine, glycine, cysteine, and arginine starvation resulted in growth inhibition and cell death.

HCT116 cells were seeded into 24-well plates at $4\times10^4$ cells per well and allowed to adhere overnight. Cells were then washed once with PBS and Experimental growth medium was added. Medium was either complete will all 20 amino acids or lacked the stated individual amino acids (Tyrosine/Arginine/Cysteine) or lacked combinations of the stated amino acids (Tyrosine/Arginine/Cysteine/Serine/Glycine). A separate "time-zero" counting plate was used to record starting cell number. Media were changed every 24 hours, and plates were counted after 4 days. Change in cell number was calculated by comparison to cell number at "time-zero" and calculated as a percentage (time-zero=100%). E.g. for cells in complete medium cell number after four days was 1400% vs. time-zero. Cell with negative % change from time-zero were subject to cell death and appear below the x-axis. For counting, cells were trypsinized, re-suspended in PBS-EDTA, and counted with a CASY Model TT Cell Counter (Innovatis, Roche Applied Science). Data are averages of triplicate wells, error bars are standard deviation. The results are shown in FIG. 13.

Results

The data in FIGS. 8 & 9 show that removal of exogenous cysteine inhibits the growth of cancer cells from multiple types of cancer and that cysteine depletion in vitro is highly effective at inhibiting cancer cell proliferation, achieving a greater inhibition of proliferation than serine and glycine starvation alone. FIG. 12 shows that the specific combination of exogenous non-essential amino acids that are removed (i.e. that cells are starved of) determines the degree to which proliferation is inhibited in cancer cells. The anti-proliferative effect of removing serine and glycine alone is minimally enhanced by removing aspartate, asparagine, proline and glutamate. Whereas, the additional removal of tyrosine, arginine or cysteine individually in combination with serine and glycine has a more dramatic impact on proliferation. FIG. 13 further shows that when cysteine or specific combinations of non-essential amino acids are removed from cancer cells a cytotoxic effect (i.e. beyond mere anti-proliferative activity) can be achieved, and this is greatest when multiple non-essential amino acids are removed.

Figure 14:
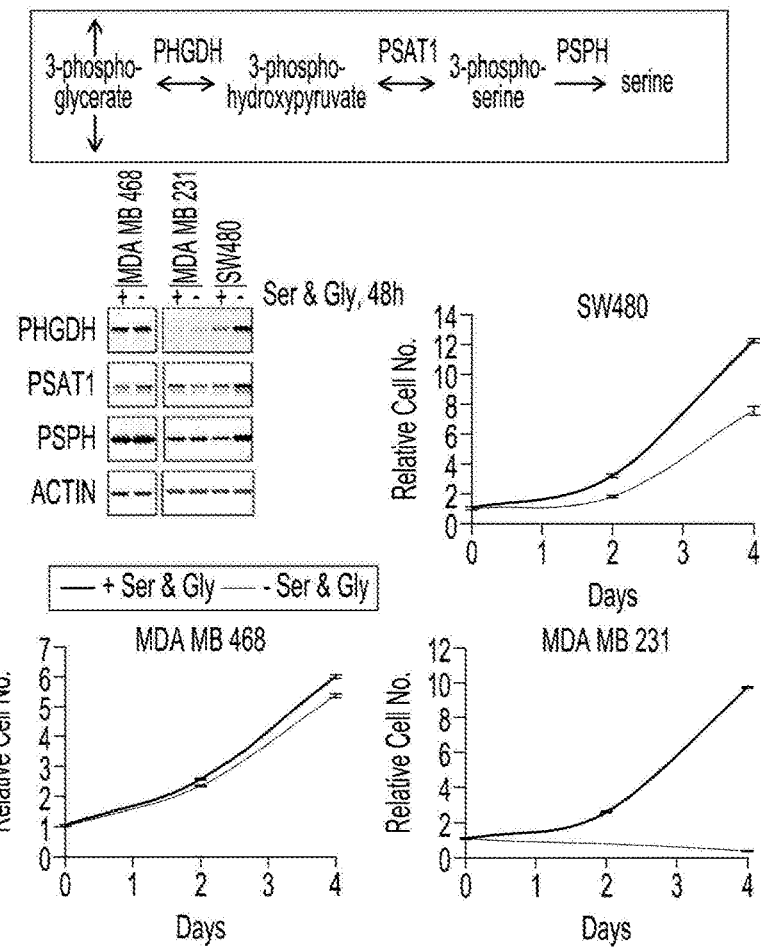
FIG. 14. Serine synthesis pathway enzyme expression is a determinant of sensitivity to serine starvation. Tumours with elevated expression or enhanced activity of serine synthesis pathway enzymes (PHGDH, PSAT1, PSPH) are less sensitive to serine starvation. Serine synthesis pathway activity may be increased by multiple mechanisms in cancer, including gene copy number amplification, transcriptional activation (e.g. by oncogenic Kras), or by epigenetic means, or potentially by other mechanisms, e.g. allosteric activation.

Example 5 (FIG. 14)

Methods

Expression of serine synthesis pathway enzymes (PHGDH, PSAT1 and PSPH) were determined by western blot (as described above) in the stated cancer cell lines (top left panel) grown with or without serine and glycine for 48 h. The stated cells were seeded into 24-well plates at 2×10^4 to 1×10^5 cells per well and allowed to adhere overnight. Cells were then washed once with PBS and growth medium either containing or lacking serine and glycine was added (both media contained all essential amino acids and cysteine, arginine, glutamine and tyrosine). A separate "time-zero" counting plate was used to record starting cell number. Media were changed every 24 hours, and plates were counted after 2 and 4 days. Relative cell number was calculated by comparison to cell number at "time-zero." For counting, cells were trypsinized, re-suspended in PBS-EDTA, and counted with a CASY Model TT Cell Counter (Innovatis, Roche Applied Science). Data are averages of triplicate wells, error bars are standard error of mean. The results are shown in FIG. 14.

Results

The data in FIG. 14 shows that cancer cells have varying levels of expression of enzymes that undertake de novo serine synthesis, and that expression of these proteins impacts the sensitivity of cells to serine and glycine starvation. Hence cells expressing high levels of serine synthesis enzymes are resistant to the anti-proliferative effect of serine and glycine starvation, but those with low expression are sensitive.

Figure 15:
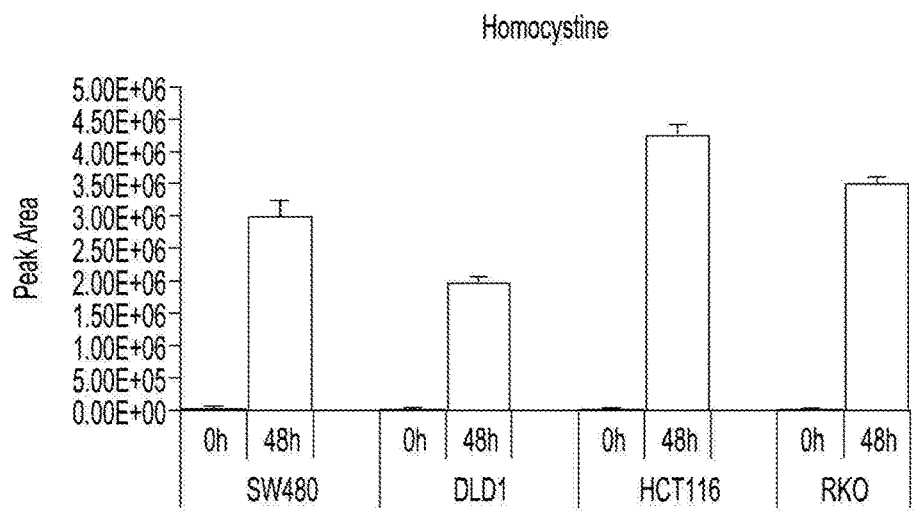
FIG. 15. Measurement of the release of cysteine precursors/homocysteine dimers in 4 cell lines (SW480, DLD1, HCT116 and RKO) cultured in complete media over 48 hours. Homocysteine is a precursor for de novo synthesis of cysteine, however, homocysteine is released from cancer cells and detected a homodimer, i.e. homocystine.
Figure 16:
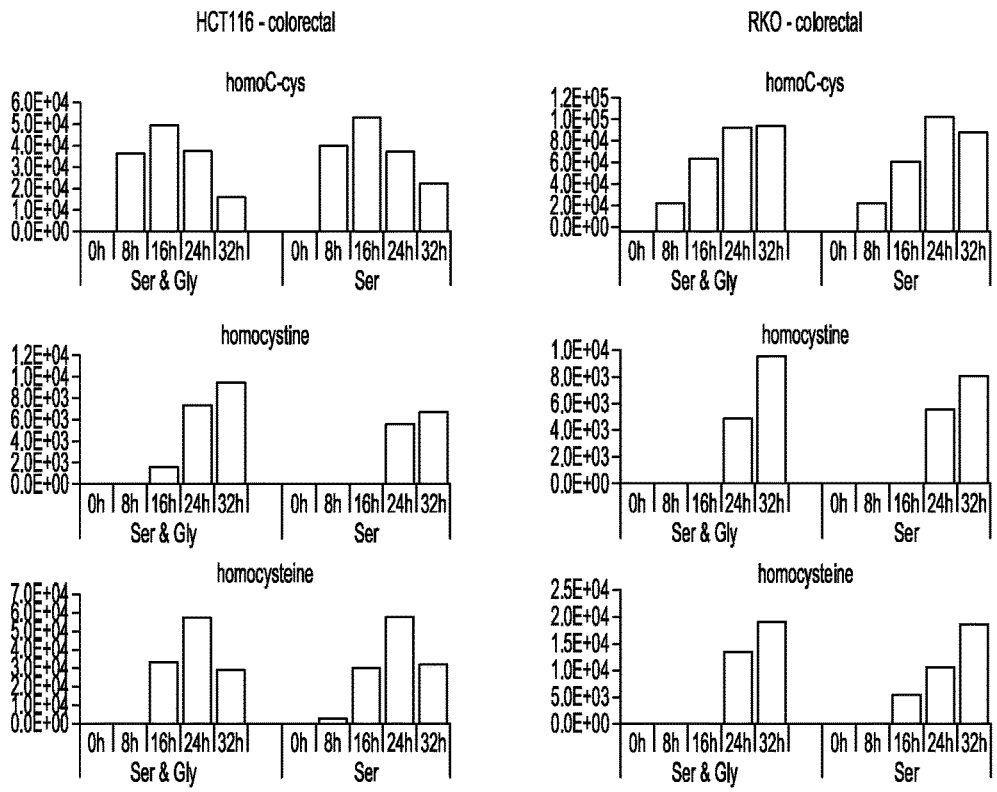
FIG. 16. Measurement of the release of cysteine precursors/homocysteine dimers in 2 cell lines (HCT116 and RKO), under serine and serine & glycine starvation conditions. homoC-cys=homocysteine+cysteine dimer. Homocystine=homocysteine+homocysteine dimer.
Figure 17:
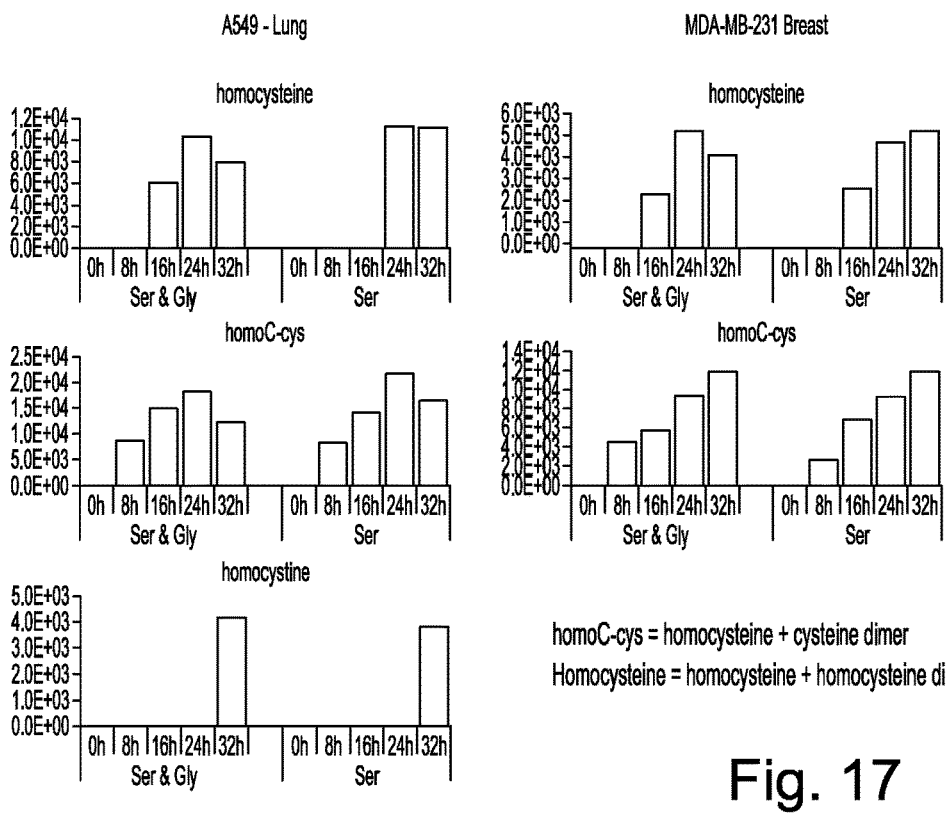
FIG. 17. Measurement of the release of cysteine precursors/homocysteine dimers in 2 cell lines (A549 and MDA MB 231), under serine and serine & glycine starvation conditions. homoC-cys=homocysteine+cysteine dimer. Homocystine=homocysteine+homocysteine dimer FIG. 18. Serine and glycine free diet is an effective therapeutic intervention in GEMMs for lymphoma and intestinal cancer. a. Eμ-Myc mice received normal chow until ~60 days of age, then were transferred to either a control diet (containing serine and glycine) or a matched diet lacking serine and glycine (No Ser, No Gly) until clinical end-point (lymphoma-related survival). Survival was calculated from change of diet (not birth). P value calculated by Mantel-Cox test. b. APCMin/+ mice received normal chow until ~80 days of age, then were transferred to either a control diet (containing serine and glycine) or a matched diet lacking serine and glycine (No Ser, No Gly) until clinical end-point (intestinal tumour related survival). Survival was calculated from change of diet (not birth). P value calculated by Mantel-Cox test. c. Serum from Eμ-Myc and d. APCMin/+ cohorts was analysed by LCMS, relative abundance (by metabolite peak area) is shown. Error bars=STDEV, P values were calculated by T-test (unpaired, 2 tails, *=P<0.0005). See FIG. 21 for relative quantification of all amino acids. e. Serum concentration for serine and glycine in the APCMin/+ cohort was determined using 6-point calibration curves with 13C15N-serine & glycine diluted in serum. Error bars=STDEV. f. Lgr5-creER APCfl/fl mice were induced at 7-10 weeks of age, diet was changed seven days after first tamoxifen treatment and maintained until clinical end-point (intestinal tumour-related survival). Survival is calculated from first tamoxifen treatment. P value calculated by Mantel-Cox test.
Figure 18:
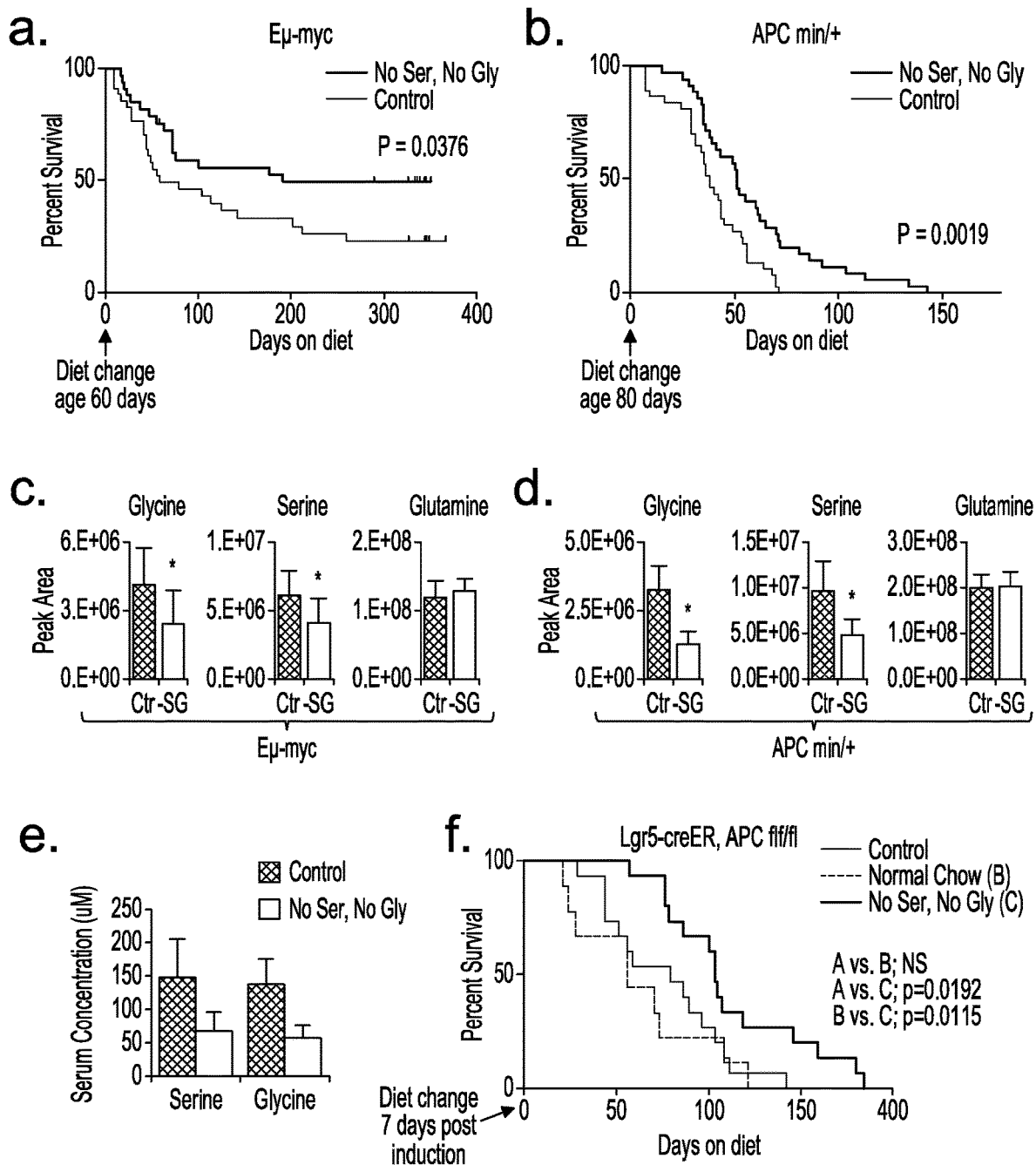
Figure 19:
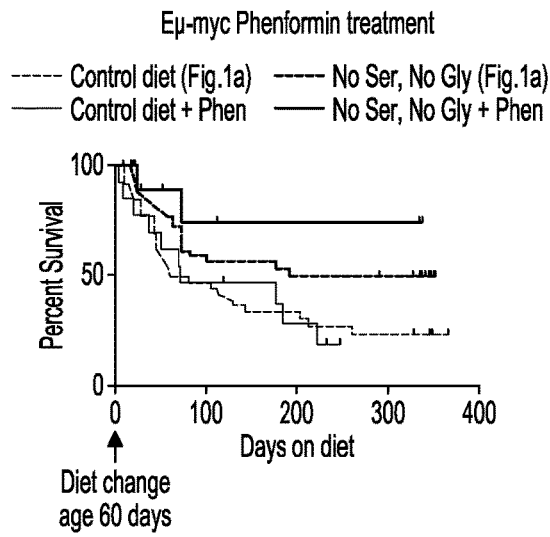
FIG. 19. Manipulation of anti-oxidant response enhanced diet-induced anti-cancer effect. a. Eμ-Myc mice received control or serine and glycine free diet (No Ser, No Gly) with 100 mg/kg/day Phenformin (Phen.) by gavage at ~60 days of age and taken to clinical end-point. Lymphoma-related survival was calculated from change of diet, not birth. b. APCMin/+ mice were transferred to Control or serine and glycine free diet (No Ser, No Gly) at ~80 days of age, then four days later received Metformin (Metf.) 200 mg/kg/day in drinking water. Intestinal tumour-related survival calculated from change of diet, not birth. P value calculated by Mantel-Cox test. See FIG. 22a for complete comparison of survival curves. c. Comparison of diet-only tumour burden data with metformin+diet tumour burden. Post-mortem count of tumour number was performed on the small intestines (SI) of APC$^{Min/+}$ mice. P values calculated by T-test (unpaired, 2 tails). See FIG. 22c for tumour area data. Diet-only data replicated in (a) and (b) above. d. Intestinal tumour organoids derived from a Villin$^{creER}$; APC$^{fl/fl}$ mouse were grown +/−SG, +/−metformin at the stated concentrations for two days. Relative change (versus '-drug') in organoid diameter is plotted. Data are average of four independent experiments, error bars=SEM. P values calculated by T-test (unpaired, two tails, with correction for multiple comparisons). e. APC$^{fl/fl}$ organoids were grown +/−SG +/−metformin for two days, then fixed and immuno-stained for lipid peroxidation product malondialdehyde (MDA). Data is average of three independent experiments, error bars=SEM. P values calculated by T-test (unpaired, two tails, corrected for multiple comparisons). f. Eμ-Myc mice were crossed with Tigar-/- mice, cohorts were placed on diets at ~60 days of age and taken until clinical end-point (lymphoma-related survival). Survival was calculated from change of diet (not birth). P value calculated by Mantel-Cox test.
Figure 19:
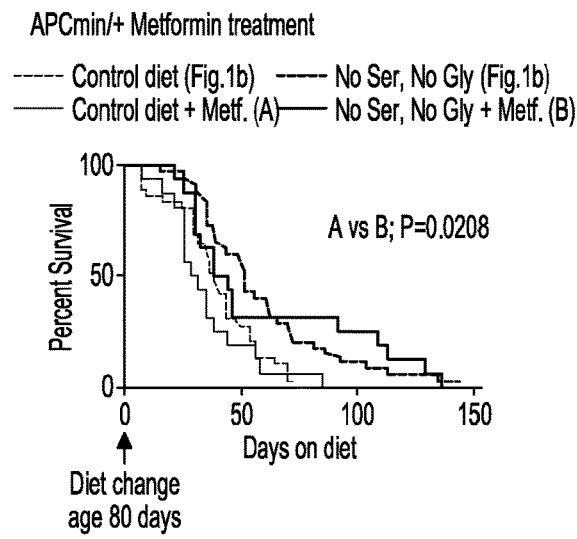
Figure 19:
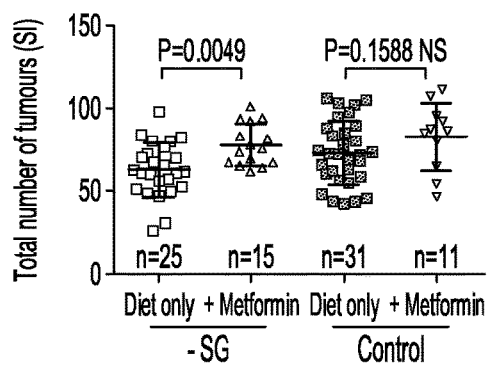
Figure 19:
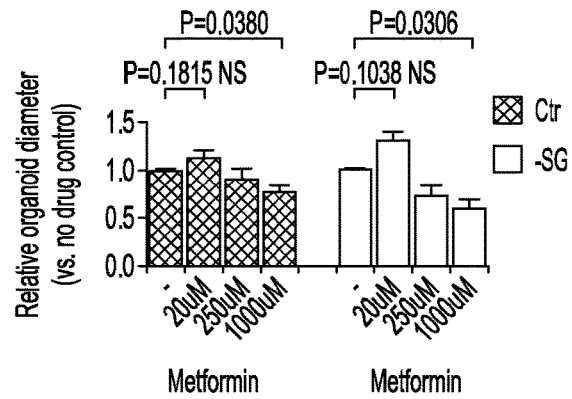
Figure 19:
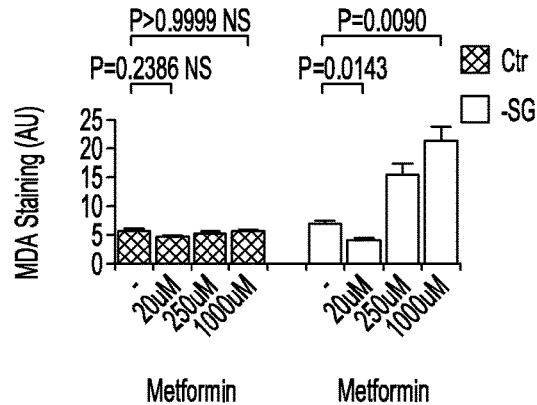
Figure 19:
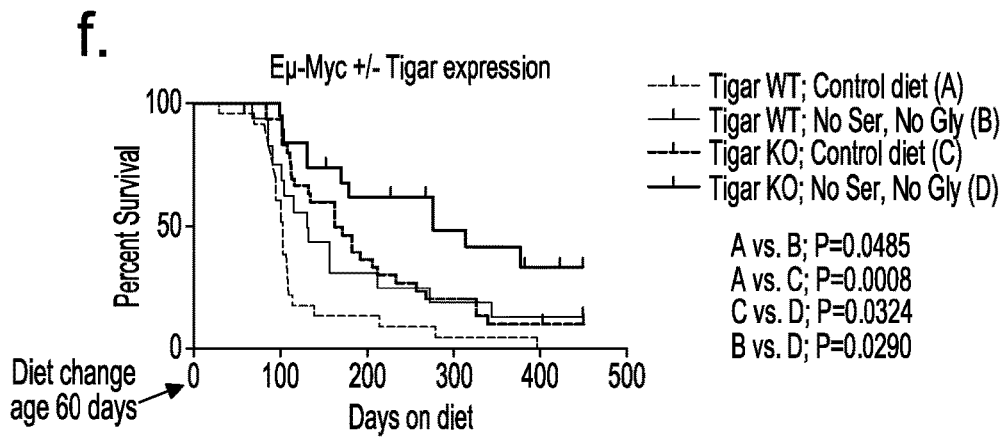

Example 6 (FIGS. 15, 16 & 17)

Methods

The stated cells were seeded in 6-well plates (at appropriate seeding density to be ~90% confluent by the end of the assay) in complete medium and allowed to grow for 48 hr (medium was refreshed after 24 hr). At the start of the assay, cells were washed with PBS and received 1.5 ml per well of assay medium (containing all essential amino acids, glutamine, arginine, tyrosine and cysteine) supplemented with both serine and glycine (0.4 mM) or serine only (0.4 mM). At the stated time points, 10 µl of medium was removed and added to 490 µl ice-cold methanol/acetonitrile/$H_2O$ (50:30:20). These samples were prepared for and analysed by LC-MS as described above. The results are shown in FIGS. 16 and 17.

Results

The data in FIGS. 15, 16 & 17 show that cancer cells show net efflux (i.e. release) precursors for the de novo synthesis of cysteine. Homocysteine is derived from methionine and is essential for the de novo synthesis of cysteine in mammalian cells (see also FIGS. 10 & 11). Homocysteine is lost from these cancer cells—potentially contributing to their inability to make cysteine and therefore sensitivity to cysteine starvation—in various forms, and can be detected by mass spectrometry as a the unchanged molecule (homocysteine) or as a homodimer (homocystine) and heterodimer (with cysteine).

Example 7 (FIGS. 24, 25, 26, 27, 28, 29, 30, 31)

Cell lines & Cell Culture

HCT116 cells were obtained from ATCC and authenticated using Promega GenePrint 10. iKRAS cells (iKRAS1, iKRAS3, AK196) were kindly supplied by Prof. Ronald DePinho (Ying et al., Cell, 2012), (The University of Texas MD Anderson Cancer Center). Cell culture media were purchased from GIBCO, product numbers are shown in parenthesis. iKRAS (DMEM—21969) and HCT116 cells (RPMI-1640-31870) were maintained in the stated media supplemented with 10% FBS (10270), penicillin-streptomycin & amphotericin with L-glutamine at final concentration of 2 mM. Stock iKRAS cells were grown in the presence of doxycycline 2 µg/ml (KRAS-ON) and in medium with/without doxycycline (KRAS-ON/OFF) for experiments. Cells were maintained in 37° C., 5% $CO_2$ humidified incubators. Cultured cells were routinely tested for mycoplasma using Mycoalert detection kit (Lonza).

Proliferation Assays

HCT116 cells (2.5×10^4 per well) were seeded in complete RPMI medium in 24-well plates and allowed to adhere overnight. Cells were then washed with PBS and received modified MEM medium supplemented with various concentrations of serine and glycine[2]. Medium was replaced with fresh medium every 24 hours. Wells were counted (using Casy TT cell counter, Innovatis, Roche Applied Science) at the stated time-points, using a "time=0" plate to calculate relative cell number from time of medium change.

Tumour Organoid Culture

ADF=Advanced DMEM/F-12, with 2 mM glutamine, 1% penicillin/streptomycin solution, 0.1% AlbuMAX I BSA, 10 mM HEPES (all Gibco/Life Technologies). Adenomatous small intestine tissue was excised and cut into smaller pieces and washed 5 times with ice cold PBS. Pieces were incubated in 5 mM EDTA for 10 min at 4° C. on a roller. Crypts were washed 2 times with ice cold PBS to remove EDTA and incubated in 10× trypsin for 30 min at 37° C. The crypt-enriched supernatant was collected and washed approximately 5 times with 5 ml ADF through mechanical pipetting. Crypts were pelleted via centrifugation at 1,200 rpm for 5 min. Crypts were re-suspended in growth factor reduced matrigel (BD Biosciences) and 20 µl was plated per well in a 12-well plate. Matrigel was allowed to solidify for 30 min in a 37° C. incubator before appropriate ADF was added supplemented with 0.05 µg/ml EGF and 0.1 µg/ml noggin (Total volume per well 1 ml). Crypts were split by harvesting in ice cold PBS and spun down at 600 rpm for 3 min. Supernatant was aspirated and the pellet dissociated with 100 µl ice cold PBS using mechanical pipetting. 5 ml of PBS was added to tube and spun down at 600 rpm for 3 min, repeated until supernatant was clear of debris. The final crypt pellet was re-suspended with growth factor reduced matrigel and plated as before. For SG starvation, amino acid free Advanced DMEM/F-12 (Gibco/Life Technologies) was used to construct assay medium for organoids with or without serine and glycine (0.2 mM), containing all other amino acids. For LCMS analysis organoids were grown in 12-well plates in complete medium for three days. Medium was aspirated and organoids were washed with PBS. The medium was replaced with glucose-free Advanced DMEM/F-12 (Gibco/Life Technologies) supplemented with 15 mM $^{13}C_6$-glucose (CK-Gas/Cambridge Isotopes). After five hours media was aspirated, organoids were briefly washed in PBS and metabolites were extracted as described below.

Organoid Imaging

Organoids were seeded in the stated media with or without metformin/daunorubicin (both from Sigma) and allowed to grow for two days. Images for size quantification (performed using ImageJ software) were taken using a light microscope then organoids were fixed in 4% paraformaldehyde. ROS damage was assessed by immunostaining organoids with Anti-malondialdehyde (MDA) (Abcam, ab6463), with Alexa Fluor 594 secondary antibody (Thermo Fisher Scientific). Images were captured on an Olympus FV1000 inverted laser scanning confocal microscope and MDA staining was quantified using ImageJ software.

Liquid Chromatography Mass Spectrometry (LCMS)

Samples were prepared in cold (−20° C.) lysis solvent (LS) consisting of methanol, acetonitrile, and $H_2O$ (50:30:20). Serum (isolated from terminal bleeds & stored at −80° C.) samples of 10 μl were added to 490 μl of LS and vortexed, precipitated protein was cleared by centrifugation (15000 rpm for 10 mins at 4° C.). Organoid extracts were prepared by briefly washing wells with excess PBS then adding 250 μl LS per well and placing on a rocking shaker at 4° C. for 10 minutes, LS was removed from wells (without mechanical disruption of organoids/matrigel) and then vortexed and cleared by centrifugation. Tissue samples were snap frozen and stored at −80° C. Prior to lysis, frozen samples were weighed. Tissues were then homogenized in 1 ml cold LS using a Precellys homogeniser (Bertin Technologies) or a TissueLyser II (Qiagen). Lysates were cleared of protein by centrifugation and lysate concentrations normalized post-homogenisation with LS to 10 mg/ml based on original tissue weight.

Extracts were analysed on an LCMS platform consisting of an Accela 600 LC system and an Exactive mass spectrometer (Thermo Scientific). Two LC methods were applied for metabolite separation prior to MS detection. Method 1 employed a SeQuant ZIC-pHILIC column (2.1 mm×150 mm, 5 μm) (Merck) with the mobile phase mixed by A=Ammonium carbonate 20 mM (adjusted to pH 9.4) and B=Acetonitrile. A gradient program starting at 20% of A and after 2 mins linearly increasing to 80% at 17 min was used followed by washing and re-equilibration steps. The total run time of the method 1 was 25 min. Method 2 employed a ZIC-HILIC column (4.6 mm×150 mm, 3.5 μm) (Merck) with the mobile phase mixed by A=water with 0.1% formic acid (v/v) and B=acetonitrile with 0.1% formic acid. A gradient program starting at 20% of A and linearly increasing to 80% at 30 min was used followed by washing and re-equilibration steps. The total run time of the method 2 was 46 min. The LC stream was desolvated and ionised in the HESI probe. The Exactive mass spectrometer was operated in full scan mode over a mass range of 75-1,000 m/z at a resolution of 50,000 with polarity switching. LCMS quantification of serine and glycine was achieved with 6-point standard curves using $^{13}C$-$^{15}N$-labelled amino acids (Sigma) diluted in a relevant matrix matched to the analytical sample. The raw data was analysed by LCquan (Thermo Scientific) and MZMine 2.10 for metabolite identification and quantification.

Unbiased Metabolomics

Raw LCMS data was converted into mzML files using ProteoWizard and imported into MZMine 2.10 for peak extraction and sample alignment. The generated .CSV file was imported into an in-house macro (Microsoft Excel 2010) for metabolite identification and removal of background signals. The detailed procedure and setting parameters are previously described (Zhang et al., PLoS One, 2013). SIMCA 14 (Umetrics) was used for multivariate analysis. The S-plots were produced in OPLS-DA (orthogonal partial least squares discriminant analysis) models for targeting the most influential metabolites.

Diets

From weaning, mice received 'normal chow' (Rat and Mouse Breeder and Grower, 801730, Special Diet Services, SDS, UK) and water ad libitum. On normal chow, dietary amino acids are derived from whole proteins contained in the raw ingredients (wheat, wheatfeed, barley, de-hulled extracted toasted soya, maize and fish meal), with a small amount of purified lysine added as a supplement. Two sets of experimental diets were used, both based on Baker Purified Amino Acid Diet (Hirakawa et al., Nutr. Res. 1984) from TestDiet (Richmond, IN): "Diet 1-Control" contained all essential amino acids plus serine, glycine, glutamine, arginine, cystine, and tyrosine; "Diet 1-SG-free" was the same as Diet 1-Control, but without serine and glycine, with the other amino acid levels increased proportionally to achieve the same total amino acid content. These "Diet 1" formulations were used previously (Maddocks et al., Nature, 2013). "Diet 2-Control" contained all essential amino acids plus serine, glycine, glutamine, arginine, cystine, tyrosine, alanine, proline, glutamate and asparagine; "Diet 2-SG-free" was the same as Diet 2-Control, but without serine and glycine, with the other amino acid levels increased proportionally to achieve the same total amino acid content. "Diet 2" formulations were used for the Eμ-Myc; Tigar$^{-/-}$ cohort (FIG. 2f). All other cohorts received the previously published "Diet 1" formulations.

Mice—GEM Models

All animal work was carried out in line with the Animals (Scientific Procedures) Act 1986 and the EU Directive 2010 (PPLs 60/4181, PPL70/8645 & 70/8646) and was sanctioned by the local ethical review process (University of Glasgow). Mus Musculus cohorts were housed in a barrier facility proactive in environmental enrichment. The Eμ-Myc (Adams et al., Nature 1985), Apc$^{Min/+}$ (Moser et al., Science, 1990; Su et al., Science, 1992) Lgr5$^{creER}$; Apc$^{fl/fl}$ (Barker et al., Nature, 1990) and Pdx1cre; Kras$^{G12D/+}$; Trp53$^{fl/+}$ or Pdx1$^{cre}$; Kras$^{G12D/+}$; Trp53$^{R172H/+}$ (Hingorani et al., Cancer Cell, 2005; Morten et al., Proc. Natl. Acad. Sci. USA, 2010) mice/models have been previously described. Mixed male and female populations were used for each genotype. The number of mice (or number of samples from individual mice) is shown in each Figure/Figure Legend. Eμ-Myc, and Apc$^{Min/+}$ mice were at least 20 generations C57BL/6J (Bl6). Eμ-Myc; Tigar$^{-/-}$ mice were a mixed strain but at least 50% C57BL/6J. Pancreatic (PDAC) cohorts were on a mixed strain background but all cohorts compromised of litter-matched controls. Mice were put on the appropriate diet at the following times: Eμ-Myc (Bl6) 60 days post-natal, Eμ-Myc; Tigar$^{-/-}$ 55 days post-natal, Apc$^{Min/+}$80 days post-natal, Lgr5$^{creER}$; Apc$^{fl/fl}$ 7 days post-induction, Pdx1$^{cre}$; Kras$^{G12D}$; Trp53$^{fl/fl}$ or Pdx1$^{cre}$; Kras$^{G12D}$; Trp53$^{R172H/+}$ 60 days post-natal. Recombination by Lgr5$^{creER}$ was induced with two intraperitoneal injections of 120 mg/kg tamoxifen, with a day's rest between the injections. For the phenformin experiment, Eμ-Myc mice were gavaged daily with 100 mg/kg mouse body weight, starting the same day as the diet change. For the metformin experiment, Apc$^{Min/+}$ mice were given 200 mg/kg/day in their drinking water, starting four days after the diet change. Villin$^{creER}$; APC$^{fl/+}$; Kras$^{G12D/+}$ mice [C57Bl/6J N10] were placed on experimental diet at 6-8 weeks of age, kept on diet for two weeks, and then induced with a single IP injection of tamoxifen (80 mg/kg). Intestines were fixed in methacarn (4:2:1 ratio of methanol, chloroform, acetic acid) to facilitate scoring of tumour number and area (width×length). Apart from n=6 APC$^{min/+}$ mice, used for BrdU & Caspase staining, all other GEM mice were taken to humane clinical end-point.

Sample sizes for mouse studies were estimated from previous experience with these models where potential differences in survival are tested by Mantel-Cox (Log Rank) analysis. After data was collected for the first experimental groups (e.g. Eµ-Myc and APC$^{Min/+}$ on diet only, FIGS. 18*a* & 18*b*) subsequent groups were reduced in size to minimize animal numbers used (e.g. Phenformin and Metformin treatment groups, FIGS. 19*a* & 19*b*). In all experiments mice with overt phenotype at time of enrolment into the study were excluded (i.e. not enrolled): e.g. enlarged lymph nodes or signs of enlarged thymus in the Eµ-Myc cohorts, anemia in the APC$^{Min/+}$ cohorts. Animals that died due to illness unrelated to tumour(s) were included as censored observations. Mice were allocated into the experimental groups according to a randomized block design: as mice became available through breeding, they were split into blocks based on gender and then randomly assigned to a treatment arm. Care was taken to keep the male/female ratio similar in order to remove gender as a potential source of variability. The investigator allocating mice to the experimental groups and collecting the endpoint data was not blinded.

Mice—Xenografts/Allografts

HCT116 cells were implanted by bilateral sub-cutaneous injections (3×10^6 cells per flank) into CD1-Foxn1$^{nu}$ (CD1-Nude) female mice (Charles River, UK). Mice were maintained on normal chow diet and monitored daily until visible, measurable tumours had formed. Tumour bearing mice were placed onto control (n=8 mice) or SG-free diet (n=8 mice), tumours were measured with calipers three times per week, any opposing flank tumours which developed subsequent to diet change were excluded from the analysis. Average tumour volumes are plotted for the first five weeks on diet. Tumour volumes were calculated using the formula; volume=(length×width$^2$)/2.

Eµ-Myc lymphoma cells were isolated from tumour bearing lymph nodes of mixed background Eµ-Myc mice by FACS. These cells were initially expanded in cell culture with irradiated mouse embryonic fibroblasts (MEFs) and passaged until they could grow independently. Culture medium was DMEM/F-12 (Gibco/Life Technologies) supplemented with 10% FBS, 50 µM beta-mercaptoethanol, penicillin, streptomycin, gentamycin and amphotericin. Cells were implanted by bilateral sub-cutaneous injections (5×10^5 cells per flank) into CD1-Foxn1$^{nu}$ female mice (Charles River, UK). Mice were maintained on normal chow diet and monitored daily until visible, measurable tumours had formed. Tumour bearing mice were placed onto control or SG-free diets, tumours were measured with calipers every 2/3 days. Once the first mouse in the cohort reached clinical end-point (maximum permitted tumour volume) all mice in the cohort were killed and tumours removed (this occurred after 6 days on diet). Tumours were fixed in formalin, paraffin embedded and sections cut for histology.

BrdU and Caspase Staining and Necrosis Quantification

Two hours before sacrifice, mice were injected with 250 ul of cell proliferation labeling reagent containing BrdU (RPN201, Amersham/GE Heathcare). Antibodies used: Cleaved caspase 3 ASP-175 (Cell Signaling Technology, 9661), anti-BrdU (BD Biosciences, 347580) and EnVision anti-rabbit (Dako, K4003). Tissue sections were counterstained with Haematoxylin Z (CellPath). Stained slides were scanned using a Leica SCN400F scanner and analysed using HALO Image analysis software (Indica Labs). For Eµ-Myc tumours cell number and BrdU and caspase staining were quantified across the whole tumour with necrotic areas excluded. For APC$^{min/+}$ mice, single cross sections of the entire small intestine were analysed, adenomas were manually identified and cell number, caspase and BrdU staining in each adenoma was quantified and averaged for each mouse. Necrosis was quantified using H&E stained whole tumour cross sections, necrotic areas were manually defined using HALO software and total necrotic versus non-necrotic surface area were calculated.

Glucose and Lactate Quantification

Serum (from terminal blood samples) from mouse cohorts were analysed for glucose and lactate levels using an Agilent 2100 Bioanalyser (Agilent Technologies) according to the manufacturers instructions.

Macropinocytosis Assay

Analysis of macropinocytosis was based on a previously descried protocol (Commisso et al., *Nature*, 2013). Initially, iKRAS cells were grown with (KRas-ON) or without (KRas-OFF) doxycycline for 48 h. Cells were then seeded onto glass coverslips in medium+/−doxycycline and +/−SG. After 24 h the medium was replaced with matched medium lacking FBS and left for a further 16 h. Finally, medium was replaced with matched medium containing 10% FBS and Tetramethylrhodamine labeled dextran (TMR-dextran, Thermo Fisher Scientific) particles (0.5 mg/ml). After 30 minutes with dextran, cells were washed with PBS and fixed in 4% formaldehyde. Cells were counterstained with DAPI and green Whole Cell Stain (Thermo Scientific) and mounted in Vectasheild Hardset (Vector Laboratories). Images were captured on an Olympus FV1000 inverted laser scanning confocal microscope and dextran uptake was quantified using ImageJ/Fiji image analysis software.

Western Blot

Western blots on cells were performed as described previously (Maddocks et al, *Nature*, 2013; Labuschagne et al., *Cell. Rep.*, 2014; Maddocks et al, *Mol. Cell*, 2016), briefly, whole-cell protein lysates were prepared in RIPA-buffer supplemented with complete protease inhibitors (Roche), sodium orthovanadate, and sodium fluoride (both Sigma). Tissue samples were lysed in RIPA buffer supplemented with protease and phosphatase inhibitor cocktail (Pierce/Thermo Scientific) using a TissueLyser II (Qiagen). Lysates were cleared by centrifugation and separated using precast 4-12% 'NuPAGE' or 'Bolt' gels (Invitrogen, Life Technologies) and transferred to nitrocellulose membranes. Proteins were detected and quantified using a Li-Cor Odyssey Infrared scanner and software (Li-Cor Biosciences). Secondary antibodies for the relevant species were IRDye680 and IRDye800 conjugated (Li-Cor Biosciences). Primary antibodies used were: PHGDH (Sigma Life Science, HPA021241), PSAT1 (Novus Biologicals, NBP1-32920), PSPH (Santa Cruz, sc-98683), Actin I-19-R (Santa-Cruz, sc-1616-R), pERK [Phospho-p44/p42 MAPK (Erk1/2) (Thr202/Tyr204)] (Cell Signalling Technology 9101), AMPKa1 (R&D Systems, AF3197) and Phospho-AMPK T172 (Cell Signalling Technology 2535).

Statistics

Statistical comparisons for survival data were calculated with Graphpad Prism (v6) software using Mantel-Cox (Log Rank) test. T-tests were either performed using Microsoft excel (v14.6.1) or Graphpad Prism (v7). Type-1/paired (e.g. samples taken from the same animal) and type-2/unpaired (e.g. samples taken from different animals) T-tests were used. Where no prediction was made about the direction of potential difference a two-sided/two tailed T-test was used (e.g. across all amino acid levels in serum samples, FIG. 1c/Extended Data FIG. 2a). Where pre-existing data supported a prediction in the direction of difference between samples a one-sided/one tailed T-test was used (e.g. de novo serine synthesis, FIG. 4c). Where data presented is the mean of individual data-points error bars are STDEV, where data is a mean of means error bars are SEM. In each instance the relevant type of T-test or error bar is specified in the figure legend. Where T-tests were performed with multiple comparisons, P values were corrected using the Holm-Sidak method using Graphpad Prism (v7) software.

Results

Figure 24:
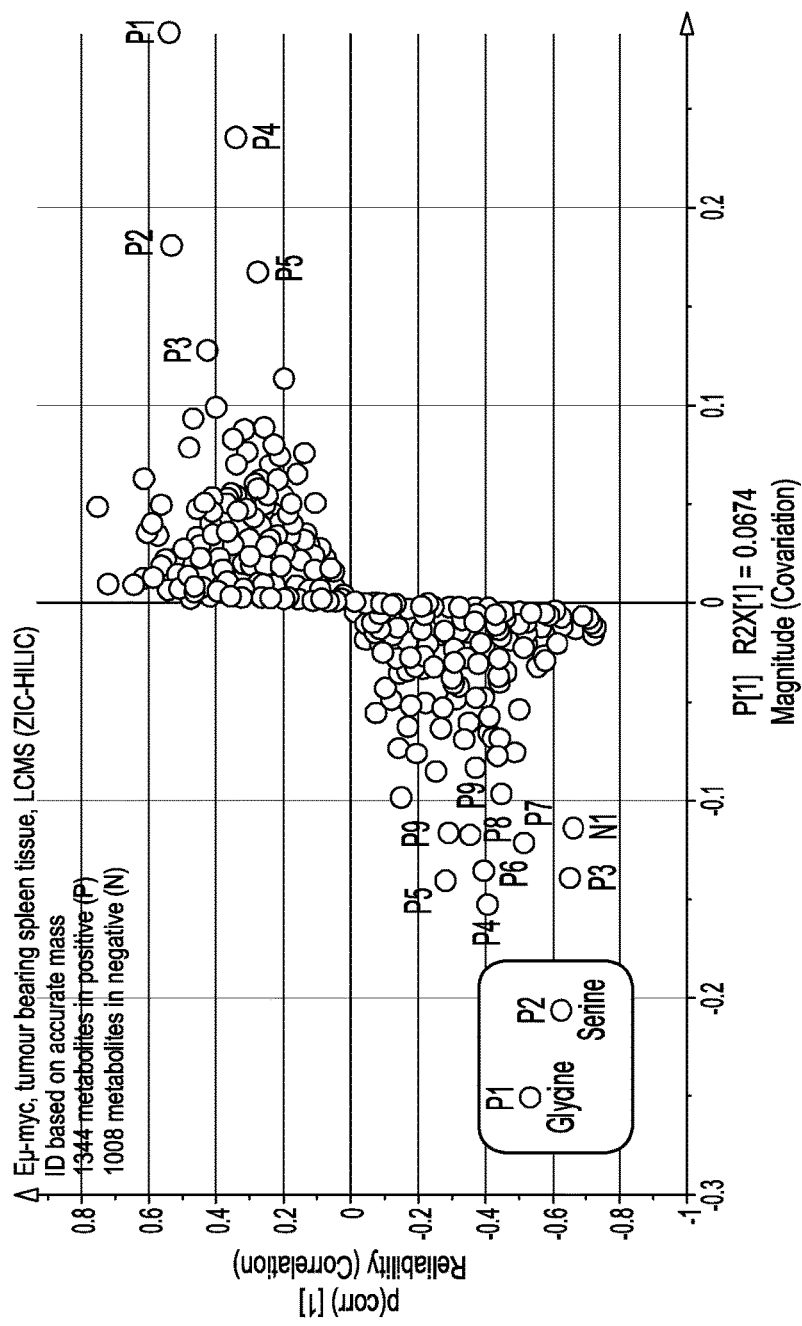
FIG. 24. S-plot of unbiased metabolomics analysis (OPLS-DA; orthogonal partial least squares discriminant analysis) of Eμ-myc tumour tissue (tumour bearing spleens) (Ctr n=20, −SG n=13). The detected metabolites showing the greatest decrease due to diet are serine and glycine. Decreased levels of carnitine-related and choline-related metabolites were also observed. Increased levels of phosphatidylcholine (PC) metabolites and alanine and threonine were also seen. SG starvation is known to influence glycolysis and OXPHOS (potentially explaining changes in carnitine and alanine levels), and one-carbon metabolism (potentially explaining changes in choline related metabolites).

Unbiased metabolomics showed that the most decreased metabolites in Eμ-Myc tumour tissues (tumour bearing spleens) on the −SG diet were serine and glycine, which demonstrated that the diet specifically lowered tumour levels of serine and glycine (FIG. 24).

Figure 25:
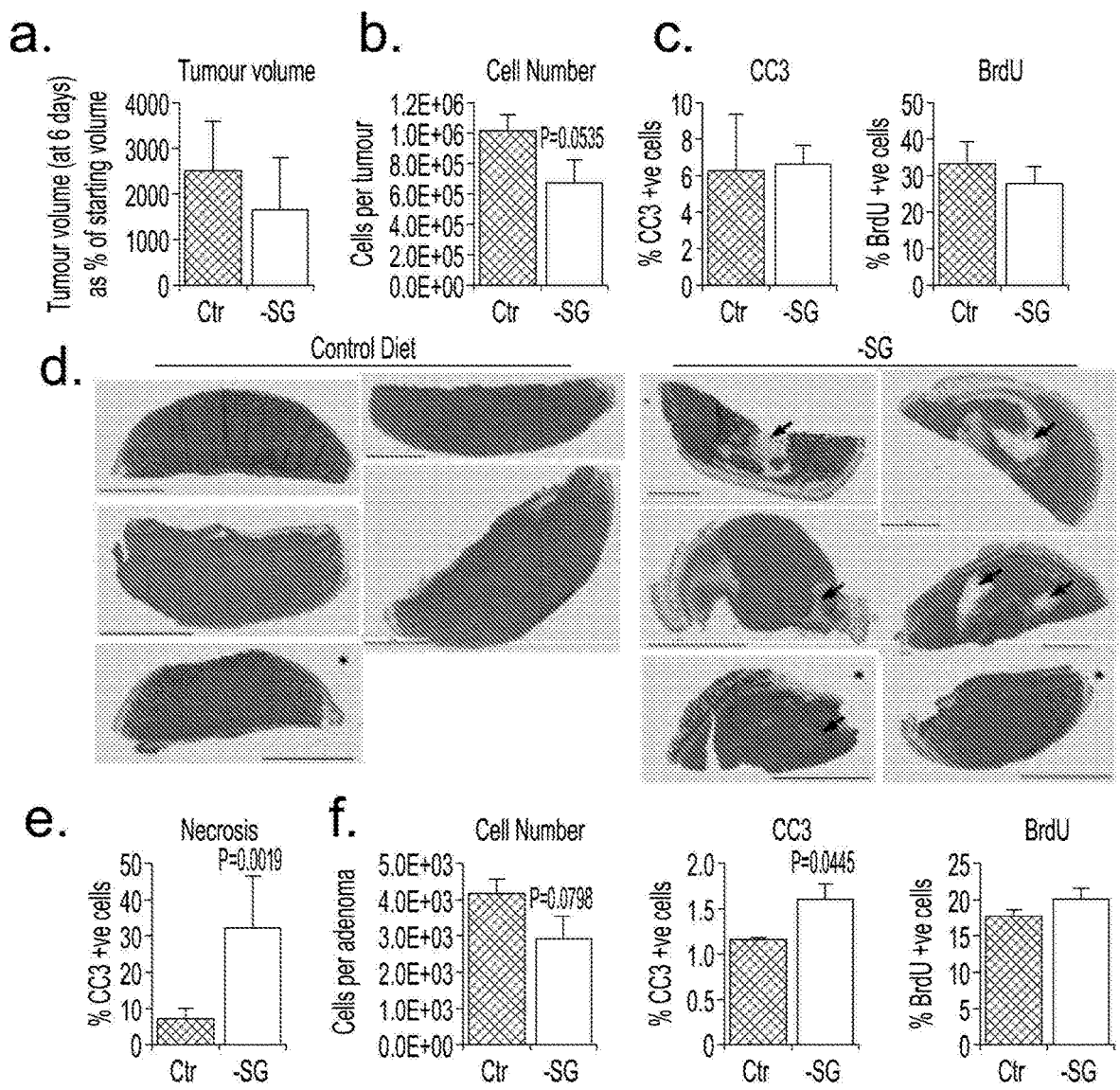
FIG. 25. Show the effects of the −SG diet on Eu-myc tumour cells. a. Lymphoma cell were isolated from Eμ-myc mice and expanded in culture. Cells were injected sub-cutaneously (5×10^5/flank) into nude mice and allowed to form tumours. Once tumours (Ctr n=4, −SG n=4) were visible and measurable, mice were transferred to control (Ctr) or serine & glycine free diet (−SG). Mice were sacrificed and tumours excised at single temporal end-point (6 days on diet). Average tumour volume (as percentage of starting tumour volume is shown, error bars=STDEV. b, To assess cell number per sub-cutaneous Eμ-myc tumour, two separate cell counts per tumour (using H&E stained cross-sections) were performed and averaged, mean of means is shown, error bars=SEM. P values calculated by T-test (unpaired, one-tail). c, Whole sub-cutaneous Eμ-myc tumour tissue sections (Ctr n=3, −SG n=4) were immuno-stained for cleaved caspase-3 (CC3) and BrdU. Image analysis of non-necrotic regions of whole tumours allowed quantitative evaluation of % cleaved caspase-3 positive cells per tumour and % BrdU positive cells per per tumour. Data are averages, error bars=STDEV. d. Eμ-myc tumour (as described in a-c above) cross-sections were H&E stained, the scale bar for each image is 4 mm, demonstrative necrotic regions marked with arrows. Additional tumour tissue sections (marked with *) are included for comparison from tumours which developed after diet change (these three tumours were measurable two days post diet change and were present for 4 days on diet before end-point). e. Necrosis was quantified by image analysis of necrotic & non-necrotic surface area of H&E stains for the sections shown in (d). Error bars=STDEV, P-value was calculated by T-test (unpaired, one tail, Ctr, n=5; −SG, n=6). f, $APC^{min/+}$ mice were placed on control diet (Ctr,n=3) or serine & glycine free diet (−SG, n=3) at 80 days of age. At a single temporal end-point (14 days on diet) mice were sacrificed and the small intestine was removed for histological analysis. Tissue sections were immuno-stained for cleaved caspase-3 and BrdU. Image analysis of whole intestines allowed quantitative evaluation of cell number per adenoma, % CC3 positive cells and % BrdU positive cells per adenoma. Data are averages of all adenomas identified in each small intestine section, error bars=SEM, P-values calculated by T-test (unpaired, one tail). For all analyses (a-f), P values below 0.1 are shown.

The effects of the −SG diet on Eμ-myc tumour cells in vivo showed that in some tumours there was an increase in apoptosis (as indicated by an increase in cleaved capsase-3 (CC3)) and in other tumours there was an increase in necrosis, both effects lead to inhibition or slowing of tumour growth (FIG. 25).

Figure 26:
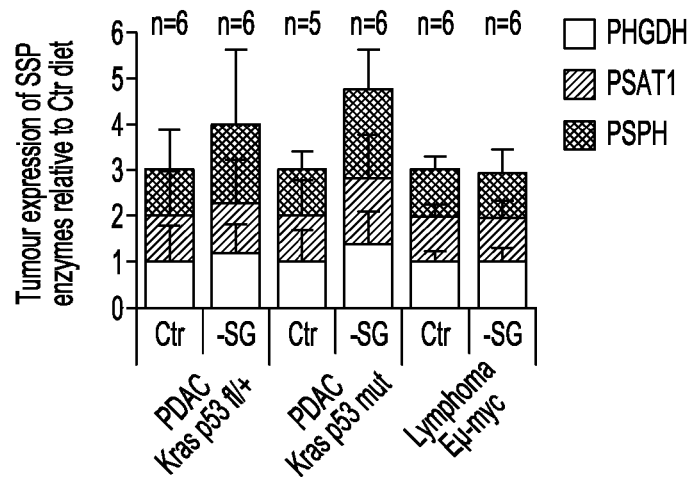
FIG. 26. Expression of SSP enzymes in tumour tissue from PDAC and Eμ-myc models. Protein lysates of PDAC tumours and tumour bearing spleens from Eμ-Myc mice that received the control or SG-free diet were analysed for SSP enzyme expression by western blot quantified using a Li-Cor scanner. Relative expression (versus control diet) of SSP enzymes is shown. Error bars=STDEV. Each tissue sample was taken from a different mouse, numbers of mice/tumours are shown above the bars.

Expression of SSP enzymes in tumour tissue from PDAC and Eu-myc models was also analysed when grown on control and −SG diets. These results suggested that Kras controls SSP in vivo. (FIG. 26). Moreover, tumour-organoids (3D cell cultures) which express Kras were observed to be more resistant to serine and glycine starvation, which also indicated that Kras controls SSP (FIG. 28).

Figure 27:
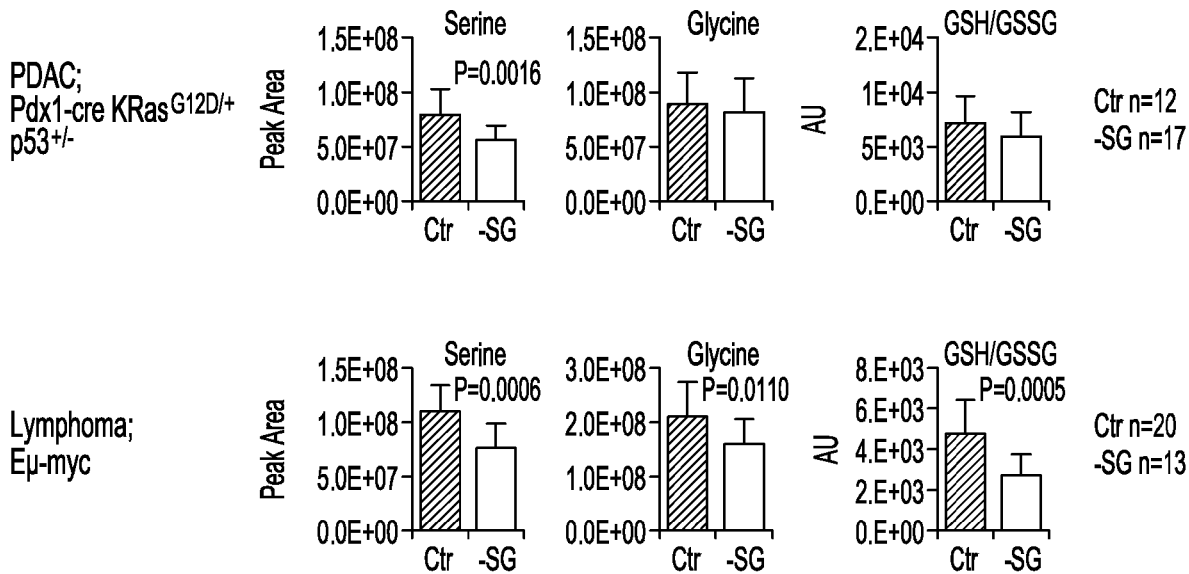
FIG. 27. Shows that a −SG diet led to decreased serine and glycine levels, and decreased GSH/GSSG ratio in Eu-myc tumours but no decrease in glycine or GSH/GSSG ratio in PDAC tumours. Pancreatic tumours from $Pdx1^{cre}$; $KRas^{G12D/+}$; $p53^{+/-}$ mice and tumour bearing spleens from Eμ-myc mice were analysed by LCMS for serine, glycine, GSH (reduced glutathione) and GSSG (oxidised glutathione). P values calculated by T-test, unpaired, two tails. Error bars=STDEV.

Moreover, a −SG diet led to decreased serine and glycine levels, and decreased GSH/GSSG ratio (sign of oxidative stress) in Eu-myc tumours (which are sensitive to the −SG diet). But, in PDAC tumours (which harbour Kras mutations, and are resistant to the diet) the −SG diet did not lower glycine levels or GSH/GSSG ratio (FIG. 27).

The −SG diet decreased growth of xenografted HCT116 tumours that had already formed in vivo (FIG. 29a), decreased intra-tumour serine and glycine levels (FIG. 29b). The lower tumour-levels of serine and glycine translated to slower cancer cell proliferation in vitro (FIGS. 29c & 29d).

Figure 30:
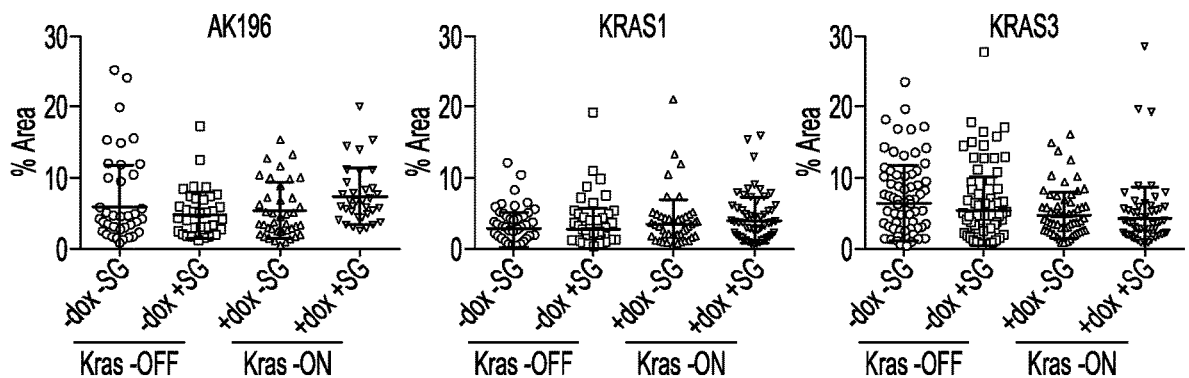
FIG. 30. Kras expressing cells obtain serine and glycine by de novo serine and glycine synthesis, not by an increase in micropinocytosis. Macropinocytosis in iKRas cells was assessed using TMR-labelled dextran uptake assay. Cells were initially grown +/−doxycycline for 48 h then seeded +/−doxycycline, +/−SG for 40 h (final 16 h without FBS), then given TMR dextran/FBS in matched medium for 30 minutes. Error bars & lines show average and STDEV.
Figure 31:
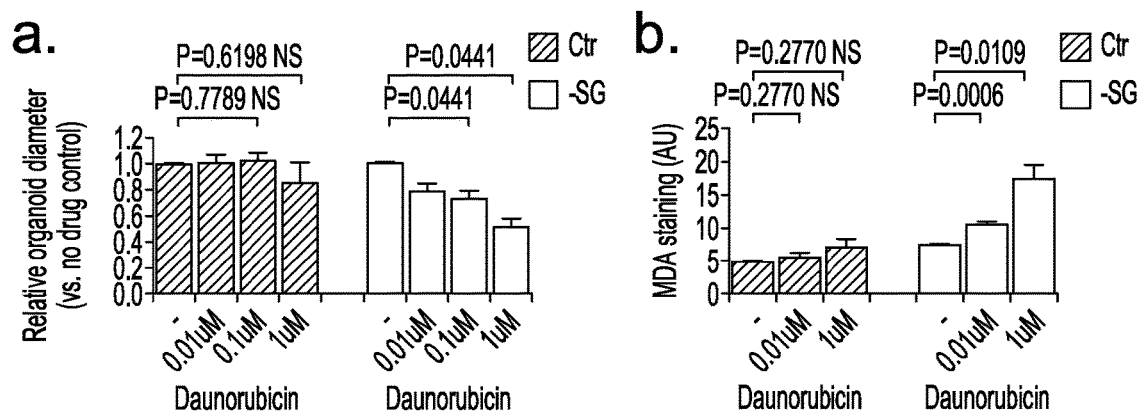
FIG. 31a. Daunorubicin complements serine and glycine starvation. Villin$^{creER}$; APC$^{fl/fl}$ mouse were grown +/−serine and glycine, +/−daunorubicin at the stated concentrations for two days. Relative change (versus '-drug') in organoid diameter is plotted. Data is average of three independent experiments, error bars=SEM. b. Villin$^{creER}$; APC$^{fl/fl}$ organoids were grown +/−serine and glycine +/−daunorubicin for two days, then fixed with and stained for malondialdehyde (MDA), data is average of three independent experiments, error bars=SEM. P values calculated by T-test (unpaired, two tails, with correction for multiple comparisons).

The data in FIG. 30 showed that the ability of Kras (in iKRAS1 iKRAS3 and AK196 cell lines) to obtain serine and glycine could not be explained by an increase in micropinocytosis (a form of nutrient scavenging), which further supports the idea that Kras expressing cells obtained additional serine and glycine by de novo serine and glycine synthesis. Macropinocytosis allows cells to capture and use extracellular nutrients by engulfing extracellular molecules (such as proteins, which can be catabolised into amino acids). In cultured cells, up-regulation of macropinocytosis corresponds with an increase in uptake of labelled dextran, and an increase in the % (cell) area with dextran staining. Across all three Kras-inducible cell lines, the uptake of labelled dextran was not increased during serine and glycine starvation, indicating that serine and glycine starvation did not result in increased macropinocytosis.

Data shown in FIGS. 31a and 31b shows that Daunorubicin (a conventional anti-cancer agent) worked with serine & glycine starvation to increase reactive oxygen species levels in tumour-organoids and decrease tumour organoid growth.

Example 7 (FIGS. 32, 33, 34, 35, 36, 37, 38, 39, 40)

Methods

Cell lines & Cell Culture

HCT116, SW480, MDA-MB-231, Panc10.05, CFPAC-1, SW1990, BxPC-3, AsPC-1, PANC-1, MIA PaCa-2 cells were originally obtained from ATCC and subsequently authenticated using Promega GenePrint 10. Breast and colorectal cancer cells were grown in DMEM (Gibco-21969) supplemented with 10% FBS (10270), penicillin-streptomycin & amphotericin with L-glutamine at final concentration of 2 mM. Pancreatic cancer cell lines were grown in RPMI-1640 (Gibco-31870) medium supplemented with 10% FBS (10270), penicillin-streptomycin & amphotericin with L-glutamine at final concentration of 2 mM and insulin-transferrin selenium solution (Gibco) 1:500. Cells were maintained in 37° C., 5% $CO_2$ humidified incubators. Cultured cells were routinely tested for mycoplasma using Mycoalert detection kit (Lonza).

Guide RNAs used to delete MTAP and non-targeting control

```
MTAP_gRNA_1F sequence ONE
CACCGGTTTTGCCCCAAAACGAGAG

MTAP_gRNA_1R sequence ONE
AAACCTCTCGTTTTGGGGCAAAACC

MTAP_gRNA_2F sequence TWO
CACCGGCCTGGTAGTTGACCTTTGA

MTAP_gRNA_2R sequence TWO
AAACTCAAAGGTCAACTACCAGGCC

NTC_gRNA_1F
CACCGAAAATAGCAGTAAACTCAAC

NTC_gRNA_1R
AAACGTTGAGTTTACTGCTATTTTC
```

The gRNA sequences were used together with the scaffold RNA to make a sgRNA in accordance with Ran et al (2013).

Proliferation Assays

Cells ($4 \times 10^4 - 1 \times 10^5$) were seeded in complete RPMI or DMEM medium in 24-well plates and allowed to adhere overnight. Cells were then washed with PBS and received assay medium supplemented with the stated amino acids/metabolites/drugs. Assay medium was formulated based on RPMI-1640 medium but lacking amino acids, which were added individually depending on the assay. Assay medium was also supplemented with additional vitamin B6 (20 uM), a co-factor for cysteine synthesis. Cells were counted (using Casy TT cell counter, Innovatis, Roche Applied Science) at the stated time-points, using a "time=0" plate to calculate relative cell number from time of medium change.

Microscopy

Images were captured using a Zeiss light microscope at 20× magnification coupled to a Zeiss Axiocam digital camera with Zeiss Zen software.

Liquid chromatography mass spectrometry (LCMS) Cells were grown in assay medium supplemented with the stated amino acids/metabolites. Universally labeled carbon-13 methionine was purchased from Cambridge Isotopes/CK-Gas. Cell extracts and media samples were prepared in cold (−20° C.) lysis solvent (LS) consisting of methanol, acetonitrile, and $H_2O$ (50:30:20). Lysates were equalized based on cell number by counting replicate well before lysis. Following addition of LS to cells/medium samples, protein was allowed to precipitate and cleared by centrifugation. Extracts were analysed on an LCMS platform consisting of an Accela 600 LC system and an Exactive mass spectrometer (Thermo Scientific). Chromatography employed a ZIC-HILIC column (4.6 mm×150 mm, 3.5 μm) (Merck) with the mobile phase mixed by A=water with 0.1% formic acid (v/v) and B=acetonitrile with 0.1% formic acid. A gradient program starting at 20% of A and linearly increasing to 80% at 30 min was used followed by washing and re-equilibration steps. The total run time of the method 2 was 46 min. The LC stream was desolvated and ionised in the HESI probe. The Exactive mass spectrometer was operated in full scan mode over a mass range of 75-1,000 m/z at a resolution of 50,000 with polarity switching. The raw data was analysed by LCquan (Thermo Scientific) and MZMine 2.10 for metabolite identification and quantification.

Western Blot

Whole-cell protein lysates were prepared in RIPA-buffer supplemented with protease and phosphate inhibitor cocktail (Pierce/Thermo Scientific). Lysates were cleared by centrifugation and separated using precast 4-12% 'Bolt' gels (Invitrogen, Life Technologies) and transferred to nitrocellulose membranes. Proteins were detected and quantified using a Li-Cor Odyssey Infrared scanner and software (Li-Cor Biosciences). Secondary antibodies for the relevant species were IRDye680 and IRDye800 conjugated (Li-Cor Biosciences). Primary antibodies used were: rabbit anti-MTAP (Abcam).

Data Presentation

Data is plotted as averages with error bars showing standard deviation.

Figure 32:
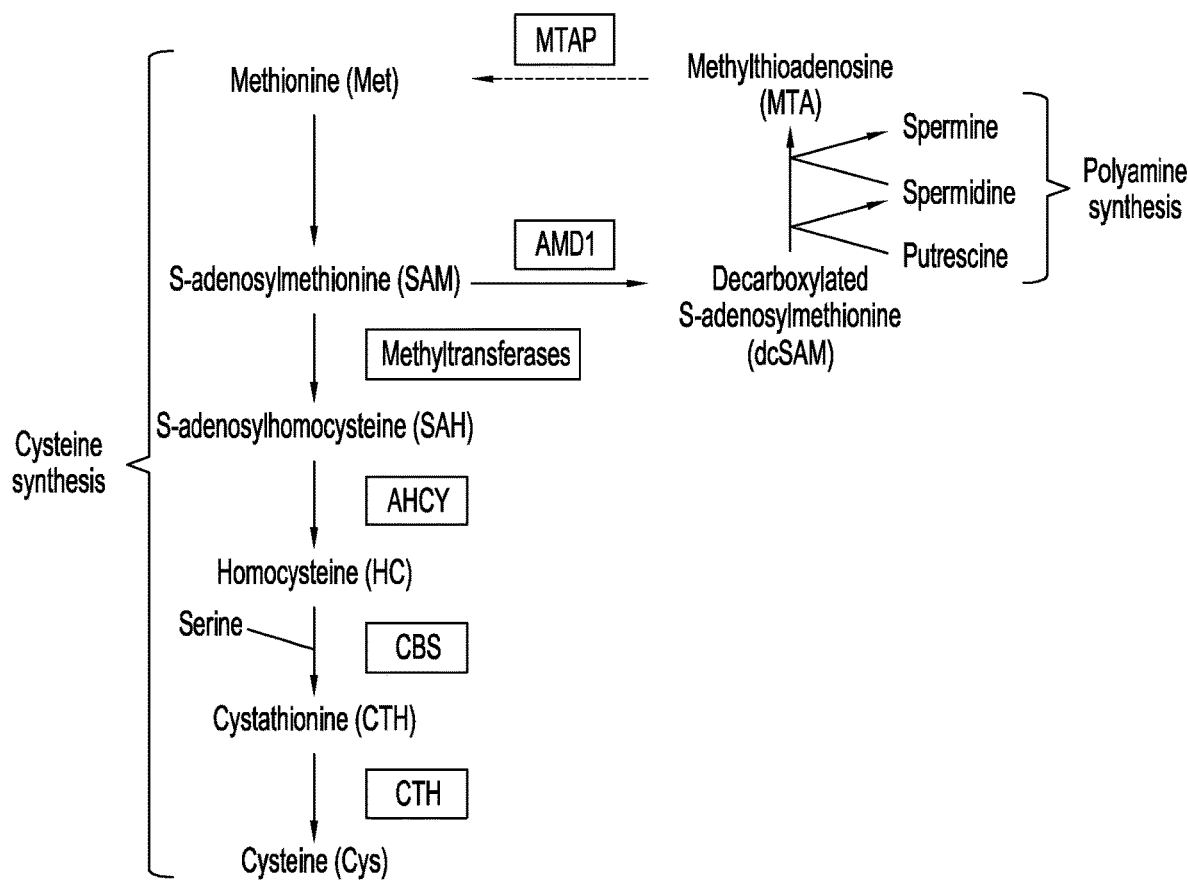
FIG. 32. Shows a simplified schematic diagram illustrating de novo cysteine synthesis and polyamine synthesis in humans. Metabolites are shown in normal text, enzymes are shown in boxes.

Overview of Cysteine Synthesis (FIG. 32)

Cysteine synthesis begins with the essential amino acid methionine, which is converted through multiple enzymatic steps into cysteine. Polyamines are crucial molecules for cell growth and proliferation, and polyamine synthesis has been found to be up-regulated in cancer. Polyamine synthesis requires the methionine derived metabolite dcSAM, which is converted into MTA during polyamine (spermine and spermidine) synthesis. MTA can be recycled back to methionine via a multi-step enzymatic pathway which includes the enzyme methylthioadenosine phosphorylase (MTAP). When MTAP is present, recycling of MTA produced in polyamine synthesis provides efficient methionine utilization. However, when MTAP is deleted (as frequently occurs in cancer) MTA cannot be recycled back to methionine, and is released from the cell. This means a constant supply of methionine is converted into MTA and ejected from the cell. This constant diversion of methionine into polyamine synthesis can prevent the utilization of methionine for other purposes such as cysteine synthesis.

Results

Figure 33:
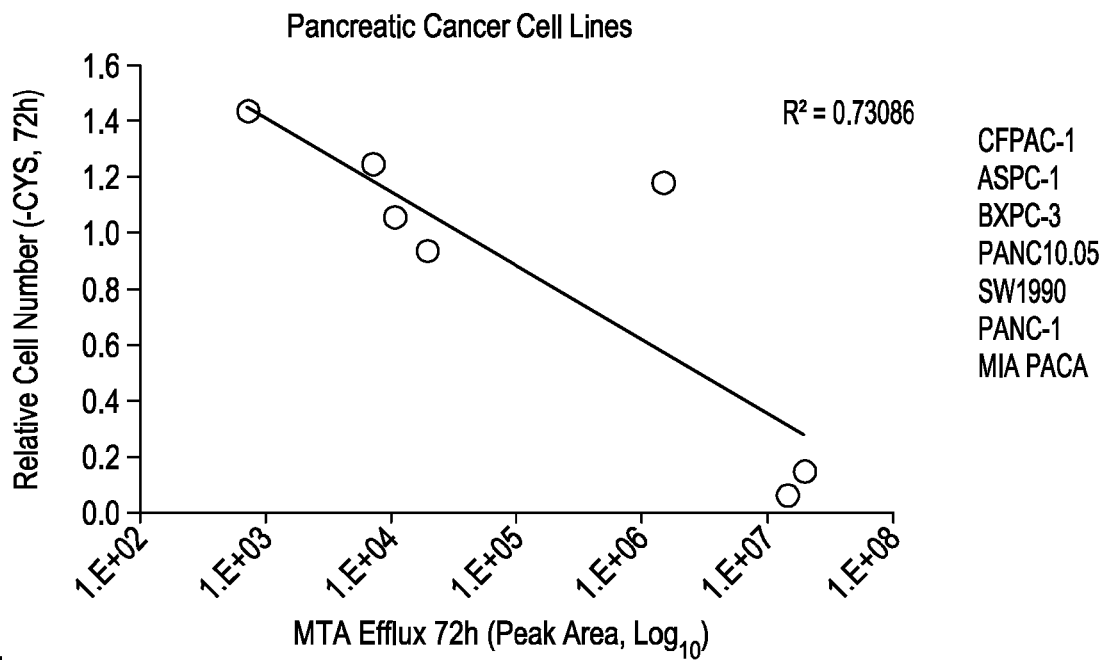
FIG. 33. Shows that MTA Efflux (which is an indicator of MTAP deletion/inactivation) correlates with enhanced sensitivity to cysteine starvation. a. Pancreatic cancer cell lines were grown in 24-well plates in formulated medium (based on RPMI medium) lacking cysteine but containing all 19 other essential and non-essential amino acids for three days. Cell numbers were counted using a CASY TT cell counter. Methylthioadenosine (MTA) levels in the cell culture medium were measured after 3 days by analysing samples of medium by liquid chromatography-mass spectrometry. b. Colorectal and breast cancer cell lines were grown in 24-well plates in formulated medium (based on RPMI medium) lacking cysteine but containing all 19 other essential and non-essential amino acids for three days. Cell numbers were counted using a CASY TT cell counter. Methylthioadenosine (MTA) levels in the cell culture medium were measured after 24 hours by analysing samples of medium by liquid chromatography-mass spectrometry. $R^2$=correlation coefficient (with Log trend-line) computed by MS Excel.
Figure 33:
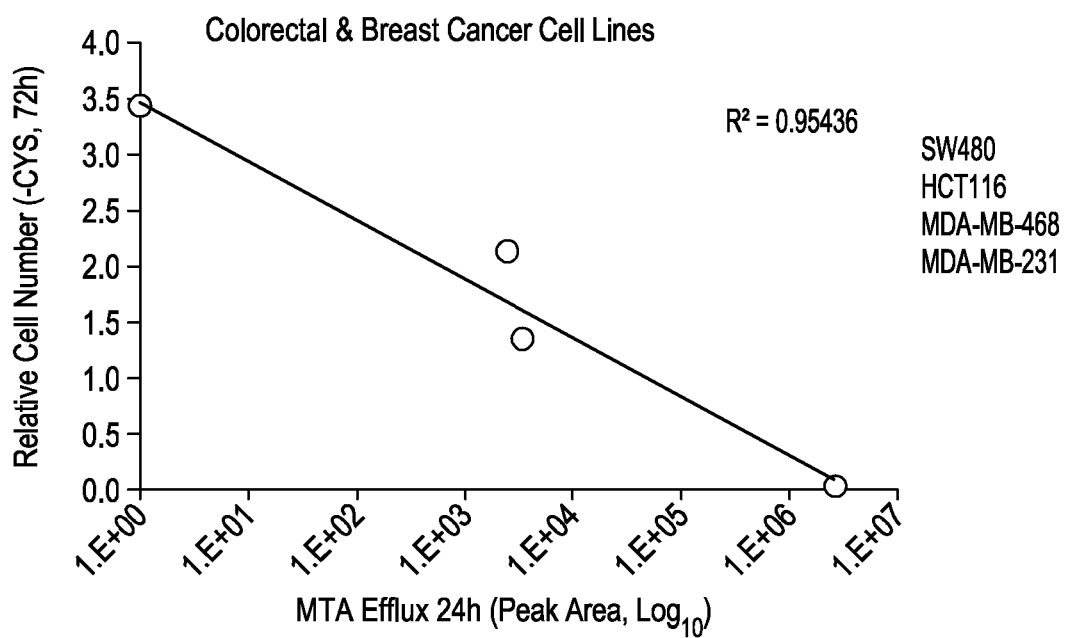

We have found that all cancer cell lines we have tested are to some extent sensitive to cysteine deprivation. Notably, certain cell lines such as MDA-MB-231 were found to be extremely sensitive to cysteine starvation, which causes dramatic cell death (FIG. 33, 40). Often nutrient deprivation (such as amino acid starvation) slows proliferation but doesn't necessarily induce acute cell death, so we investigated why certain cell lines were highly sensitive.

Figure 39:
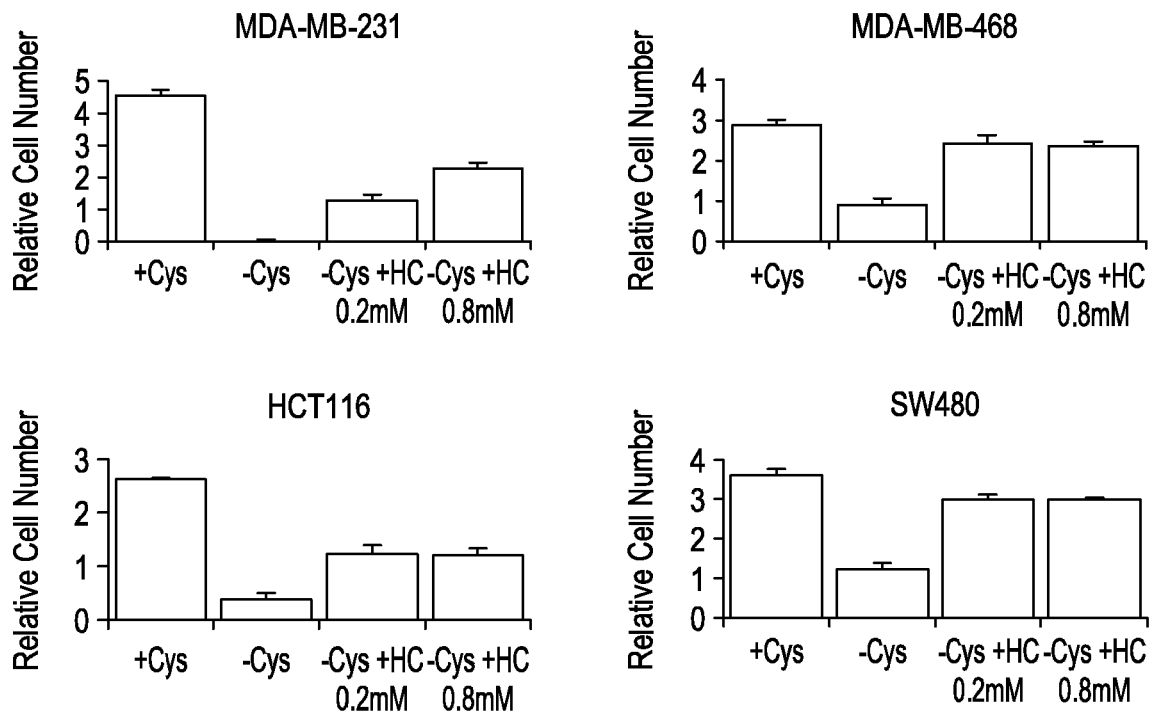
FIG. 39. Shows that cells can be rescued from cysteine starvation by supplementation with homocysteine this demonstrates that the enzymes CTH and CBS are expressed, active and able to conduct de novo cysteine synthesis when the precursor supply is adequate. This data supports the idea that precursor shortage (rather than, or in addition to, defective/inadequate CTH and CBS enzyme expression) contributes to sensitivity to cysteine starvation. Colorectal and breast cancer cell lines were grown in 24-well plates. Basal medium was formulated (based on RPMI medium) lacking cysteine but containing all 19 other essential and non-essential amino acids. This basal medium was supplemented with the stated components; cysteine 0.4 mM (+Cys), homocysteine 0.2 mM & 0.8 mM (HC) and grown for three days. Data are average of three wells. Error bars=STDEV.

Whilst it has been previously reported that cysteine starvation can be harmful to cancer cells and that this sensitivity may be due to inactivation of genes for the synthesis of cysteine (e.g. methylation of the gene for CBS) our results surprisingly show that supplementing cells with a metabolic precursor upstream of CBS (homocysteine) achieves significant rescue from cysteine starvation (FIG. 39). This suggests that the enzymes for cysteine synthesis are present and active, but that there is a problem with supply of the upstream precursors (such as homocysteine) for cysteine synthesis.

Figure 34:
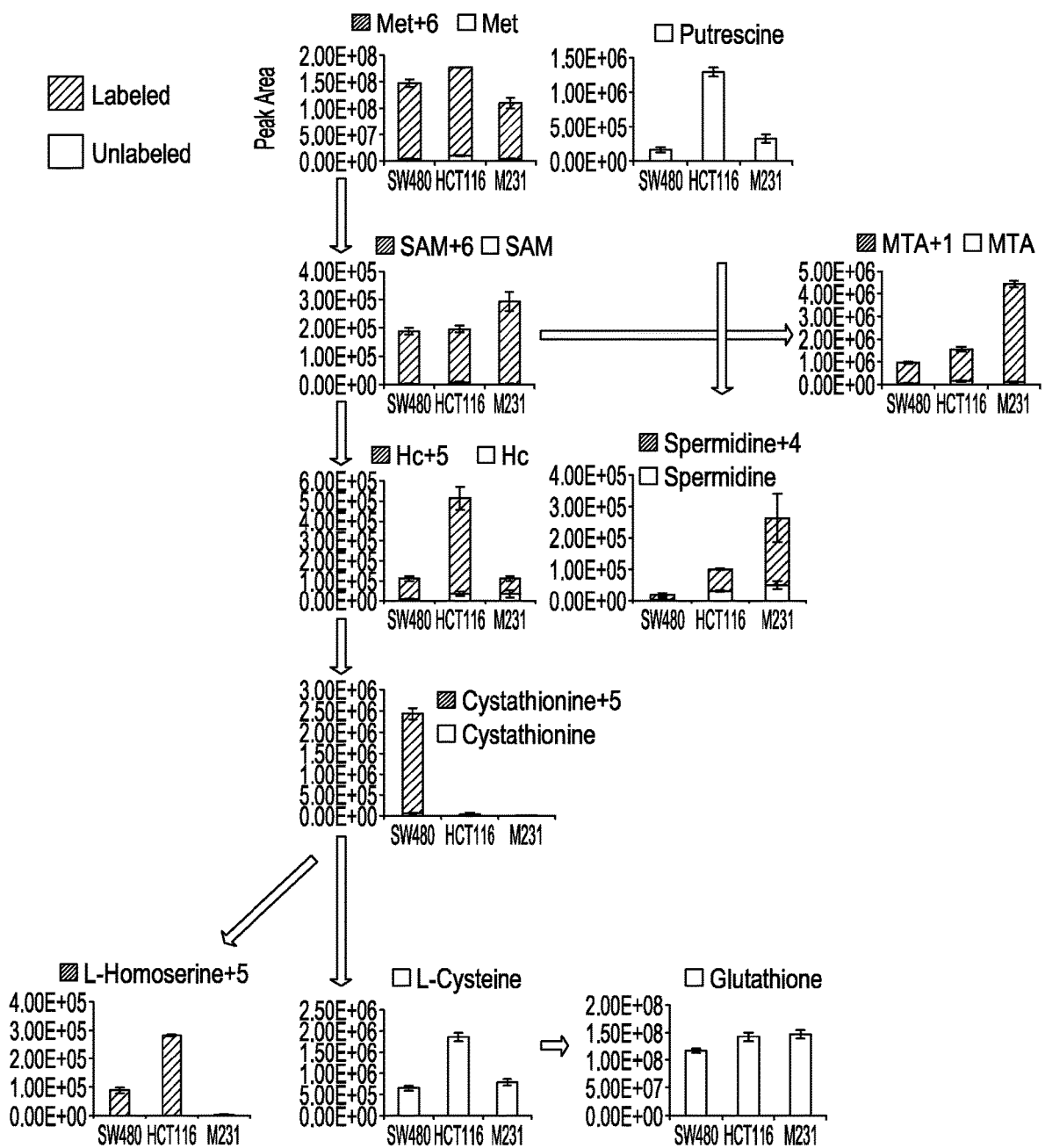
FIG. 34. Shows that MDA-MB-231 cells have a higher rate of MTA and spermidine synthesis indicating that large amounts of methionine are diverted into the polyamine pathway in these cells. By contrast, in HCT116 and SW480 cells less methionine is diverted into the polyamine pathway and more methionine reaches homocysteine/cystathionine which can be converted into cysteine. This helps to explain the better survival of HCT116 and SW480 cells during cysteine starvation. SW480 and MDA-MB-231 (M231) cells were grown in formulated medium (based on RPMI medium lacking carbon-12 methionine, supplemented with carbon-13 labelled methionine and containing all 19 other essential and non-essential amino acids for two days. Cell lysates were analysed by liquid chromatography-mass spectrometry. The most abundant isotopomers are shown. MTA=methylthioadenosine, Met=methionine, Hc=homocysteine, SAM=S-adenosylmethionine. M+x=mass plus x units.
Figure 35:
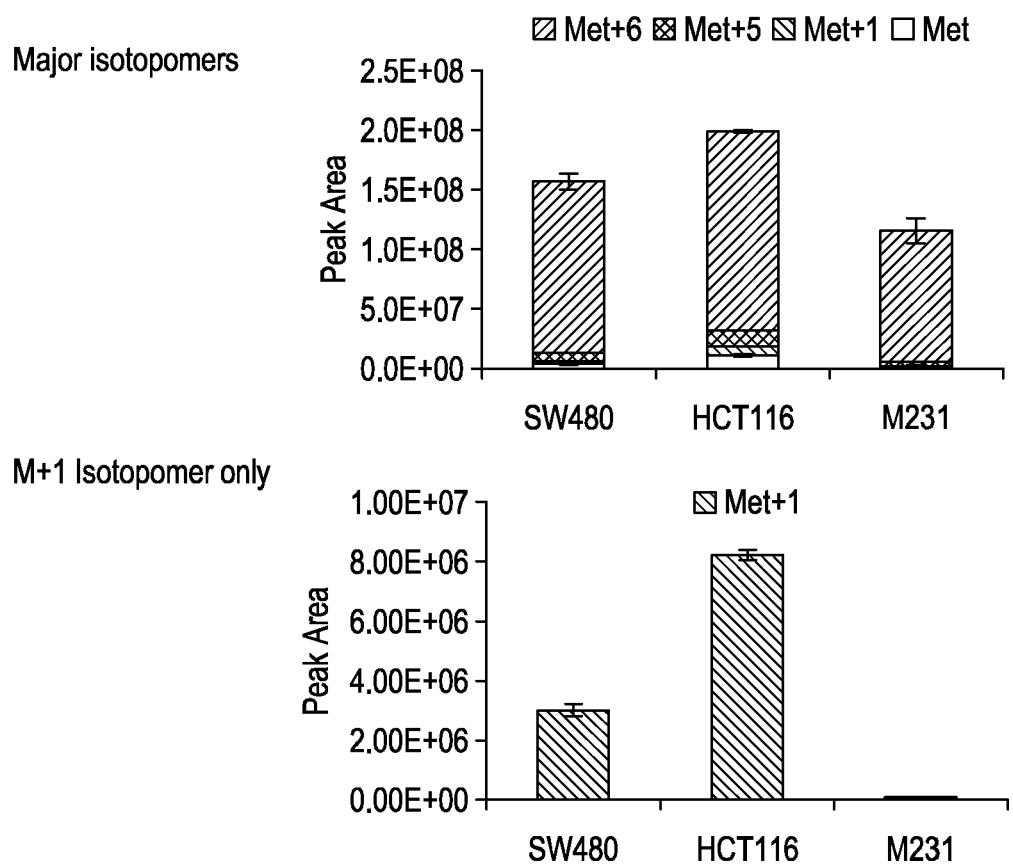
FIG. 35. Shows that HCT116 and SW480 cells are able to recycle MTA back to methionine, but that MDA-MB-231 cells (which efflux MTA) are unable to recycle MTA back to methionine. Metabolite tracing with carbon-13 labelled methionine shows that unlike MDA-MB-231 cells, SW480 and HCT116 cells are able to recycle methionine which has been used in the polyamine pathway (via MTA), which appears as 'm+1' methionine. HCT116, SW480 and MDA-MB-231 (M231) cells were grown in formulated medium (based on RPMI medium lacking carbon-12 methionine, supplemented with carbon-13 labelled methionine and containing all 19 other essential and non-essential amino acids for two days. Cell lysates were analysed by liquid chromatography-mass spectrometry. Major methionine isotopomers are shown.
Figure 36:
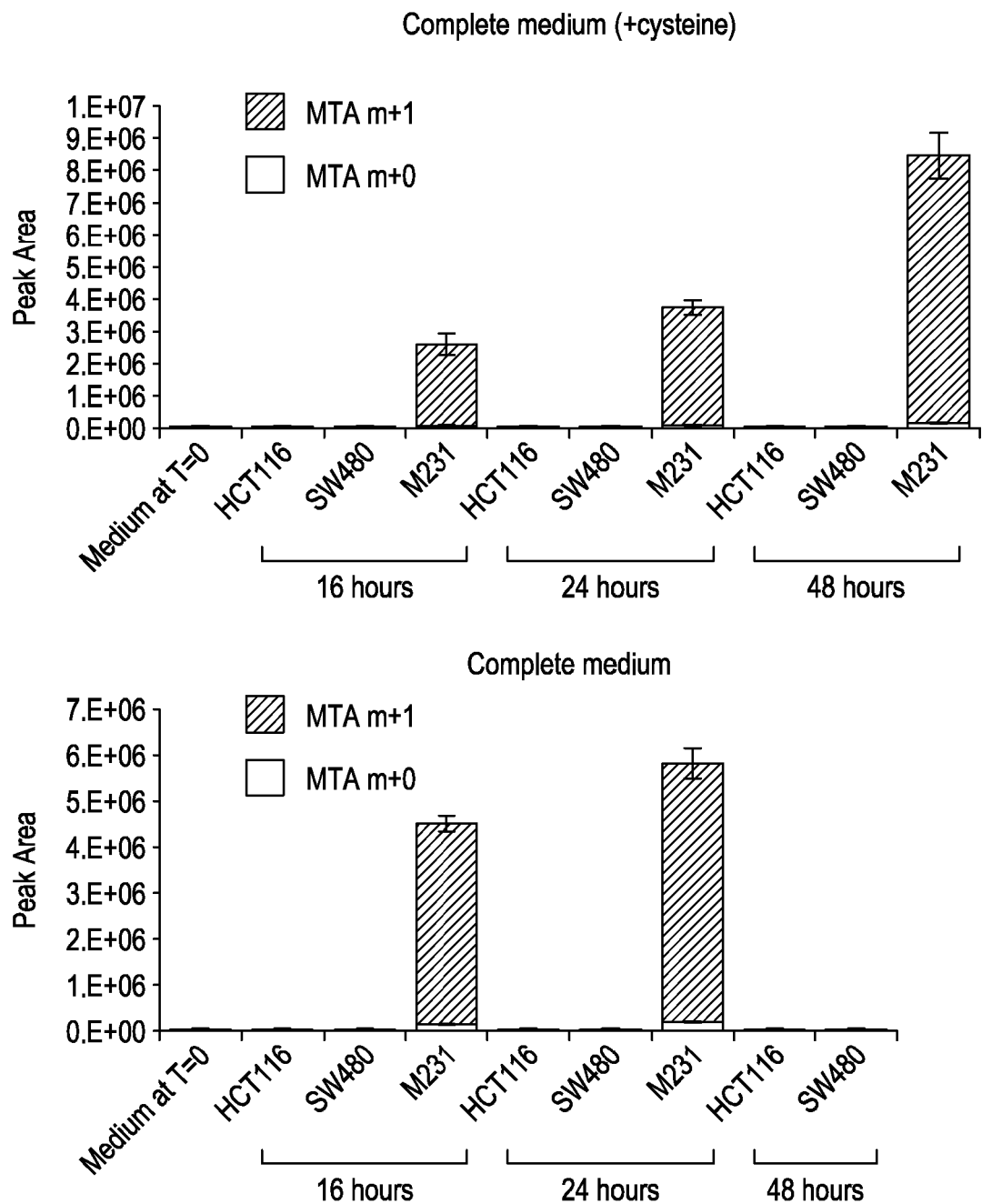
FIG. 36. Shows that MDA-MB-231 (M231) cells have significant efflux of MTA compared with HCT116 and SW480 cells, and even continue to efflux MTA during cysteine starvation. HCT116, SW480 and MDA-MB-231 (M231) cells were grown in formulated medium (based on RPMI medium), with or without cysteine, lacking carbon-12 methionine, supplemented with carbon-13 labelled methionine and containing all 19 other essential and non-essential amino acids for two days. Metabolite extracts were prepared from medium samples (taken at the specified time-points) and were analysed by liquid chromatography-mass spectrometry. MTA=methylthioadenosine. M+x=mass plus x-units. There is no data for MDA-MB-231 cells at 48 h in cysteine starvation because no live cells were remaining by that time-point.
Figure 37:
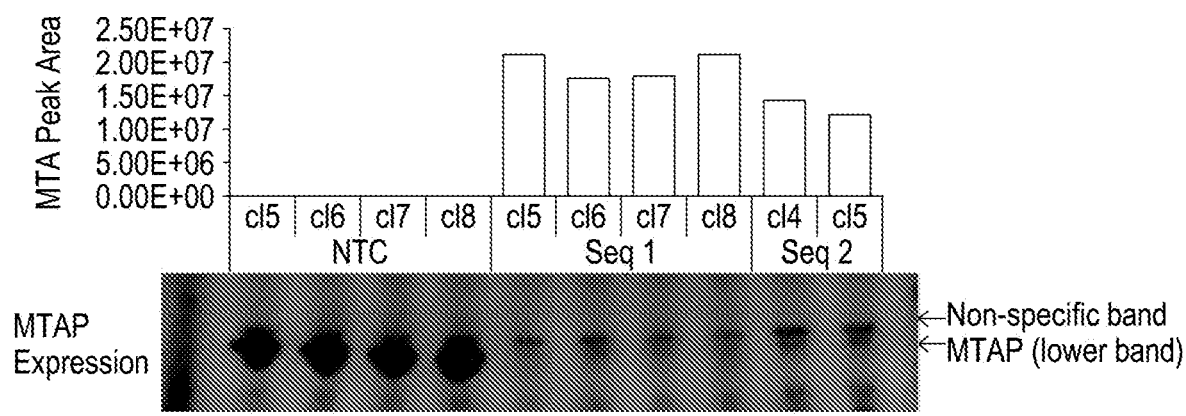
FIG. 37. Shows that by knocking-out MTAP gene expression leads to induction of MTA efflux. HCT116 cells were transfected with CRISPR/Cas9 and targeting sequences (Seq 1 & 2) for MTAP or with a non-targeting control sequence (NTC). Several clones were isolated from each sequence and grown in complete medium for 4 days. Protein lysates were analysed for MTAP expression by western blot. Samples of medium were analysed for MTA content by liquid-chromatography mass spectrometry.
Figure 38:
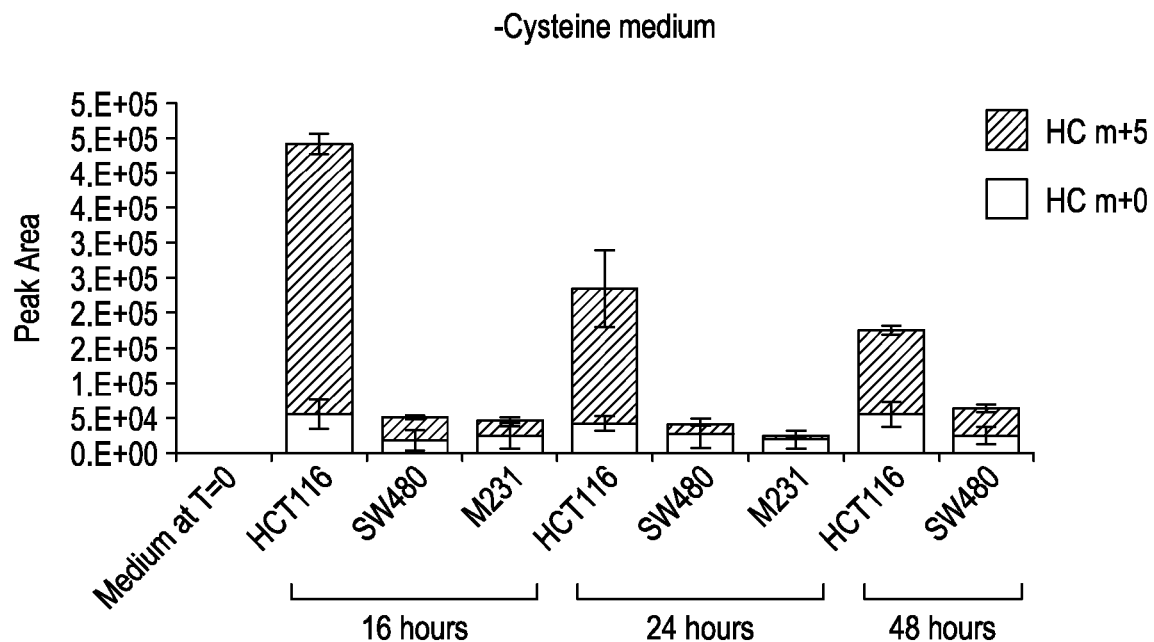
FIG. 38. Shows that HCT116 efflux homocysteine (an upstream precursor of cysteine) but they are able to re-uptake homocysteine during cysteine starvation. HCT116 cells are still sensitive to cysteine starvation, but less so than MDA-MB-231 (M231) cells. HCT116, SW480 and MDA-MB-231 (M231) cells were grown in formulated medium (based on RPMI medium), with or without cysteine, lacking carbon-12 methionine, supplemented with carbon-13 labelled methionine and containing all 19 other essential and non-essential amino acids for two days. Metabolite extracts were prepared from medium samples (taken at the specified time-points) and were analysed by liquid chromatography-mass spectrometry. HC=homocysteine. M+x=mass plus x-units. There is no data for MDA-MB-231 cells at 48 h in cysteine starvation because no live cells were remaining by that time-point.
Figure 40:
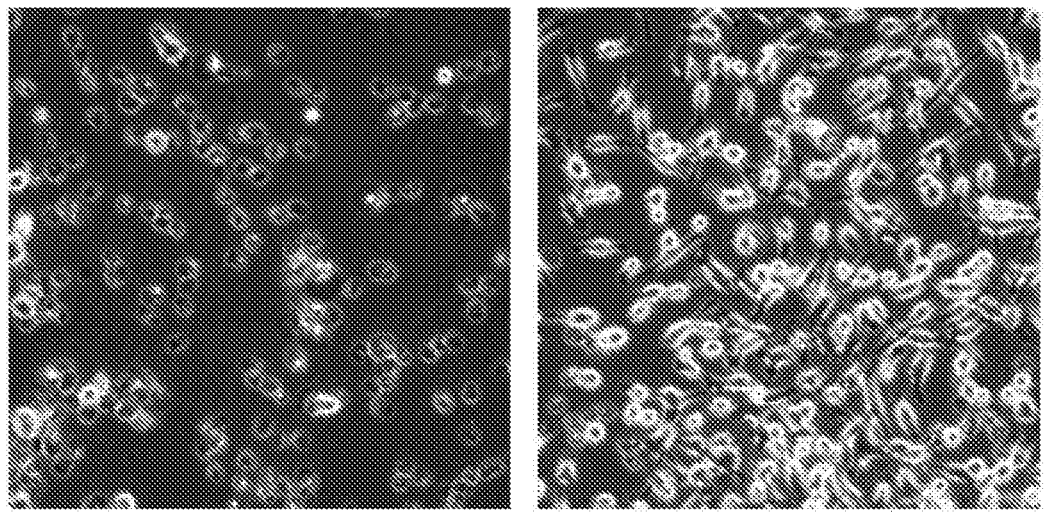
FIG. 40. Shows that inhibition of AMD1 (the enzyme which diverts methionine-derived SAM into the polyamine synthesis pathway) protects cells from acute sensitivity (i.e. cell death) to cysteine starvation. MDA-MB-231 cells were initially seeded in complete (DMEM) medium in 24-well plates. After 24 h, cells were treated with AMD1 inhibitor Sardomozide (20 uM) for 16 h or left untreated (Ctr). Cells were then washed with PBS and given medium lacking cysteine but containing all 19 other amino acids. Images (a) were captured using a light microscope, and cell counts (b) were performed using a CASY TT cell counter. Data are average of three wells. Error bars=STDEV.
Figure 40:
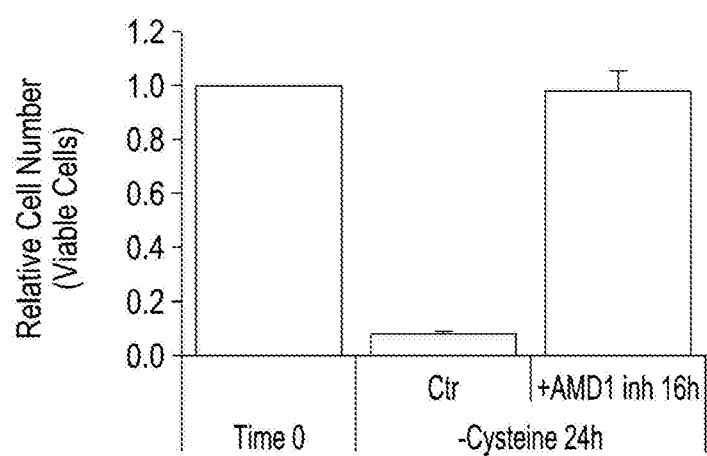

Whilst it has been suggested that expression of the enzymes for de novo cysteine synthesis, particularly CBS and CTH can determine sensitivity to cysteine starvation, we have surprisingly found that the cells which are most acutely sensitive to cysteine starvation are those that efflux the methionine derived metabolite MTA (FIG. 33, 34, 36, 32). MTA efflux closely correlates with acute sensitivity to cysteine starvation (FIG. 33, 39, 36). MTA efflux is caused by inactivation or deletion of the gene encoding the enzyme MTAP (FIG. 37). MTAP functions to recycle MTA back to methionine and therefore provides efficient methionine metabolism (FIG. 34, 35). In the absence of MTA large amounts of methionine is diverted into the polyamine pathway and not to the cysteine synthesis pathway (FIG. 34). Consistent with this finding is that inhibition of AMD1 (the enzyme which diverts methionine-derived SAM into the polyamine synthesis pathway) is able to protect cells from acute sensitivity (i.e. cell death) to cysteine starvation (FIG. 40).

In the context of using diet to treat cancer; based on our in vitro work, most cancer cell lines are sensitive to cysteine starvation, but a subset are particularly sensitive (FIG. 33). Our work shows that loss of MTAP expression strongly correlates with acute sensitivity to cysteine starvation (FIG. 33). Cells with loss of MTAP display a diversion of metabolic precursors upstream of cysteine synthesis (FIG. 34). MTAP is a commonly deleted/inactivated in cancer/tumour cells (Bertino et al. 2011). Our findings suggest that tumours lacking MTAP expression will be particularly sensitive to cysteine starvation.

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

REFERENCES

Ying, H. et al. Oncogenic Kras maintains pancreatic tumors through regulation of anabolic glucose metabolism. *Cell* 149, 656-670, doi:10.1016/j.cell.2012.01.058 (2012)

Labuschagne, C. F., van den Broek, N. J., Mackay, G. M., Vousden, K. H., and Maddocks, O. D. (2014). Serine, but not glycine, supports one-carbon metabolism and proliferation of cancer cells. Cell Rep 7, 1248-1258.

Maddocks, O. D., Berkers, C. R., Mason, S. M., Zheng, L., Blyth, K., Gottlieb, E., and Vousden, K. H. (2013). Serine starvation induces stress and p53-dependent metabolic remodelling in cancer cells. Nature 493, 542-546.

Bunz, F., Dutriaux, A., Lengauer, C., Waldman, T., Zhou, S., Brown, J. P., Sedivy, J. M., Kinzler, K. W., and Vogelstein, B. (1998). Requirement for p53 and p21 to sustain G2 arrest after DNA damage. Science 282, 1497-1501.

Donehower, L. A., Harvey, M., Slagle, B. L., McArthur, M. J., Montgomery, C. A., Jr., Butel, J. S., and Bradley, A. (1992). Mice deficient for p53 are developmentally normal but susceptible to spontaneous tumours. Nature 356, 215-221.

Vigneron, A. M., Ludwig, R. L., and Vousden, K. H. Cytoplasmic ASPP1 inhibits apoptosis through the control of YAP. Genes Dev 24, 2430-2439.

Hirakawa, D. A., Olson, L. M. & Baker, D. H. Comparative Utilization of a Crystalline Amino-Acid Diet and a Methionine-Fortified Casein Diet by Young-Rats and Mice. *Nutr Res* 4, 891-895, doi:Doi 10.1016/S0271-5317 (84)80064-0 (1984).

Zhang, T. et al. Application of Holistic Liquid Chromatography-High Resolution Mass Spectrometry Based Urinary Metabolomics for Prostate Cancer Detection and Biomarker Discovery. PLoS One 8, e65880, doi:10.1371/journal.pone.0065880 (2013).

Adams, J. M. et al. The c-myc oncogene driven by immunoglobulin enhancers induces lymphoid malignancy in transgenic mice. Nature 318, 533-538 (1985).

Moser, A. R., Pitot, H. C. & Dove, W. F. A dominant mutation that predisposes to multiple intestinal neoplasia in the mouse. Science 247, 322-324 (1990).

Su, L. K. et al. Multiple intestinal neoplasia caused by a mutation in the murine homolog of the APC gene. Science 256, 668-670 (1992).

Barker, N. et al. Crypt stem cells as the cells-of-origin of intestinal cancer. Nature 457, 608-611, doi:10.1038/nature07602 (2009).

Hingorani, S. R. et al. Trp53R172H and KrasG12D cooperate to promote chromosomal instability and widely metastatic pancreatic ductal adenocarcinoma in mice. Cancer Cell 7, 469-483, doi:10.1016/j.ccr.2005.04.023 (2005).

Morton, J. P. et al. Mutant p53 drives metastasis and overcomes growth arrest/senescence in pancreatic cancer. Proc Natl Acad Sci USA 107, 246-251, doi:10.1073/pnas.0908428107 (2010).

Commisso, C. et al. Macropinocytosis of protein is an amino acid supply route in Ras-transformed cells. Nature 497, 633-637, doi:10.1038/nature12138 (2013).

Maddocks, 0. D., Labuschagne, C. F., Adams, P. D. & Vousden, K. H. Serine Metabolism Supports the Methionine Cycle and DNA/RNA Methylation through De Novo ATP Synthesis in Cancer Cells. Mol Cell 61, 210-221, doi:10.1016/j.molce1.2015.12.014 (2016).

Bertino, J. R., Waud, R. W., Parker, W. B., and Lubin, M. Targeting tumours that lack methylthioadenosine phosphorylase (MTAP) activity. Cancer Biology & Therapy 11:8, 627-632, doi: 10.461/cbt.11.714948

Ran, F. A., Hsu, P. D., Wright, J., Agarwala, V., Scott, D. A., and Zhang, F. Genome engineering using the CRISPR-Cas9 system. Nauter Protocols. 8, 11, doi: 10.1038/nprot2013.143 (2013)

The invention claimed is:

1. A dietary product comprising:
   all essential amino acids, which consist of: histidine, isoleucine, leucine, lysine, methionine, phenylalanine, threonine, tryptophan, and valine, or prodrugs, salts, or esters of said amino acids;
   at least three additional amino acids selected from alanine, asparagine, aspartic acid, glutamic acid, glutamine, and proline, or prodrugs, salts, or esters of said amino acids;
   and optionally, further comprising one or more of the amino acids tyrosine or arginine, or prodrugs, salts, or esters of said amino acids;
   wherein the dietary product is devoid of the amino acids glycine, serine, and cysteine, and prodrugs, salts, and esters of said amino acids.

2. The dietary product of claim 1, wherein the dietary product is further devoid of arginine, or a prodrug, a salt, or an ester thereof.

3. The dietary product of claim 1, wherein the dietary product further comprises one or more macronutrients or one or more micronutrients.

4. The dietary product of claim 1, wherein the dietary product is formulated as a solid.

5. A pharmaceutical composition comprising:
   a. the dietary product of claim 1; and
   b. a pharmaceutically acceptable carrier, a pharmaceutically acceptable excipient, or a pharmaceutically acceptable diluent.

6. The dietary product of claim 1, wherein the dietary product is further devoid of arginine, or a prodrug, a salt, or an ester thereof, and tyrosine, or a prodrug, a salt, or an ester thereof.

7. The dietary product of claim 1, wherein the dietary product is further devoid of tyrosine, or a prodrug, a salt, or an ester thereof.

8. The dietary product of claim 1, wherein the dietary product further comprises methionine, or a salt, or an ester thereof, at a level of less than 25 mg/kg/day.

9. The dietary product of claim 3, wherein the one or more macronutrient is a fat.

10. The dietary product of claim 3, wherein the one or more micronutrient is magnesium.

11. The dietary product of claim 3, wherein the one or more micronutrient is calcium.

12. The dietary product of claim 3, wherein the one or more micronutrient is potassium.

13. The dietary product of claim 1, wherein the dietary product is formulated as a beverage.

14. The dietary product of claim 1, wherein the dietary product comprises alanine, or a prodrug, a salt, or an ester thereof.

15. The dietary product of claim 1, wherein the dietary product comprises arginine, or a prodrug, a salt, or an ester thereof.

16. The dietary product of claim 1, wherein the dietary product comprises asparagine, or a prodrug, a salt, or an ester thereof.

17. The dietary product of claim 1, wherein the dietary product comprises aspartic acid, or a prodrug, a salt, or an ester thereof.

18. The dietary product of claim 1, wherein the dietary product comprises glutamic acid, or a prodrug, a salt, or an ester thereof.

19. The dietary product of claim 1, wherein the dietary product comprises glutamine, or a prodrug, a salt, or an ester thereof.

20. The dietary product of claim 1, wherein the dietary product comprises proline, or a prodrug, a salt, or an ester thereof.

21. The dietary product of claim 1, wherein the dietary product comprises tyrosine, or a prodrug, a salt, or an ester thereof.

22. The dietary product of claim 1, wherein the dietary product decreases proliferation rate of a cancer cell.

* * * * *

SEQUENCE LISTING

```
<160> NUMBER OF SEQ ID NOS: 12

<210> SEQ ID NO 1
<211> LENGTH: 21
<212> TYPE: DNA
<213> ORGANISM: Artificial Sequence
<220> FEATURE:
<223> OTHER INFORMATION: Forward Primer Mouse PSAT1

<400> SEQUENCE: 1
tggcctcggc agaattggaa g                                          21

<210> SEQ ID NO 2
<211> LENGTH: 22
<212> TYPE: DNA
<213> ORGANISM: Artificial Sequence
<220> FEATURE:
<223> OTHER INFORMATION: Reverse Primer Mouse PHGDH

<400> SEQUENCE: 2
tgtcattcag caagcctgtg gt                                         22

<210> SEQ ID NO 3
<211> LENGTH: 24
<212> TYPE: DNA
<213> ORGANISM: Artificial Sequence
<220> FEATURE:
<223> OTHER INFORMATION: Forward Primer Mouse PSAT1
```

-continued

```
<400> SEQUENCE: 3
gatgaacatc ccatttcgca ttgg                                              24

<210> SEQ ID NO 4
<211> LENGTH: 24
<212> TYPE: DNA
<213> ORGANISM: Artificial Sequence
<220> FEATURE:
<223> OTHER INFORMATION: Reverse Primer Mouse PSAT1

<400> SEQUENCE: 4
gcgttataca gagaggcacg aatg                                              24

<210> SEQ ID NO 5
<211> LENGTH: 24
<212> TYPE: DNA
<213> ORGANISM: Artificial Sequence
<220> FEATURE:
<223> OTHER INFORMATION: Forward Primer Mouse PSPH

<400> SEQUENCE: 5
gagatggagc tacggacatg gaag                                              24

<210> SEQ ID NO 6
<211> LENGTH: 24
<212> TYPE: DNA
<213> ORGANISM: Artificial Sequence
<220> FEATURE:
<223> OTHER INFORMATION: Reverse Primer Mouse PSPH

<400> SEQUENCE: 6
ctcctccagt tctcccagca gctc                                              24

<210> SEQ ID NO 7
<211> LENGTH: 25
<212> TYPE: DNA
<213> ORGANISM: Artificial Sequence
<220> FEATURE:
<223> OTHER INFORMATION: MTAP_gRNA_1F sequence ONE

<400> SEQUENCE: 7
caccggtttt gccccaaaac gagag                                             25

<210> SEQ ID NO 8
<211> LENGTH: 25
<212> TYPE: DNA
<213> ORGANISM: Artificial Sequence
<220> FEATURE:
<223> OTHER INFORMATION: MTAP_gRNA_1R sequence ONE

<400> SEQUENCE: 8
aaacctctcg ttttggggca aaacc                                             25

<210> SEQ ID NO 9
<211> LENGTH: 25
<212> TYPE: DNA
<213> ORGANISM: Artificial Sequence
<220> FEATURE:
<223> OTHER INFORMATION: MTAP_gRNA_2F sequence TWO

<400> SEQUENCE: 9
caccggcctg gtagttgacc tttga                                             25

<210> SEQ ID NO 10
```

```
<211> LENGTH: 25
<212> TYPE: DNA
<213> ORGANISM: Artificial Sequence
<220> FEATURE:
<223> OTHER INFORMATION: MTAP_gRNA_2R sequence TWO

<400> SEQUENCE: 10
aaactcaaag gtcaactacc aggcc                                          25

<210> SEQ ID NO 11
<211> LENGTH: 25
<212> TYPE: DNA
<213> ORGANISM: Artificial Sequence
<220> FEATURE:
<223> OTHER INFORMATION: NTC_gRNA_1F

<400> SEQUENCE: 11
caccgaaaat agcagtaaac tcaac                                          25

<210> SEQ ID NO 12
<211> LENGTH: 25
<212> TYPE: DNA
<213> ORGANISM: Artificial Sequence
<220> FEATURE:
<223> OTHER INFORMATION: NTC_gRNA_1R

<400> SEQUENCE: 12
aaacgttgag tttactgcta ttttc                                          25
```